(12) United States Patent
Vaultier et al.

(10) Patent No.: US 9,452,425 B2
(45) Date of Patent: Sep. 27, 2016

(54) COMPOSITIONS CONTAINING IONIC LIQUIDS AND THEIR USES, IN PARTICULAR IN ORGANIC SYNTHESIS

(75) Inventors: Michel Vaultier, Chateaugiron (FR); Said Gmouh, Casablanca (MA)

(73) Assignees: CENTRE NATIONAL DE LA RECHERCHE SCIENTIFIQUE, Paris (FR); UNIVERSITE DE RENNES 1, Rennes (FR)

( * ) Notice: Subject to any disclaimer, the term of this patent is extended or adjusted under 35 U.S.C. 154(b) by 653 days.

(21) Appl. No.: 12/463,027

(22) Filed: May 8, 2009

(65) Prior Publication Data

US 2009/0326228 A1 Dec. 31, 2009

Related U.S. Application Data

(62) Division of application No. 10/529,361, filed as application No. PCT/FR03/02795 on Sep. 23, 2003, now abandoned.

(30) Foreign Application Priority Data

Sep. 26, 2002 (FR) .................................... 02 11910

(51) Int. Cl.
*C07C 409/44* (2006.01)
*B01J 31/02* (2006.01)
*B01J 31/04* (2006.01)
*B01J 31/30* (2006.01)
*C07B 37/02* (2006.01)
*C07B 37/04* (2006.01)
*C07B 37/12* (2006.01)
*C07C 67/03* (2006.01)
*C07C 67/343* (2006.01)
*C07C 67/347* (2006.01)

(52) U.S. Cl.
CPC ......... *B01J 31/0281* (2013.01); *B01J 31/0239* (2013.01); *B01J 31/0288* (2013.01); *B01J 31/04* (2013.01); *B01J 31/30* (2013.01); *C07B 37/02* (2013.01); *C07B 37/04* (2013.01); *C07B 37/12* (2013.01); *C07C 67/03* (2013.01); *C07C 67/343* (2013.01); *C07C 67/347* (2013.01); *B01J 31/0224* (2013.01); *B01J 2231/326* (2013.01); *B01J 2231/341* (2013.01); *B01J 2231/4211* (2013.01); *B01J 2231/4261* (2013.01); *B01J 2231/4266* (2013.01); *C07C 2102/42* (2013.01)

(58) Field of Classification Search
CPC ... C07C 67/03; C07C 67/343; C07C 67/347; C07C 69/618; C07C 69/65; C07C 69/732; C07C 69/734; C07C 69/753; C07C 69/76; C07C 2102/42; B01J 2231/326; B01J 2231/341; B01J 2231/4211; B01J 2231/4261; B01J 2231/4266; B01J 31/0224; B01J 31/0239; B01J 31/0281; B01J 31/0288; B01J 31/04; B01J 31/30; C07B 37/02; C07B 37/04; C07B 37/12
USPC ................... 546/79, 167, 347; 560/104, 60; 568/312, 642; 502/150; 548/110; 564/281
See application file for complete search history.

(56) References Cited

U.S. PATENT DOCUMENTS

| 4,463,071 A | 7/1984 | Gifford et al. |
| 6,248,540 B1 | 6/2001 | Weinberg et al. |
| 2002/0010291 A1 | 1/2002 | Murphy |

OTHER PUBLICATIONS

Calo et al. (Influence of Ionic Liquids on Pd-Catalyzed Carbon-Carbon Bond Formation, Verlag der Zeitschrift Fur Naturforschung, Tubingen, 56a, 702-706, 2001).*
Hiroshige et al. (Formation of C-C Bond in Solid Phase Synthesis Using The Heck Reaction, Tetrahedron Letters, 36(26) 4567-4570, 1995).*
McFarlane et al. (High conductivity molten salts based on the imide ion, Electrochimica Acta 45, 1271-1278, 2000).*
Bumagin et al. (Synthesis of substituted cinnamic acids and cinnamonitriles via palladium catalyzed coupling reaction of aryl halides with acrylic acid and acrylonitrile in aqueous media, Journal of organometallic chemistry, 371, 397-401, 1989).*
Zukowski et al (Resolution of Ortho, Meta, and Para Isomers of Some Disubstituted Benzene Derivatives via α- and β-Cyclodextrin Inclusion Complexes, Using Reversed-Phase High-Performance Liquid Chromatography, Anal. Chem. 57, 2215-2219, 1985).*
Joan Fraga-Dubreuil et al. (Grafted ionic liquid-phase-supported synthesis of small organic molecules, Tetrahedron Letters, 42, 6097-6100, 2001).*
Fraga-Dubreuil J. et al., "Grafted Ionic Liguid-Phase-Supported Synthesis of Small Organic Molecules", Tetrahedron Letters, Elsevier Science Publishers, Amsterdam, NL, vol. 42, No. 35, Aug. 27, 2001, pp. 6097-6100, XP004298190.

(Continued)

*Primary Examiner* — Yevegeny Valenrod
*Assistant Examiner* — Blaine G Doletski
(74) *Attorney, Agent, or Firm* — Young & Thompson

(57) ABSTRACT

An ionic liquid is used as liquid matrix for organic synthesis in homogeneous phase on soluble support, the ionic liquid being presented in liquid or solid form at ambient temperature, of formula $A_1^+ X_1^-$, $A_1^+$ representing a cation, functional or non-functional, or a mixture of cations in which either none of the cations is functional or at least one of the cations is functional, and $X_1^-$ an anion, functional or non-functional, or a mixture of anions in which either none of the anions is functional or at least one of the anions is functional.

16 Claims, 13 Drawing Sheets

(56) References Cited

OTHER PUBLICATIONS

Dubreuil J.F. et al., "Rate Accelarations of 1, 3-dipolar cycloaddition Reactions in Ionic Liquids", Tetrahedron Letters, Elsevier Science Publishers, Amsterdam, NL, vol. 41, No. 38, Sep. 16, 2000, pp. 7351-7355, XP004211923.

Wasserscheid P. et al., "Ionic Liquids New Solutions for Transition Metal Catalysis", Angewandante Chemie, International Edition, Verlag Chemie, Weinheim, Germany, vol. 39, No. 21, Oct. 27, 2000, pp. 3772, 3778, 3780-3787, XP002218385.

Welton T., Room-Temperature Ionic Liquids. Solvents for Synthesis and Catalysis, Chemical Reviews, American Chemical Society, Easton, US, vol. 99, 1999, pp. 2071-2083, XP002162959.

* cited by examiner

COMPOSITIONS CONTAINING IONIC LIQUIDS AND THEIR USES, IN PARTICULAR IN ORGANIC SYNTHESIS

This application is a division of application Ser. No. 10/529,361 filed on Nov. 3, 2005; which is the 35 U.S.C. 371 national stage of International application PCT/FR2003/002795 filed on Sep. 23, 2003; which claimed priority to French application 02/11910 filed Sep. 26, 2002. The entire contents of each of the above-identified applications are hereby incorporated by reference.

The present invention relates to compositions containing ionic liquids, as well as their uses, in particular in organic synthesis.

Synthesis on solid support has become a very effective method often used for the production of combinatorial libraries of products (Wilson et al., 1997; Charken et al., 1996; Sammelson et al., 2001; Gravet et al., 1997; Wentworth et al., 1999). Thanks to the development of high-throughput tests for biological evaluation and the discovery of new biologically-active products, combinatorial libraries have become very important in pharmaceutical chemistry and in agricultural chemistry. The use of suitably functionalized Merrifield resins has made it possible to develop a multitude of methodologies for synthesis on solid support (Thompson et al., 1996; Dörwald, 2000). These solid-support methodologies have numerous advantages such as easy purification by simple washing, the possibility of using various techniques such as parallel or "split-and-mix" synthesis making it possible to simultaneously produce a large quantity of products. However, numerous problems are associated with these methods, such as the price of the functionalized resins and their low specific load which is very often less than 1 mmol/g of resin and only very rarely reaches 2 mmol/g of resin. Another difficulty is due to the fact that the reactions take place in heterogeneous phase, which requires a particular development in each case, the reaction conditions being generally different from those used in solution. Moreover, there are few effective means of analysis for monitoring the reactions. Other difficulties can arise in particular during the release of the products sought and it is difficult to use high-temperature reactions, conditions which destroy the solid supports, as well as, moreover, unsuitable magnetic or mechanical stirring.

The use of soluble polymers (Sammelson et al., 2001; Gravet et al., 1997) proves to be a useful alternative. In fact, the substitution of insoluble resins by a soluble polymer such as polyethylene glycol or PEG, makes it possible to go back to experimental procedures familiar to chemistry in solution, whilst preserving simple purification. Moreover, it is possible to use the different methods of analysis for the characterization of the product obtained, without prior release from the support. However, various problems are associated with this methodology such as the high mass of polymers comprised between 2000 and 20,000 daltons. The direct consequence is a low specific load since a decimolar solution already contains 500 grams of polymer per liter for a PEG with a mass of 5000 which would at the most produce one decimole of expected product per one liter of solution. Such concentrations are used only rarely as they lead to problems of viscosity of the medium. Another problem is the purification of the products and the recycling of PEGs.

Thus, there exists a real need for new supports for supported organic synthesis.

For the last few years, ionic liquids (Welton et al., 1999; Wasserscheid et al., 2000) have increasingly been used in organic synthesis and in catalysis as they have a certain number of useful and important physico-chemical properties such as their high thermal stability, their low volatilities and their very low vapor pressures, their low inflammability, their strong solubilization power of the salts as well as of the neutral organic molecules and polymers and finally the possibility of easy recycling.

One object of the present invention is to provide a novel use of ionic liquids as novel matrices for organic synthesis in homogeneous phase on soluble support(s).

One object of the present invention is to provide novel matrices for the organic synthesis on soluble support(s), which are easily recyclable, liquid in a very broad range of temperature, having a very low vapor pressure and possessing a very strong solubilization power.

One object of the present invention is to provide novel matrices for organic synthesis on soluble support(s), said soluble support(s) being dissolved in said matrices.

One object of the present invention is to provide novel matrices for organic synthesis on soluble support(s) in place of the resins but without the drawbacks linked to reactions in heterogeneous phase on solid support.

One object of the present invention is to provide a novel use of ionic liquids, by conferring resin-type properties on these ionic liquids.

The present invention relates to the use of an ionic liquid, as liquid matrix for organic synthesis in homogeneous phase on soluble support, without volatile organic solvent, said ionic liquid being presented in liquid or solid form at ambient temperature, of formula $A_1^+ X_1^-$, $A_1^+$ representing a cation, functional or non-functional, or a mixture of cations in which either none of the cations is functional or at least one of the cations is functional, and $X_1^-$ an anion, functional or non-functional, or a mixture of anions in which either none of the anions is functional or at least one of the anions is functional.

The expression "ionic liquid" designates a salt or a mixture of salts the melting point of which is comprised between $-100°$ C. and $250°$ C.

The expression "liquid matrix" designates an ionic liquid capable of solubilizing one or more chemical species such as mineral or organic salts, organic molecules, polymers of natural or synthetic origin. The expression "liquid matrix" therefore designates a solvent constituted by an ionic liquid. These novel solvents are non-volatile and have a very low vapor pressure. They are also polar and have the ability to dissolve functional onium salts which can then serve as soluble supports.

The expression "soluble support" designates a salt dissolved in the ionic liquid matrix carrying one or more functions allowing the catching of molecules and their subsequent functionalization as well as the release at the end of the reaction sequence.

The expression "organic synthesis in homogeneous phase on soluble support" designates the conversion(s) of the chemical function(s) carried by the soluble support without modifying the liquid matrix, followed by a cleavage reaction releasing the sought molecule(s).

The expression "functional cation" designates a molecular group which possesses at least one chemical function, part of this group carrying a positive charge.

The expression "functional anion" designates a molecular group which possesses at least one chemical function, part of this group carrying a negative charge.

The expression "non-functional cation" designates a molecular group which possesses no chemical function, part of this group carrying a positive charge.

The expression "non-functional anion" designates a molecular group which possesses no chemical function, part of this group carrying a negative charge.

When the $A_1^+X_1^-$ matrix comprises no functional ion, it serves as a reaction medium which is inert vis-à-vis reagents but is capable of dissolving them.

When the $A_1^+X_1^-$ matrix comprises at least one functional ion, it can serve on the one hand as a reaction medium and on the other hand as a soluble support.

The $A_1^+X_1^-$ matrix can contain several non-functional cations and/or anions for the following reasons:

On the one hand, the mixture of cations can originate from industry. In fact, numerous detergents based on ammonium or phosphonium cations are mixtures of salts produced as such by synthesis. They correspond to cuts. Thousands of tons are thus produced at a low price. The benefit of using such mixtures within the framework of the present invention is therefore economic.

The fact of having mixtures is not a problem, if all the constituents of the mixture are chemically inert under conditions of use. For example, a mixture of tetralkylammonium or phosphonium non-functional salts can be used.

On the other hand, the melting point of a mixture is lower than the melting point of the constituent of the mixture which melts at the lowest temperature. It can therefore be very important to resort to a mixture in order to have an ionic liquid at a reasonable melting temperature.

Certain functionalized salts, in particular those with large anions such as $NTf_2^-$, $PF_6^-$, $BF_4^-$ or $CF_3SO_3^-$, can be liquid at ambient temperature or can melt at low temperature, for example

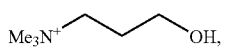

$NTf_2^-$ is liquid at ambient temperature. This ionic liquid is prepared by alkylation of $Me_3N$ according to the following reaction:

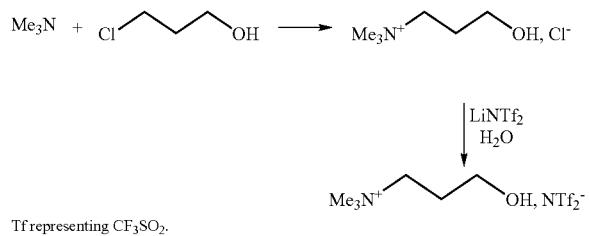

Tf representing $CF_3SO_2$.

The present invention relates to the use as defined above, characterized in that $A_1^+$ represents a non-functional cation or a mixture of non-functional cations and $X_1^-$ a non-functional anion or a mixture of non-functional anions.

The present invention also relates to the use as defined above, characterized in that:

$A_1^+$ represents a functional cation or a mixture of cations at least one of which of is functional, and/or $X_1^-$ represents a functional anion or a mixture of anions at least one of which is functional, said functional cations and functional anions corresponding to an ionic entity, namely respectively cationic or anionic, linked to at least one function $F_i$, $F_i$ varying from $F_0$ to $F_n$, n being an integer varying from 1 to 10.

The expression "ionic entity" designates the part of the cation or of the anion, which carries the charge, respectively positive or negative.

The function $F_i$ is in particular chosen from the following functions:

hydroxyl, carboxylic, amide, sulphone, primary amine, secondary amine, aldehyde, ketone, ethenyl, ethynyl, dienyl, ether, epoxide, phosphine (primary, secondary or tertiary), azide, imine, ketene, cumulene, heterocumulene, thiol, thio-ether, sulphoxide, phosphorus-containing groups, heterocycles, sulphonic acid, silane, stannane or functional aryl, and any function resulting from a chemical, thermal, photochemical conversion or a conversion by micro-wave irradiation of the preceding functions.

The present invention relates to the use of an ionic liquid as defined above, for the preparation of a stable composition containing in solution:

at least said ionic liquid of formula $A_1^+X_1^-$, playing the role of liquid matrix and, at least one functionalized salt (salt with a dedicated task), in particular functionalized onium salt, of formula $A_2^+X_2^-$, as reaction support, the functionalized salt, in particular the functionalized onium salt, being dissolved in the liquid matrix, in order to form a homogeneous phase, $A_1^+$ representing a non-functional cation or a mixture of cations in which none of the cations is functional, and $X_1^-$ representing a non-functional anion or a mixture of anions in which none of the anions is functional, $A_2^+$ representing a cation, functional or non-functional, or a mixture of cations in which none of the cations is functional or in which at least one of the cations is functional, and $X_2^-$ representing an anion, functional or non-functional, or a mixture of anions in which none of the anions is functional or in which at least one of the anions is functional, provided that $A_2^+$ and/or $X_2^-$ represent(s) or comprise(s) a functional cation and a functional anion respectively, said functional cations and functional anions corresponding to a ionic entity Y—, namely cationic $Y^+$— or anionic $Y^-$— respectively, optionally linked via an L arm, in particular an alkyl group comprising 1 to 20 carbon atoms, to at least one function $F_i$, $F_i$ varying from $F_0$ to $F_n$, n being an integer varying from 1 to 10, the functional cation being representable in the form $Y^+$-L-$F_i$, and the functional anion in the form $Y^-$-(L)$_k$-$F_i$, k being equal to 0 or 1, and the functional anion possibly representing, when k is equal to 0, a single anion, corresponding to $Y^-$—$F_i$, in particular chosen from: $OH^-$, $F^-$, $CN^-$, $RO^-$ or $RS^-$, R representing an alkyl group comprising 1 to 20 carbon atoms or an aryl group comprising 6 to 30 carbon atoms.

The expression "stable composition" designates the homogeneous mixture composed of the $A_1^+X_1^-$ liquid matrix and of the $A_2^+X_2^-$ functionalized salt(s). This composition is described as stable to the extent that it does not undergo spontaneous conversions over time.

It can be verified that this composition is stable by spectroscopic analysis using NMR, IR, visible UV, of the mass spectrometry or chromatography methods.

The expression "functionalized salt (salt with a dedicated task)" designates an entity of type $A_2^+X_2^-$ in which the cation and/or the anion carries a function $F_i$ as previously defined. This function confers chemical and/or physico-chemical properties upon said functionalized salt and upon the stable composition, of which it forms part.

The expression "functionalized onium salt" designates ammonium, phosphonium, sulphonium salts, as well as all the salts resulting from the quaternization of an amine, a phosphine, a thioether or a heterocycle containing one or more of these heteroatoms, and carrying at least one function $F_i$. This expression also designates an onium salt the cation of which as defined above is not functionalized but the anion of which carries a function $F_i$. This expression can also designate a salt the anion and the cation of which carry a function $F_i$.

A preferred functionalized onium salt is in particular chosen from the following:

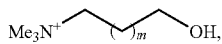

$Cl^-$ or $NTf_2^-$ or $PF_6^-$ or $BF_4^-$

$Cl^-$ or $NTf_2^-$ or $PF_6^-$ or $BF_4^-$

$Cl^-$ or $NTf_2^-$ or $PF_6^-$ or $BF_4^-$ m being an integer from 0 to 20.

A preferred non-functionalized onium salt is in particular chosen from the following: imidazolium, pyridinium $Me_3N^+$—Bu or $Bu_3P^+$-Me cations, $NTf_2^-$, $PF_6^-$ or $BF_4^-$ anions.

The expression "reaction support" designates any salt of $A_2^+ X_2^-$ type functionalized by a function $F_i$ which can be converted and cleaved in order to release the sought molecule at the end of the reaction sequence. This expression designates in particular any salt of $A_2^+ X_2^-$ type functionalized by a function $F_n$ (last function in the reaction chain) which can be cleaved in order to release the sought molecule at the end of the reaction sequence.

In the term "Y—", the dash "-" represents the optional bond between the ionic entity and the L arm.

In the term "$Y^+$—", the dash "-" represents the optional bond between the cationic entity and the L arm.

In the term "$Y^-$—", the dash "-" represents the optional bond between the anionic entity and the L arm.

The term "L arm" designates an alkyl or aralkyl chain which can contain one or more heteroatoms such as nitrogen, phosphorus, sulphur, oxygen, silicon, tin, containing between 1 and 30 carbon atoms, and said arm is in particular chosen from an alkyl chain containing 2 to 10 carbon atoms and 1 to 6 oxygen or nitrogen atoms.

In this embodiment of the invention, the ionic matrix is non-functional and it is necessary that the $A_2^+ X_2^-$ onium salt be functionalized, either via the $A_2^+$ cation, or via the $X_2^-$ anion, or via the $A_2^+$ cation and the $X_2^-$ anion.

The functionalization of the cation alone means that the anion is simply a "spectator" during the functional modifications and is there only to ensure electric neutrality. The fact of only having a function on the cation with an inert anion leads to a simplification of the control of the reactions.

Similarly, if the cation is chemically inert, it is possible to modify the anion without worrying about the cation. The use of a functional anion has additional benefits:
  a simplicity of synthesis of the functionalized salt by simple neutralization or metathesis of the anion, for example:

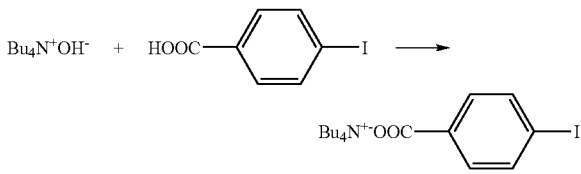

the ammonium carboxylate solution thus obtained can be used directly in a Heck or Suzuki coupling;
in terms of cleavage, it is sufficient to wash with a solution of HCl, in particular in order to release, in the case of the abovementioned example, a carboxylic acid:

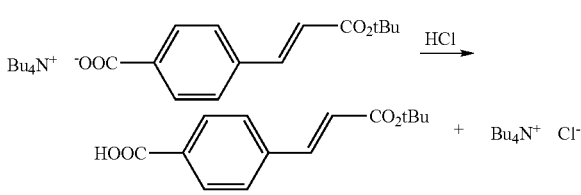

compound obtained after a Heck coupling
this example relates to a Bronsted acid;
the anion can also react by neutralization of a Lewis acid for example:

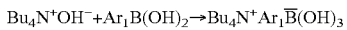

the anion thus obtained can then serve as a reaction intermediate, in particular in Suzuki coupling, according to the following reaction:

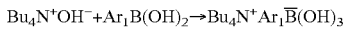

it can be noted that this coupling is "releasing" to the extent that there is no need for a cleavage reaction in order to recover the final product.

The use of a functionalized salt involving both the anion and the cation is useful in more complicated sequences. It is possible to selectively modify the cation or the anion and to give rise to the reaction of the anion with the cation in a final conversion via the functions that carry the cation and the anion. It is also possible to start from a functionalized salt only the cation of which is functionalized. The function $F_0$ is modified in order to obtain the function $F_i$ and, by metathesis, a functional anion is introduced the function of which can react with the function $F_i$ carried by the functionalized cation.

The present invention relates to the use as defined above, for the preparation of a stable composition containing in solution:
  at least one first part of said ionic liquid of formula $A_1^+ X_1^-$, the cation and/or the anion of which correspond(s) to an ionic entity linked to one or more initial functions $F_0$, playing the role of liquid matrix, and
  at least one second part of said ionic liquid of formula $A_1^+ X_1^-$, in which said initial function(s) $F_0$ are converted into first novel functions, conferring upon said second part of said ionic liquid the role of functionalized salt and of reaction support,
the functionalized salt and the liquid matrix forming a homogeneous phase,
the abovementioned first novel functions of the second part of said ionic liquid being capable of subsequently being converted into other functions, without affecting one or more initial functions $F_0$ of the first part of said ionic liquid.

The expression "without affecting one or more initial functions $F_0$ of the first part of said ionic liquid" means that the first novel functions of the second part of said ionic liquid are subsequently converted into other functions, by chemoselective conversions.

This particular embodiment of the invention corresponds to the case where the $A_1^+X_1^-$ ionic liquid plays the role of both liquid matrix and functionalized salt.

The case where the $A_1^+X_1^-$ ionic liquid plays the role of both liquid matrix and functionalized salt is useful to the extent that one starts with a single initial product. Moreover, after reaction, during cleavage by transesterification or transamidation, for example, the starting salt is regenerated and therefore recycled. Moreover, the function $F_0$ of the starting salt can confer particular reaction activation properties on the medium, for example by hydrogen bonding or by any other activation dependent on the function $F_0$.

The present invention relates to the use of an ionic liquid as defined above, characterized in that the $A_2^+$ cation and/or the $X_2^-$ anion of the functionalized salt(s), corresponding to a Y-ionic entity linked to at least one function $F_i$, are immobilized in the liquid matrix and cannot be extracted from the liquid matrix by standard extraction means, in particular by solvent, and in which the function(s) $F_i$ of the functionalized salt(s) can be converted at the end of at least one reaction resulting from the addition of at least one reagent to said composition.

The term "immobilized" means that the functionalized salt cannot be extracted from the matrix by standard means such as extraction or distillation.

The expression "cannot be extracted from the liquid matrix by standard extraction means" designates the fact that the mixture formed by the liquid matrix and the functionalized salt can be washed using standard solvents or heated under vacuum without loss of said functionalized salt. This allows in particular the use of an excess of reagents which can be eliminated when the reaction is completed as in the case of resins.

The present invention is based on the unexpected feature according to which the mixture of a functionalized salt in a $A_1^+X_1^-$ liquid matrix results in the immobilization of said functionalized salt in said liquid matrix.

The present invention relates to the use of an ionic liquid as defined above, characterized in that several functionalized salts are immobilized.

It is possible to confer on a solution of several salts in an ionic liquid matrix several properties that can be used in a cascade or multicomponent.

The present invention relates to the use as defined above, characterized in that the $A_2^+$ cation is functional.

According to an advantageous embodiment, the present invention relates to the use as defined above, characterized in that the $A_2^+$ cation is functional and the $X_2^-$ anion is non-functional.

The present invention relates to the use as defined above, characterized in that the $X_2^-$ anion is functional.

According to an advantageous embodiment, the present invention relates to the use as defined above, characterized in that the $X_2^-$ cation is functional and the $A_2^+$ anion is non-functional.

The present invention relates to the use as defined above, characterized in that $A_2^+$ and $X_2^-$ are functional.

The present invention relates to the use as defined above, characterized in that:
either the ionic liquid of formula $A_1^+X_1^-$ is solid at ambient temperature and is liquefiable within a temperature range from approximately 25° C. to approximately 250° C., in particular from approximately 30° C. to approximately 150° C., and the $A_2^+X_2^-$ functionalized salt is solid at ambient temperature and is soluble in the liquefied $A_1^+X_1^-$ ionic liquid, in order to form a homogeneous phase, or the ionic liquid of formula $A_1^+X_1^-$ is solid at ambient temperature and is liquefiable within a temperature range from approximately 25° C. to approximately 250° C., in particular from approximately 30° C. to approximately 150° C., and the $A_2^+X_2^-$ functionalized salt is liquid at ambient temperature, and is miscible with the liquefied $A_1^+X_1^-$ ionic liquid, in order to form a homogeneous phase, or the $A_1^+X_1^-$ ionic liquid is liquid at ambient temperature and the $A_2^+X_2^-$ functionalized salt is liquid at ambient temperature and miscible with the $A_1^+X_1^-$ ionic liquid, in order to form a homogeneous phase, or the $A_1^+X_1^-$ ionic liquid is liquid at ambient temperature and the $A_2^+X_2^-$ functionalized salt is solid at ambient temperature and is soluble or partially soluble in the $A_1^+X_1^-$ ionic liquid within a temperature range from approximately 25° C. to approximately 250° C., in particular from approximately 30° C. to approximately 150° C., in order to form a homogeneous phase.

When the ionic liquid of formula $A_1^+X_1^-$ and the $A_2^+X_2^-$ functionalized salt are solid at ambient temperature, after the conversions of the initial function $F_0$ to functions $F_i$ and cleavage, a mixture formed from a solid and the sought molecule is obtained, from which it is possible to extract this molecule, by simple addition of a solvent solubilizing the molecule and not the functionalized salts, and by simple filtration. This embodiment therefore makes it possible to add a few advantages specific to the solid-support technique, whilst preserving the advantages of the soluble-support reactions.

When the ionic liquid of formula $A_1^+X_1^-$ is solid at ambient temperature and the functionalized salt $A_2^+X_2^-$ is liquid at ambient temperature, this is the case where a liquid functionalized salt is added to a solid matrix at ambient temperature. A homogeneous phase is obtained on melting of the mixture which can either remain liquid, or produce a solid, or produce a solid/liquid heterogeneous mixture.

The case where the $A_1^+X_1^-$ ionic liquid and the $A_2^+X_2^-$ functionalized salt are liquids at ambient temperature corresponds to the standard case making it possible to carry out reactions at ambient or sub-ambient temperature.

When the $A_1^+X_1^-$ ionic liquid is liquid at ambient temperature and the $A_2^+X_2^-$ functionalized salt is solid at ambient temperature, several distinct cases can be encountered, and in particular:
either the $A_2^+X_2^-$ solid is soluble in $A_1^+X_1^-$ and the operation is carried out in solution as in the preceding case; this case is very frequent due for example to the use of chlorides, bromides or iodides which are solid at ambient temperature, inexpensive and easy to purify by recrystallization;

or the solid $A_2^+X_2^-$ is soluble in $A_1^+X_1^-$ at a temperature higher than ambient temperature, which makes it necessary to work at this temperature in order to obtain a homogeneous phase and to avoid reprecipitation; if not, once the functionalized salt is dissolved, a solution is recovered at ambient temperature without reprecipitation;

or it is necessary to dissolve the $A_2^+X_2^-$ functionalized salt in a standard solvent, to mix the solution with liquid $A_1^+X_1^-$, then to eliminate the solvent under vacuum in order to obtain a solution of $A_2^+X_2^-$.

The present invention relates to the use as defined above, characterized in that:
either the ionic liquid of formula $A_1^+X_1^-$ is liquid at ambient temperature,
or the ionic liquid of formula $A_1^+X_1^-$ is solid at ambient temperature and is liquefiable within a temperature range from approximately 25° C. to approximately 250° C., in particular from approximately 30° C. to approximately 150° C.

The present invention also relates to the use as defined above, characterized in that the ionic liquid of formula $A_1^+X_1^-$, playing the role of liquid matrix, has a viscosity less than or equal to approximately 1500 cp (15 N·s/m²), in particular less than approximately 500 cp (5 N·s/m²) and preferably less than approximately 200 cp (2 N·s/m²).

Thus, the table below corresponds to the viscosities at 23° C. of the preferred ionic liquids of the invention.

| Ionic liquid | Viscosity in (cP) at 23° C. |
|---|---|
| [btma][NTf$_2$] | 58 |
| [htma][NTf$_2$] | 64 |
| [C$_3$OHtma][NTf$_2$] | 94.3 |
| [C$_3$CNtma][NTf$_2$] | 62 |
| [C$_5$CNtma][NTf$_2$] | 69 |

[btma][NTf$_2$] = [C$_4$tma][NTf$_2$] = [Me$_3$N$^+$—C$_4$H$_9$] [N$^-$(SO$_2$CF$_3$)$_2$]
[htma][NTf$_2$] = [C$_6$tma][NTf$_2$] = [Me$_3$N$^+$—C$_6$H$_{11}$] [N$^-$(SO$_2$CF$_3$)$_2$]
[C$_3$OHtma][NTf$_2$] = [Me$_3$N$^+$—(CH$_2$)$_2$CH$_2$OH] [N$^-$(SO$_2$CF$_3$)$_2$]
[C$_3$CNtma][NTf$_2$] = [Me$_3$N$^+$—(CH$_2$)$_2$CH$_2$CN] [N$^-$(SO$_2$CF$_3$)$_2$]
[C$_5$CNtma][NTf$_2$] = [Me$_3$N$^+$—(CH$_2$)$_4$CH$_2$CN] [N$^-$(SO$_2$CF$_3$)$_2$]

Method and Apparatus for Measuring Dynamic Viscosity:

Dynamic viscosity measurements were carried out at 23° C. on a Rheolyst AR 1000 type microviscosimeter (TA instruments) equipped with a steel cone-plate with a diameter P=40 mm and angle t=1 degree 1 minute. The procedure is applied from 0.06 to 200 s$^{-1}$ for 3 minutes with 20 points per decade. The device is computer-controlled with Rheology Advantage Instrument Control AR software.

The present invention relates to a stable composition containing in solution:
at least said ionic liquid of formula $A_1^+X_1^-$, playing the role of liquid matrix and,
at least one functionalized salt (salt with a dedicated task), in particular functionalized onium salt, of formula $A_2^+X_2^-$, as reaction support,
the functionalized salt, in particular the functionalized onium salt, being dissolved in the liquid matrix, in order to form a homogeneous phase,
$A_1^+$ representing a non-functional cation or a mixture of cations in which none of the cations is functional, and $X_1^-$ representing a non-functional anion or a mixture of anions in which none of the anions is functional,
$A_2^+$ representing a cation, functional or non-functional, or a mixture of cations in which none of the cations is functional or in which at least one of the cations is functional, and $X_2^-$ representing an anion, functional or non-functional, or a mixture of anions in which none of the anions is functional or in which at least one of the anions is functional,
provided that $A_2^+$ and/or $X_2^-$ represent(s) or comprise(s) a functional cation and a functional anion respectively,
said functional cations and functional anions corresponding to an ionic entity Y—, namely cationic Y$^+$— or anionic Y$^-$— respectively, optionally linked via an L arm, in particular an alkyl group comprising 1 to 20 carbon atoms, to at least one function $F_i$, $F_i$ varying from $F_0$ to $F_n$, n being an integer varying from 1 to 10, the functional cation being representable in the form Y$^+$-L-F$_i$, and the functional anion in the form Y$^-$-(L)$_k$-F$_i$, k being equal to 0 or 1, and the functional anion possibly representing, when k is equal to 0, a single anion, corresponding to Y$^-$—F$_i$, in particular chosen from: OH$^-$, F$^-$, CN$^-$, RO$^-$ or RS$^-$, R representing an alkyl group comprising 1 to 20 carbon atoms or an aryl group comprising 6 to 30 carbon atoms.

The present invention relates to a stable composition containing in solution:
at least one first part of said ionic liquid of formula $A_1^+X_1^-$, the cation and/or anion of which correspond(s) to an ionic entity linked to one or more initial functions $F_0$, playing the role of liquid matrix, and
at least one second part of said ionic liquid of formula $A_1^+X_1^-$, in which said initial function or functions $F_0$ are converted into first novel functions, conferring on said second part of said ionic liquid the role of functionalized salt and reaction support,
the functionalized salt and the liquid matrix forming a homogeneous phase,
the abovementioned first novel functions of the second part of said ionic liquid being capable of being subsequently converted to other functions, without affecting the initial function or functions $F_0$ of the first part of said ionic liquid.

According to an advantageous embodiment of the present invention, a composition of the invention is characterized in that the $A_2^+$ cation and/or the $X_2^-$ anion of the functionalized salt or salts, corresponding to an ionic entity Y— linked to at least one function $F_i$, are immobilized in the liquid matrix and cannot be extracted from the liquid matrix by standard means of extraction, in particular by solvent.

An advantageous composition of the present invention is characterized in that the liquid matrix is non-reactive vis-à-vis the functionalized salt.

The property of non-reactivity of the matrix vis-à-vis the salt is verified for example using the usual spectroscopic techniques such as $^1$H, $^{13}$C NMR, mass spectrometry, or HPLC analysis.

Another advantageous composition of the present invention is characterized in that $A_2^+$ is a functional cation.

Another advantageous composition of the present invention is characterized in that the $X_1^-$ and $X_2^-$ anions are identical.

This particular case relates in particular to the case of large anions such as NTf$_2^-$, BF$_4^-$, PF$_6^-$, CF$_3$SO$_3^-$ commonly used for the preparation of ionic liquids. This particular embodiment also promotes the solubility of one salt in another.

Another advantageous composition of the present invention is characterized in that the $X_1^-$ and $X_2^-$ anions are different. This particular case relates to the general case where a functionalized salt, for example a halide (Cl$^-$, Br$^-$, I$^-$, F$^-$) is dissolved in an ionic liquid matrix. This particular embodiment has the particular advantage of allowing the dissolution of inexpensive salts.

According to an advantageous embodiment, a composition according to the present invention is characterized in that:
the $X_1^-$ and $X_2^-$ anions are chosen from the following two families:
non-complex anions, chosen in particular from the BF$_4^-$, PF$_6^-$, CF$_3$SO$_3^-$, CH$_3$COO$^-$, CF$_3$CO$_2^-$, $^-$N(SO$_2$CF$_3$)$_2$ (or NTf$_2^-$) anions, the halides, the BR$_4^-$, RCO$_2^-$ or RSO$_3^-$ anions, R being an alkyl group comprising 1 to 20 carbon atoms or an aryl group comprising 6 to 30 carbon atoms, said R group also possibly representing a perfluorinated or partially fluorinated group, or the R'SO$_4^-$ anions, R' being a hydrogen atom, a methyl group or an ethyl group;
complex anions, resulting from the combination of a Lewis acid and a halide, preferably Cl$^-$ or F$^-$, of general formula MX$_j$, j being an integer comprised between 1 and 7, and M representing a metal, in particular chosen from aluminium, tin, zinc, bismuth, manganese, iron, copper, molybdenum, antimony, gallium or indium;

the $A_1^+$ and $A_2^+$ cations are chosen from the onium cations, such as the pyridinium, imidazolium, ammonium, phosphonium or sulphonium cations, substituted or non-substituted, and preferably ammonium or phosphonium.

An advantageous composition of the present invention is characterized in that the $A_2^+$ functional cation corresponds to a $Y^+$— cationic entity, linked, optionally via an L arm, in particular an alkyl group comprising 1 to 20 carbon atoms, to a function $F_0$, said function $F_0$ being chosen from the standard functions of organic chemistry, such as the hydroxyl, carboxylic, amide, sulphone, primary amine, secondary amine, aldehyde, ketone, ethenyl, ethynyl, dienyl, ether, epoxide, phosphine (primary, secondary or tertiary), azide, imine, ketene, cumulene, heterocumulene, thiol, thioether, sulphoxide, phosphorus-containing groups, heterocycles, sulphonic acid, silane, stannane or functional aryl functions.

According to an advantageous embodiment, a composition of the invention is characterized in that the ionic liquid is chosen from the following:

$(R_a)_3N^+—R_b, X_1^-$    $(R_a)_3P^+—R_b, X_1^-$

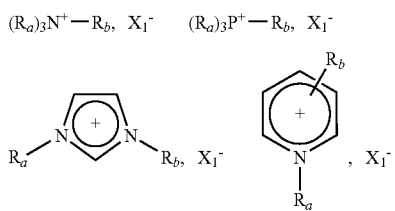

$R_a$ and $R_b$ representing linear or branched alkyl groups, comprising 1 to 20 carbon atoms, in particular an ethyl, propyl, butyl, pentyl, hexyl, heptyl or octyl group, or functional alkyl groups comprising 1 to 20 carbon atoms, or functional or non-functional aryl groups comprising 6 to 30 carbon atoms, $Bu_3P^+$-Me,$X_1^-$  $^\oplus P(C_6H_{13})_3C_{14}H_{29}$,$X_1^-$ $(C_8H_{17})_3N^+Me,X_1^-$ $X_1^-$ being in particular chosen from: $NTf_2^-$, $PF_6^-$, $BF_4^-$ or $CF_3SO_3^-$.

An advantageous composition of the invention is characterized in that the functionalized salt is chosen from the following:

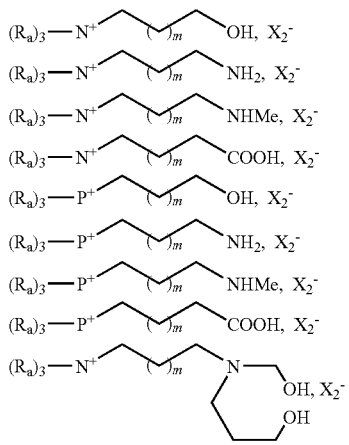

-continued

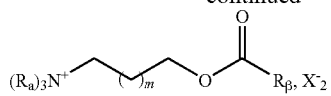

$X_2^-$ being chosen from: $NTf_2^-$, $PF_6^-$, $BF_4^-$, $Cl^-$, $Br^-$, $I^-$, $CF_3SO_3^-$, $MeSO_4^-$, $EtSO_4^-$, $MeSO_3^-$, $C_6H_5SO_3^-$, $pMeC_6H_4SO_3^-$, m being an integer comprised between 0 and 20, $R_\beta$ representing a substituted or non-substituted vinyl group, functional aryl group comprising 1 to 20 carbon atoms, or functional alkyl group comprising 6 to 30 carbon atoms, and $R_a$ representing a branched or non-branched alkyl group comprising 1 to 20 carbon atoms, in particular an ethyl, propyl, butyl, pentyl, hexyl, heptyl or octyl group.

According to an advantageous embodiment, a composition of the invention is characterized in that $X_2^-$ is a functional anion, corresponding in particular to an anion the $pK_A$ of the conjugated acid of which is less than 30, and is chosen in particular from the following anions:

$OH^-,F^-,R_cBZ_3^-,N_3^-,CN^-$, or

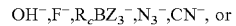

Z representing an —F, —OH, —OR moiety, R representing an alkyl group comprising 1 to 20 carbon atoms, V and W representing, independently of one another, an electroattractive moiety, in particular a cyano, alkoxycarbonyl moiety comprising 2 to 20 carbon atoms, acyl moiety comprising 2 to 20 carbon atoms, benzoyl, alkyl sulphonyl moiety comprising 1 to 20 carbon atoms, aryl sulphonyl moiety comprising 6 to 30 carbon atoms, dialkoxyphosphonyl moiety comprising 2 to 20 carbon atoms, $R_c$ representing a branched or non-branched, cyclic or non-cyclic alkyl moiety comprising 1 to 20 carbon atoms, or an aryl moiety comprising 6 to 30 carbon atoms, and in that the $A_2^+$ cation is chosen from the ammonium and phosphonium cations, in particular from the following cations:

$Me_3\overset{+}{N}$—$R_d$    $Et_3\overset{+}{N}$—$R_d$    $Bu_4\overset{+}{P}$—$R_d$ $R_d$ being an alkyl group comprising 1 to 20 carbon atoms.

The present invention also relates to the use of a composition as defined above, for continuous, discontinuous, combinatorial, or parallel organic synthesis, and/or for the preparation of libraries of products.

The present invention also relates to the use of a composition as defined above, for the implementation of a process for the preparation of a molecule G of an initial function $F_0$, linked, optionally via an L arm, in particular an alkyl group comprising 1 to 20 carbon atoms, to a $Y^+$-ionic entity, forming part of the $A_2^+$ cation of the $A_2^+X_2^-$, and/or $Y^-$-functionalized salt, forming part of the $X_2^-$ anion of the $A_2^+X_2^-$ functionalized salt, the cation being in the form $Y^+$-L-$F_0$ and/or the anion being in the form $Y^-$-$(L)_k$-$F_0$, k being equal to 0 or 1, which process comprises the steps:

of a first addition of a reagent $B_1$ into the abovementioned composition and the reaction between said function $F_0$, and the reagent $B_1$, leading to a function $F_1$, linked to the $Y^+$— ionic entity, forming part of the $A_2^+$ cation of the $A_2^+X_2^-$ functionalized salt, and/or to the ionic entity $Y^-$—, forming part of the $X_2^-$ anion of the $A_2^+X_2^-$ functionalized salt, according to one of the following reaction diagrams:

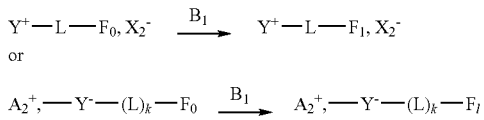

of n−1 successive additions of $B_i$ reagents, $1 < i \le n$, n varying from 2 to 10, to the abovementioned composition, allowing, at each addition, the reaction between the reagent $B_i$ and a function $F_{i-1}$, leading to the obtaining of a function $F_i$, the $(n-1)^{th}$ addition of the reagent $B_n$ to the function $F_{n-1}$ leading to the obtaining of the function $F_n$, the n−1 additions being representable according to one of the following reaction diagrams:

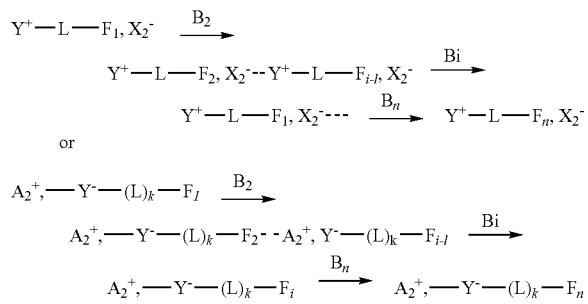

of cleavage of the function $F_n$, linked to the $Y^+$— or $Y^-$— ionic entity respectively of the $A_2^+$ cation and/or of the $X_2^-$ anion, making it possible to recover on the one hand the $A_2^+X_2^-$ functionalized salt in the form $Y^+$-L-$F_0$, $X_2^-$ or $A_2^+$, $Y^-$-(L)$_k$-$F_0$, in solution in the $A_1^+X_1^-$ ionic liquid matrix, or in the form $Y^+$-L-$F'_0$, $X_2^-$ or $A_2^+$, $Y^-$-(L)$_k$-$F'_0$, in which $F'_0$ represents a different function from $F_0$, and on the other hand the molecule G, according to one of the following reaction diagrams:

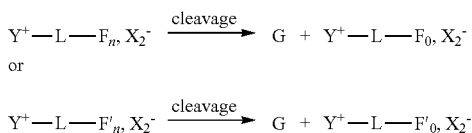

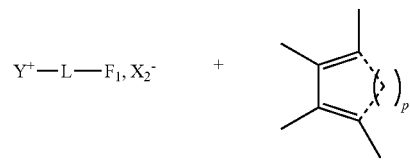

The use of the ionic liquids in such a reaction chain has the following advantages:

- the reactions are carried out in solution, and therefore all the analysis techniques, including $^1H$, $^{13}C$, $^{19}F$, $^{31}P$, $^{11}B$, $^{15}N$ NMR etc., HPLC, FTIR, UV, visible, fluorescence, electrochemical techniques, electrophoresis, mass spectrometry etc., can be used under normal conditions without particular complications;
- the reactions are carried out at the usual concentrations of 0.5 to 1 mole per liter (or even more), which represents a huge advantage in terms of specific load;
- recycling of the functionalized salt solution is easy;
- the solutions are easily transferable using syringe and (or) pumping techniques;
- synthesis of the ionic liquids and the functionalized salts is very simple and certain of these are commercially available;
- an immense variety of ionic liquids and functionalized salts is easily accessible;
- the solutions readily lend themselves to partition techniques and therefore to parallel or combinatorial synthesis techniques, which makes it possible to access product libraries;
- novel reactivities and selectivities have been observed in these media;
- scaling up does not pose any problems different from those observed during operations in the usual solvents;
- a parallel is easily established between this novel technology and solid-support synthesis and soluble-polymers synthesis techniques. It is immediately and obviously deduced that the salts functionalized identically to Wang, Rink, silylalkyl, carbonate, carboxylic, formyl, hydroxy, amino, oxime resins etc. can be used much more readily and advantageously.

The present invention relates to the use as defined above, for implementation of the Diels-Alder reaction, according to one of the following reaction diagrams:

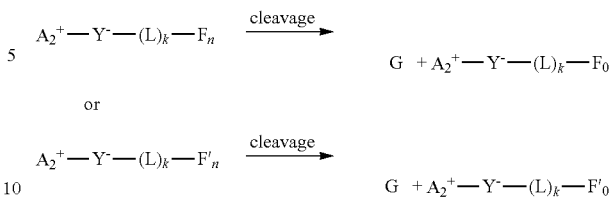

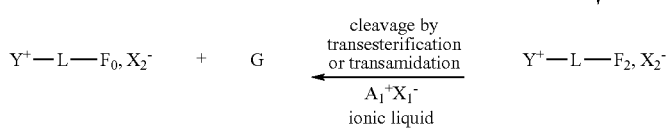

p being an integer varying from 0 to 2,

Y$^+$— representing an onium cation as defined above, and preferably being a trimethylalkylammonium, triethylalkylammonium or tributylalkylphosphonium cation, L representing an arm, in particular a linear or branched alkyl group comprising 1 to 20 carbon atoms, or an optionally functional aralkyl group, comprising 6 to 30 carbon atoms, and preferably being a linear alkyl group preferably a linear alkyl group of $(CH_2)_r$ type, r varying from 1 to 20, and preferably from 3 to 6, $X_2^-$ being as defined above, and being in particular $NTf_2^-$, $BF_4^-$, $PF_6^-$, $Cl^-$, $Br^-$, $CH_3COO^-$, $CF_3CO_2^-$, $CF_3SO_3^-$, $BR_4^-$, R being as defined above, the $A_1^+X_1^-$ ionic liquid being in particular in the form:

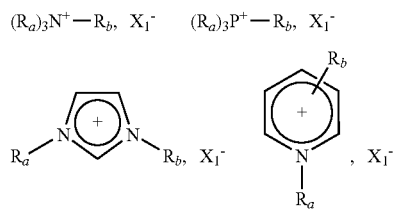

$R_a$ and $R_b$ being as defined above, and preferably representing alkyl groups comprising 1 to 20 carbon atoms, $X_1^-$ being chosen from: $BF_4^-$, $PF_6^-$, $NTf_2^-$, $Cl^-$, $Br^-$, $CH_3COO^-$, $CF_3CO_2^-$, $CF_3SO_3^-$, $BR_4^-$, R being as defined above, the functions $F_0$, $F_1$ and $F_2$ being as defined below:

$F_0$ corresponds to a -$\chi_1$H group, in which $\chi_1$ represents an oxygen atom or an —$NR_f$ group, $R_f$ corresponding to a linear or branched alkyl group, comprising 1 to 20 carbon atoms, or an aryl group comprising 6 to 30 carbon atoms, $F_1$ corresponds to the following formula:

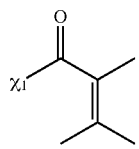

$\chi_1$ being as defined above, $F_2$ corresponds to the following formula:

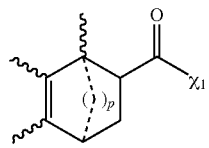

$\chi_1$ being as defined above,

G corresponding to the following formula:

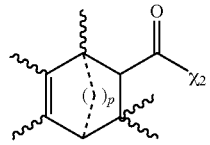

in which $\chi_2$ represents either an $OR_g$ group, $R_g$ representing a hydrogen atom or an alkyl group comprising 1 to 20 carbon atoms, or an —$NR_hR_u$ group, $R_h$ and $R_u$ representing independently of one another a hydrogen atom, an alkyl group comprising 1 to 20 carbon atoms or an aryl group comprising 6 to 30 carbon atoms,

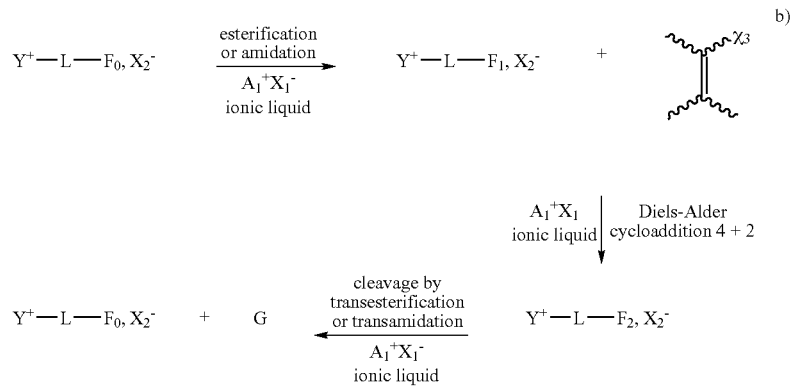

b)

$Y^+$—, L, $X_2^-$ and the $A_1^+X_1^-$ ionic liquid being as previously defined, the functions $F_0$, $F_1$ and $F_2$ being as defined below:

$F_0$ represents any function making it possible to attach a 1,3-diene, and is in particular chosen from the carbonyl, amine, alkoxy, silane, stannane and borane functions, comprising 1 to 20 carbon atoms, $F_1$ corresponds to the following formula:

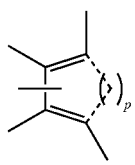

p being an integer varying from 0 to 2, $F_2$ corresponds to the following formula:

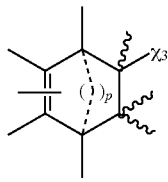

$\chi_3$ representing an electroattractive group, in particular chosen from the cyano, alkoxycarbonyl groups, comprising 1 to 20 carbon atoms, acyl group comprising 2 to 20 carbon atoms, benzoyl, sulphonyl, dialkoxyphosphonyl groups comprising 1 to 10 carbon atoms, G corresponding to the following formula:

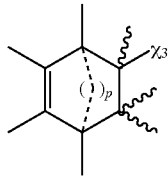

$\chi_3$ being as defined above.

The present invention also relates to the use as defined above, for implementation of Heck's reaction, according to the following reaction diagram:

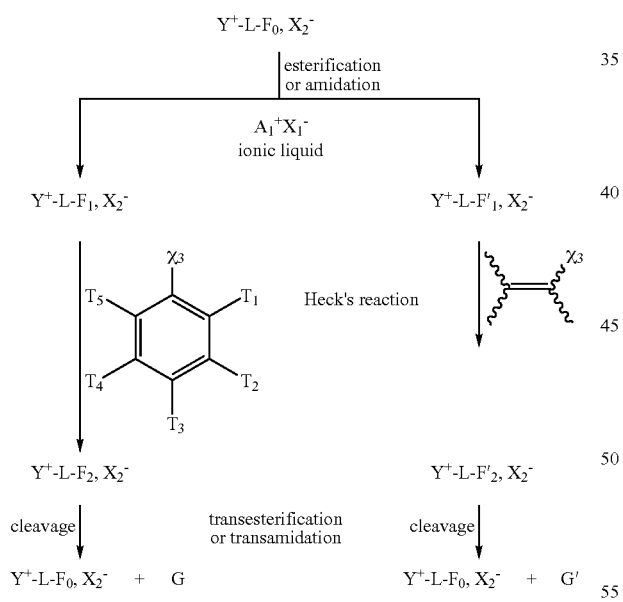

$Y^+$— representing an onium cation as defined above, and preferably being a trimethylalkylammonium, triethylalkylammonium or tributylalkylphosphonium cation, L representing an arm, in particular a linear or branched alkyl group comprising 1 to 20 carbon atoms, or an optionally functional aralkyl group comprising 1 to 20 carbon atoms, and preferably being a linear alkyl group preferably a linear alkyl group of type $(CH_2)_r$, r varying from 1 to 20, and preferably of 3 to 6, $X_2^-$ being as defined above, and being in particular $BF_4^-$, $PF_6^-$, $NTf_2^-$, $CF_3SO_3^-$, $Cl^-$, $Br^-$, or $I^-$, the ionic liquid $A_1^+X_1^-$ being in particular in the form:

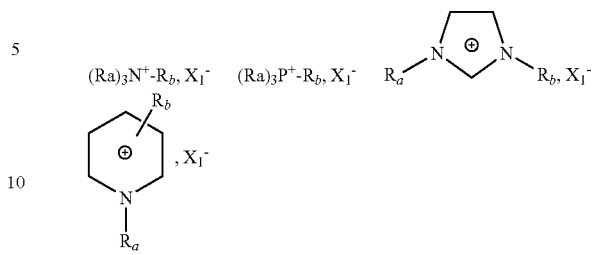

$R_a$ and $R_b$ being as defined above, and preferably representing alkyl groups comprising 1 to 20 carbon atoms, $X_1^-$ being chosen from: $BF_4^-$, $PF_6^-$, $NTf_2^-$, $Cl^-$, $Br^-$, $CH_3COO^-$, $CF_3CO_2^-$, $CF_3SO_3^-$, $BR_4^-$, R being as defined above, the functions $F_0$, $F_1$, $F'_1$, $F_2$ and $F'_2$ being as defined below:

$F_0$ corresponds to a $-\chi_1 H$ group, in which $\chi_1$ represents an oxygen atom or a $-NR_f$ group, $R_f$ corresponding to a linear or branched alkyl group, comprising 1 to 20 carbon atoms, or an aryl group comprising 6 to 30 carbon atoms, $F_1$ corresponds to the following formula:

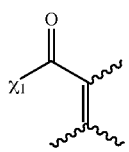

$\chi_1$ being as defined above, $F_2$ corresponds to the following formula:

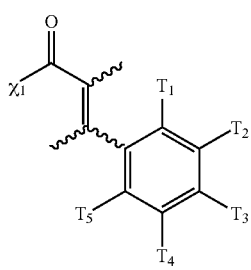

$\chi_1$ being as defined above,

G corresponding to the following formula:

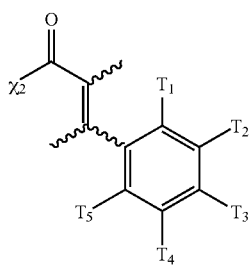

in which $\chi_2$ represents either an —$OR_g$ group, $R_g$ representing a hydrogen atom or an alkyl group comprising 1 to 20 carbon atoms, or an —$NR_hR_u$ group, $R_h$ and $R_u$ representing independently of one another a hydrogen atom, an alkyl group comprising 1 to 20 carbon atoms or an aryl group comprising 6 to 30 carbon atoms, $\chi_3$ representing a leaving group, in particular chosen from the halides I, Cl and Br, the mesylate, tosylate, triflate, sulphonate, sulphate or phosphate groups, $T_1$, $T_2$, $T_3$, $T_4$ and $T_5$ representing independently of one another a hydrogen atom, a linear or branched alkyl group, comprising 1 to 20 carbon atoms or an aryl group comprising 6 to 30 carbon atoms, or a functional group in particular chosen from $NO_2$, CN, COOR, OR, COR, NHCOR, NRR", $SO_2R$, I, Br, R and R" representing independently of one another an alkyl group comprising 1 to 20 carbon atoms or an aryl group comprising 6 to 30 carbon atoms, the entity

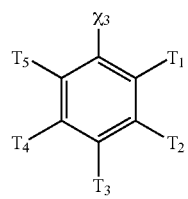

representing in particular the following groups:

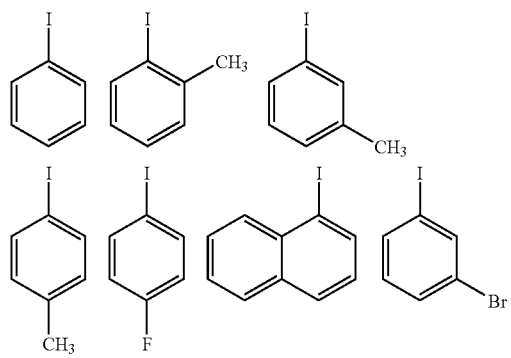

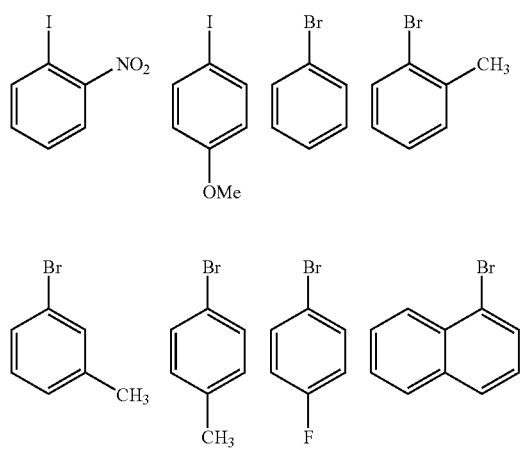

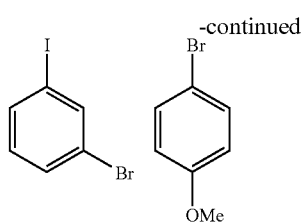

$F'''_1$ corresponds to the following formula:

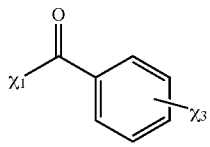

$\chi_1$ and $\chi_3$ being as defined above, $F'_2$ corresponds to the following formula:

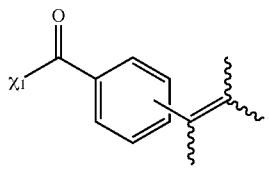

$\chi_1$ being as defined above,

G' corresponding to the following formula:

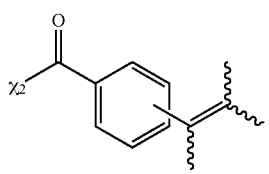

$\chi_2$ being as defined above.

The present invention relates to the use as defined above, for implementation of the Baylis-Hillman reaction, according to the following reaction diagram:

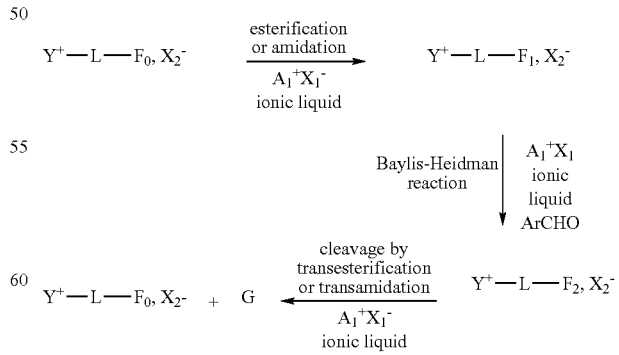

$Y^+$— representing an onium cation as defined above, and preferably being a trimethylalkylammonium, triethylalkylammonium or tributylalkylphosphonium cation, L representing an arm, in particular a linear or branched alkyl group comprising 1 to 20 carbon atoms, or an optionally functional aralkyl group, comprising 6 to 30 carbon atoms, and preferably being a linear alkyl group preferably a linear alkyl group of $(CH_2)_r$ type, r varying from 1 to 20, and preferably from 3 to 6, $X_2^-$ being as defined above, and being in particular $BF_4^-$, $PF_6^-$, $NTf_2^-$, $CF_3SO_3^-$, $Cl^-$, $Br^-$, $I^-$, $CH_3CO_2^-$ or $CF_3CO_2^-$, the $A_1^+X_1^-$ ionic liquid being in particular in the form:

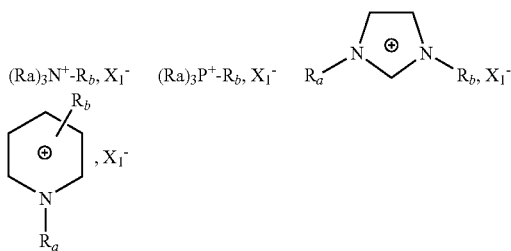

$R_a$ and $R_b$ being as defined above, and preferably representing alkyl groups comprising 1 to 20 carbon atoms, $X_1^-$ being chosen from: $BF_4^-$, $PF_6^-$, $NTf_2^-$, $Cl^-$, $Br^-$, $CH_3COO^-$, $CF_3CO_2^-$, $CF_3SO_3^-$, $BR_4^-$, R being as defined above, the functions $F_0$, $F_1$ and $F_2$ being as defined below:

$F_0$ represents an —OH group, $F_1$ corresponds to the following formula:

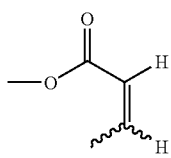

$F_2$ corresponds to the following formula:

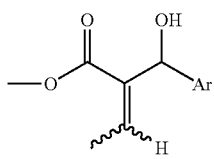

G corresponding to the following formula:

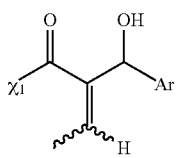

$\chi_1$ representing an —OH group, or an —$OR_g$ group, $R_g$ representing a linear or branched alkyl group, comprising 1 to 20 carbon atoms, Ar representing a substituted or non-substituted, aromatic or heteroaromatic group ArCHO being in particular chosen from:

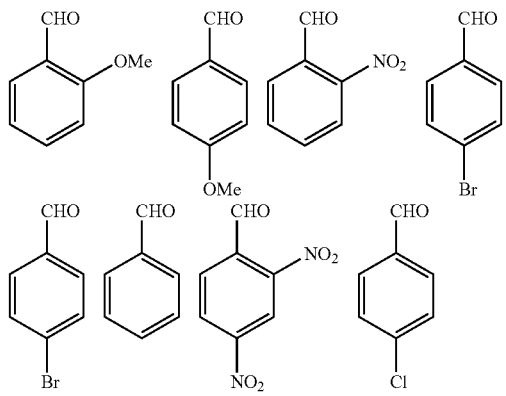

The present invention relates to use as defined above, for implementation of Suzuki coupling, according to one of the following reaction diagrams:

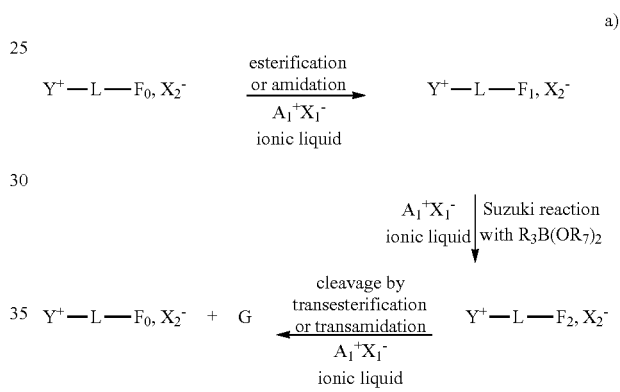

$R_3$ being chosen from the substituted or non-substituted aryl, heteroaryl, ethenyl, dienyl, allyl, ethynyl groups, comprising 2 to 30 carbon atoms, $R_7$ represents a branched or linear alkyl group or a cycloalkyl group comprising 1 to 12 carbon atoms, $Y^+$— representing an onium cation as defined above, and preferably being a trimethylalkylammonium, triethylalkylammonium or tributylalkylphosphonium cation, L representing an arm, in particular a linear or branched alkyl group comprising 1 to 20 carbon atoms, or an optionally functional aralkyl group comprising 6 to 30 carbon atoms, and preferably being a linear alkyl group, preferably a linear alkyl group of $(CH_2)_r$ type, r varying from 2 to 20, and preferably from 3 to 6, $X_2^-$ being as defined above, and being in particular $NTf_2^-$, $BF_4^-$, $PF_6^-$, $Cl^-$, $Br^-$, $CH_3COO^-$, $CF_3CO_2^-$, $CF_3SO_3^-$, $BR_4^-$, R being as defined above, the $A_1^+X_1^-$ ionic liquid being in particular in the form:

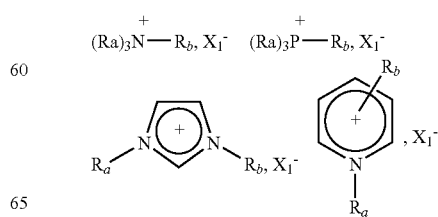

$R_a$ and $R_b$ being as defined above, and preferably representing alkyl groups comprising 1 to 20 carbon atoms, $X_1^-$ being chosen from: $BF_4^-$, $PF_6^-$, $NTf_2^-$, $Cl^-$, $Br^-$, $CH_3COO^-$, $CF_3CO_2^-$, $CF_3SO_3^-$, $BR_4^-$, R being as defined above, the functions $F_0$, $F_1$ and $F_2$ being as defined below:

$F_0$ is in the form $-\chi_1 H$, $\chi_1$ representing an oxygen atom or an $-NR_f$ group, $R_f$ corresponding to a linear or branched alkyl group, comprising 1 to 20 carbon atoms, or an aryl group comprising 6 to 30 carbon atoms, $F_1$ is in the form $-R_e-\chi$, $R_e$ representing an aromatic or heteroaromatic group comprising 6 to 30 carbon atoms, $\chi$ representing a leaving group preferably chosen from Cl, Br, I, OTf, $O-CO_2R^5$ or $OSO_3-R^5$, $R^5$ representing an alkyl group comprising 1 to 10 carbon atoms or an aralkyl group comprising 6 to 30 carbon atoms, $F_1$ preferably corresponding to the following formula:

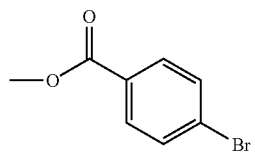

$F_2$ is in the form $-R_e-R_2$, $R_e$ being as defined above and $R_2$ being chosen from the substituted or non-substituted aryl, heteroaryl, ethenyl, dienyl, allyl, ethynyl groups, comprising 2 to 30 carbon atoms, $F_2$ preferably corresponding to the following formula:

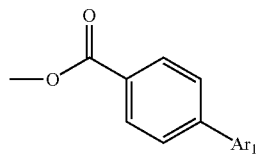

$Ar_1$ representing an aromatic group preferably chosen from:

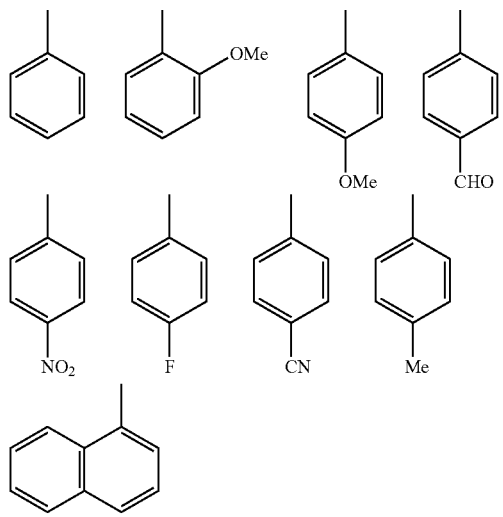

the G molecule being in the form $R_2-R_3$, $R_2$ and $R_3$ being as defined above, and corresponds in particular to the following formula:

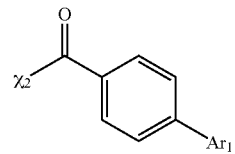

in which $\chi_2$ represents either an $-OR_g$ group, $R_g$ representing a hydrogen atom or an alkyl group comprising 1 to 20 carbon atoms, or an $-NR_hR_u$ group, $R_h$ and $R_u$ representing independently of one another a hydrogen atom, an alkyl group comprising 1 to 20 carbon atoms or an aryl group comprising 6 to 30 carbon atoms, $Ar_1$ is as defined above, b)

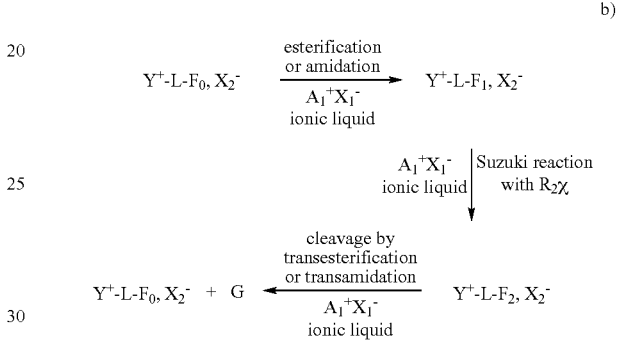

$Y^+-$, L, $X_2^-$, $A_1^+X_1^-$ and $R_2$ being as defined above, the functions $F_0$, $F_1$ and $F_2$ being as defined below:

$F_0$ is in the form $-\chi_1 H$, $\chi_1$ being as defined above, $F_1$ is in the form $-R_q-B(OR_7)_2$, $R_7$ being as defined above, and $R_q$ corresponding to a substituted or non-substituted aryl group comprising 6 to 30 carbon atoms, heteroaryl group comprising 4 to 20 carbon atoms, ethenyl group comprising 2 to 20 carbon atoms, dienyl group comprising 3 to 20 carbon atoms, allyl group comprising 3 to 20 carbon atoms, ethynyl group comprising 2 to 20 carbon atoms, $F_1$ preferably corresponding to the following formula:

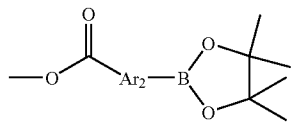

$Ar_2$ corresponding to a substituted or non-substituted aryl group comprising 6 to 30 carbon atoms, $F_2$ is in the form $-R_q-R_e$, $R_q$ and $R_e$ being as defined above, $F_2$ preferably corresponding to the following formula:

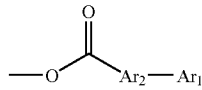

$Ar_1$ representing an aromatic group preferably chosen from:

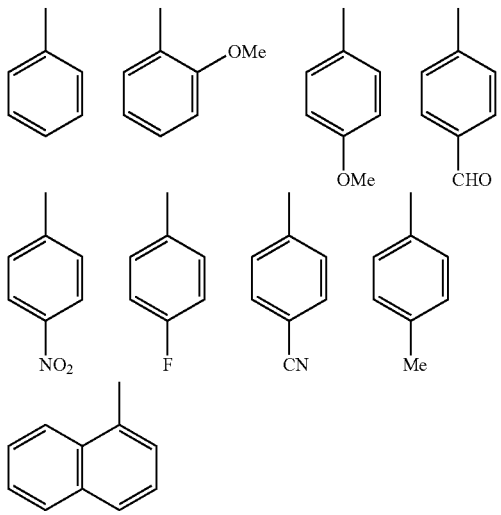

the G molecule being in the form $R_2$—$R_3$, $R_2$ and $R_3$ being as defined above, and corresponding in particular to the following formula:

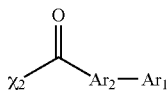

in which $\chi_2$, $Ar_1$ and $Ar_2$ are as defined above, c)

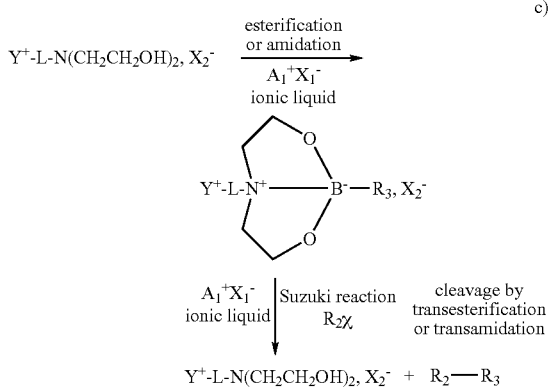

$Y^+$—, L, $X_2^-$, $A_1^+X_1^-$, $R_2$ and $R_3$ being as defined above, $R_3$ preferably being a phenyl group, d)

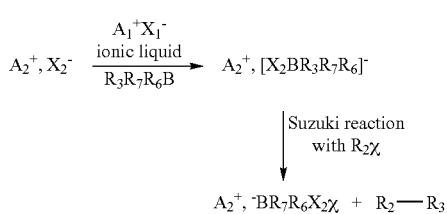

$A_2^+$ being an $(R_a)_3N^+R_b$ ammonium or $(R_a)_3P^+R_b$ phosphonium cation, preferably tetrabutylammonium and tetramethylammonium, $R_a$ and $R_b$ being as defined above, $X_2^-$ being in particular chosen from $OH^-$, $F^-$, $CN^-$, $R_sO^-$, $R_sS^-$, preferably $OH^-$ or $F^-$, $R_s$, representing an alkyl group comprising 1 to 20 carbon atoms or an aryl group comprising 6 to 30 carbon atoms, $R_3$ and $R_4$ being as defined above, $R_6$ and $R_7$ representing independently of one another an alkyl group comprising 1 to 20 carbon atoms or an aryl group comprising 6 to 30 carbon atoms, the boronic molecule of formula $R_3R_7R_6B$ being a trialkyl or aryl borane, the alkyl group comprising 1 to 20 carbon atoms and the aryl group comprising 6 to 30 carbon atoms, a boronic acid or ester, preferably a boronic acid or ester chosen as being phenyl boronic acid, $R_2$ and $\chi$ are as previously defined, $R_2\chi$ preferably corresponding to an aryl halide chosen from:

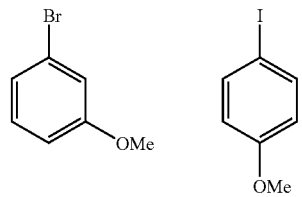 [SMILES: COc1cccc(Br)c1 ; COc1ccc(I)cc1]

The present invention also relates to the use as defined above, for the synthesis of libraries of molecules according to the parallel-synthesis technique, according to the following diagram:

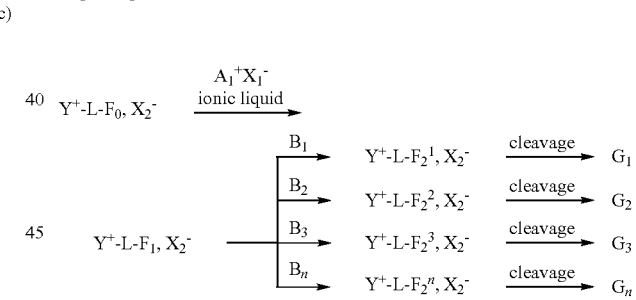

characterized in that the $Y^+$-L-$F_1$, $X_2^-$ functionalized salt in the $A_1^+$, $X_1^-$ ionic liquid is separated into n approximately equal parts, n varying from 2 to 1024, and in that each of these parts is then converted according to an organic-synthesis reaction, preferably a Heck or Suzuki coupling reaction, each using a different reagent $B_i$ in order to produce n solutions each containing a defined $Y^+$-L-$F_2^i$, $X_2^-$ compound, $F_2^i$ representing a function chosen from the functions as defined above, i varying from 1 to n, each solution being treated in order to release the $G_i$ molecules, i varying from 1 to n, which are each isolated and purified, constituting a molecule library.

The parallel-synthesis technique consists of preparing in parallel and simultaneously libraries of perfectly identified single products at a rate of one product per reactor or per well, after a sequence of reactions carried out with reagents specific to each prepared product.

The expression "approximately equal" designates partition into equal volumes, allowing for experimental errors.

The expression "molecule library" designates a set of products all identified, not mixed, each of them being arranged in its own container. This type of molecule library results from parallel synthesis. This expression can also designate a mixture of products identified by analysis techniques at the disposal of chemists and resulting from the reaction of a mixture of reagents with a single product or of a mixture of products with a single reagent according to the split-and-mix technique.

The present invention also relates to the use as defined above, for implementation of the synthesis of molecule libraries by the split-and-mix technique according to the following diagram:

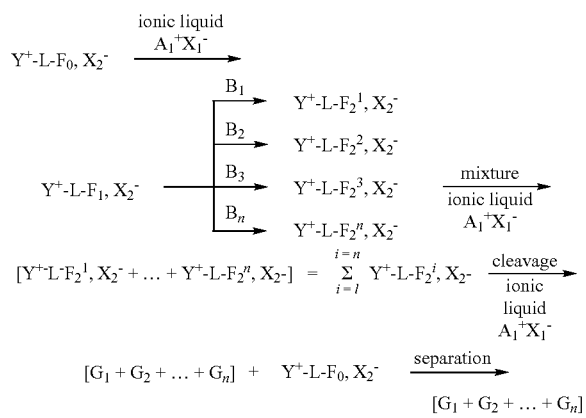

characterized in that:
- n fractions of the $Y^+$-L-$F_1$, $X_2^-$ solution, obtained from the starting $Y^+$-L-$F_0$, $X_2^-$ functionalized salt, in the $A_1^+X_1^-$ ionic liquid are converted in parallel according to an organic chemistry reaction, preferably a Heck or Suzuki coupling reaction, each using a different reagent $B_i$ in order to produce n solutions each containing a defined $Y^+$-L-$F_2^i$, $X_2^-$ compound, i varying from 1 to n, n varying from 2 to 1024, preferably from 2 to 96, $F_2^i$ representing a function chosen from the functions as defined above,
- the n solutions obtained in the preceding step are mixed in order to produce a solution in the $A_1^+X_1^-$ ionic liquid containing the n $Y^+$-L-$F_2^i$, $X_2^-$ products, i varying from 1 to n, annotated $$\sum_{i=1}^{i=n} Y^+ - L - F_2^i, X_2^-,$$

and this solution is subjected to a cleavage step, preferably a transesterification or a transamidation, in order to obtain in solution in the $A_1^+X_1^-$ ionic liquid, a mixture of the n $G_i$ molecules, i varying from 1 to n, and the starting $Y^+$-L-$F_0$, $X_2^-$ functionalized salt.
- the mixture as obtained in the preceding step is separated from the $A_1^+X_1^-$ ionic liquid and from the starting $Y^+$-L-$F_0$, $X_2^-$ functionalized salt by the usual separation methods, preferably by vacuum distillation, by extraction with a standard solvent such as heptane or toluene followed by evaporation of solvent, by chromatography on a column, plates or under pressure, in order to obtain a library containing n $G_i$ molecules, this sequence of steps mentioned above being possibly repeated j times, j being comprised between 2 and 10, in order to obtain j different libraries of n products.

The split-and-mix technique (O'Brecht et al., 1998) consists of reacting n fractions of a solution of a product, each with a different reagent leading to n novel products which are mixed after identification. This novel mixture is separated into m fractions which are then reacted in parallel each with a different reagent leading to m mixtures of n novel products, i.e. m×n products. These operations are repeated as many times as necessary.

According to an advantageous embodiment, the solution in the $A_1^+X_1^-$ ionic liquid containing the n $Y^+$-L-$F_2^i$, $X_2^-$ products, i varying from 1 to n, as obtained after the mixing stage, and annotated $$\sum_{i=1}^{i=n} Y^+ - L - F_2^i, X_2^-$$

is separated into m parts, m varying from 2 to 1024. Each of said parts is then treated respectively by a reagent $B'_j$, j varying from 2 to m, according to the following diagram:

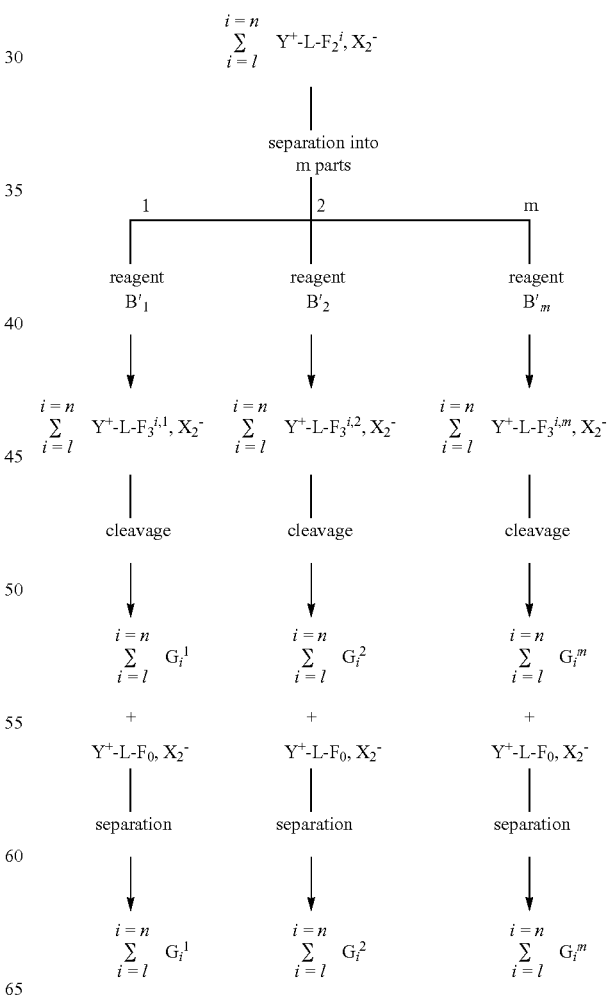

Thus, m novel $G_i^j$ libraries of n new products are obtained.

The upper spectrum corresponds to the spectrum of 7b in 0.85 M solution in $Me_3N-(CH_2)_2Me,NTf_2^-$. The lower spectrum is that of the reaction mixture once the Heck coupling is finished.

Figure 7:
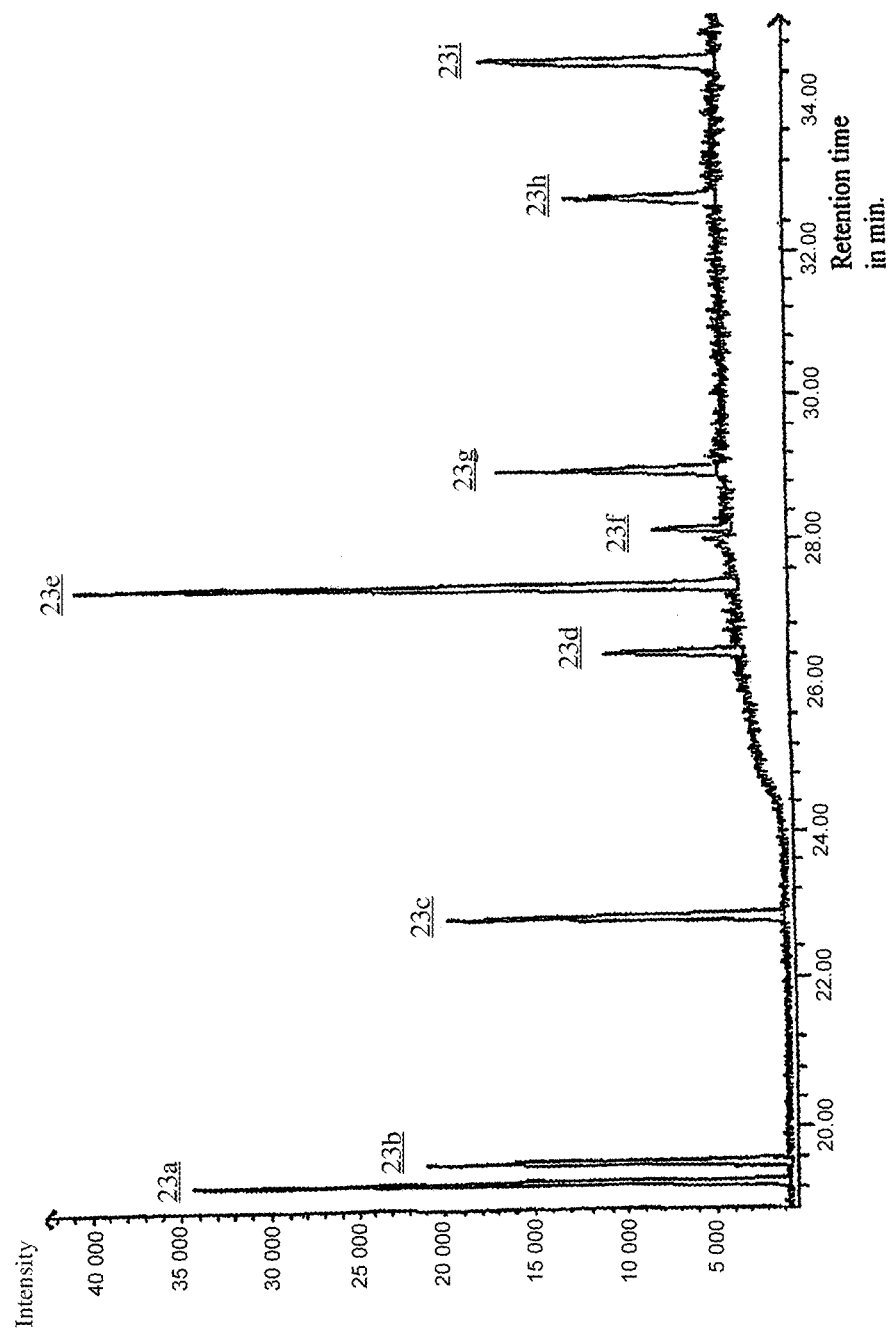

FIG. 7 represents a chromatogram corresponding to the mixture of the biaryl propyl esters 23a to 23i the mass spectra of which are described in Table XI.

Figure 8:
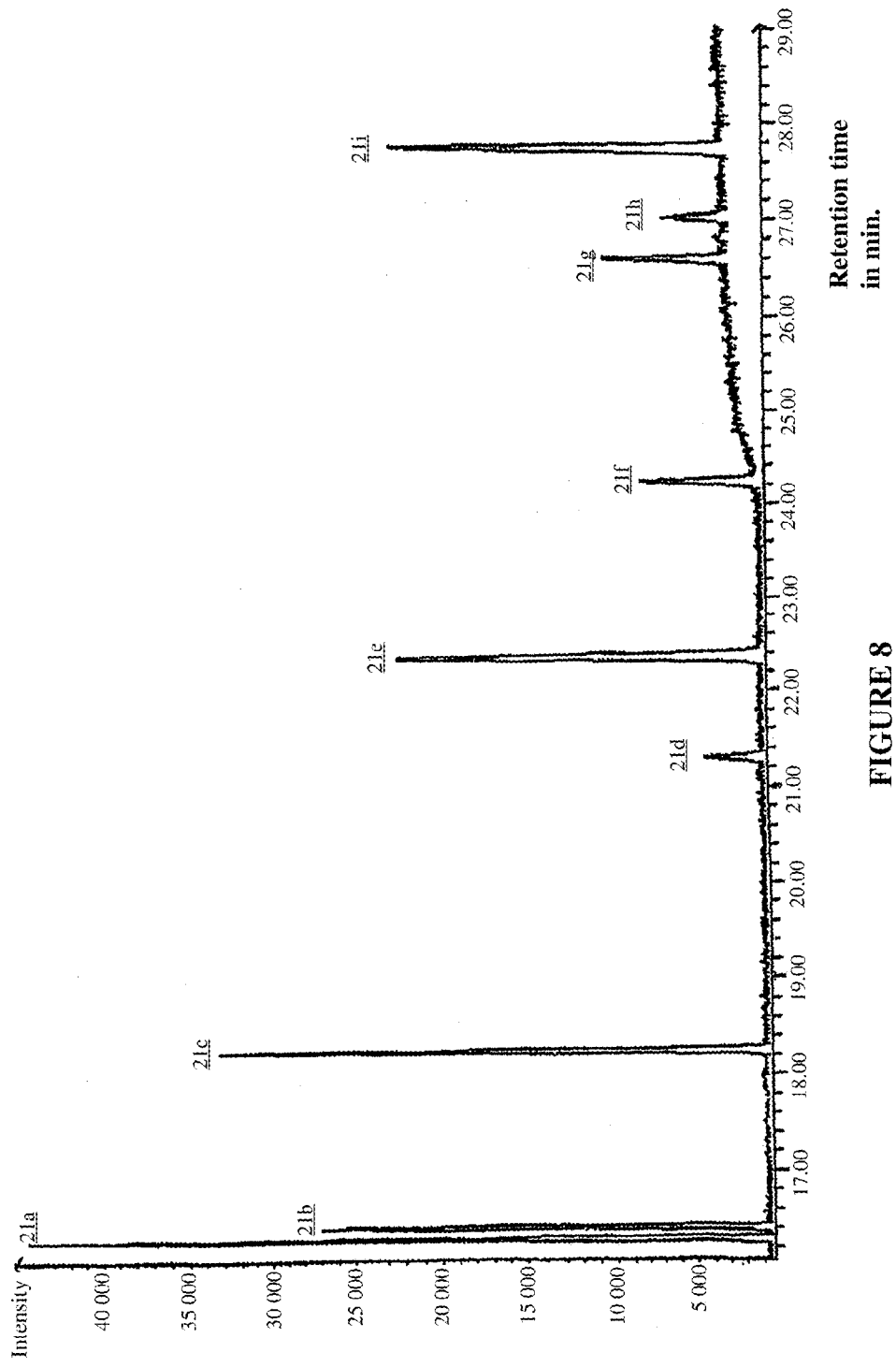

FIG. 8 represents a chromatogram corresponding to the mixture of the biaryl methyl esters of Table XII.

Figure 9:
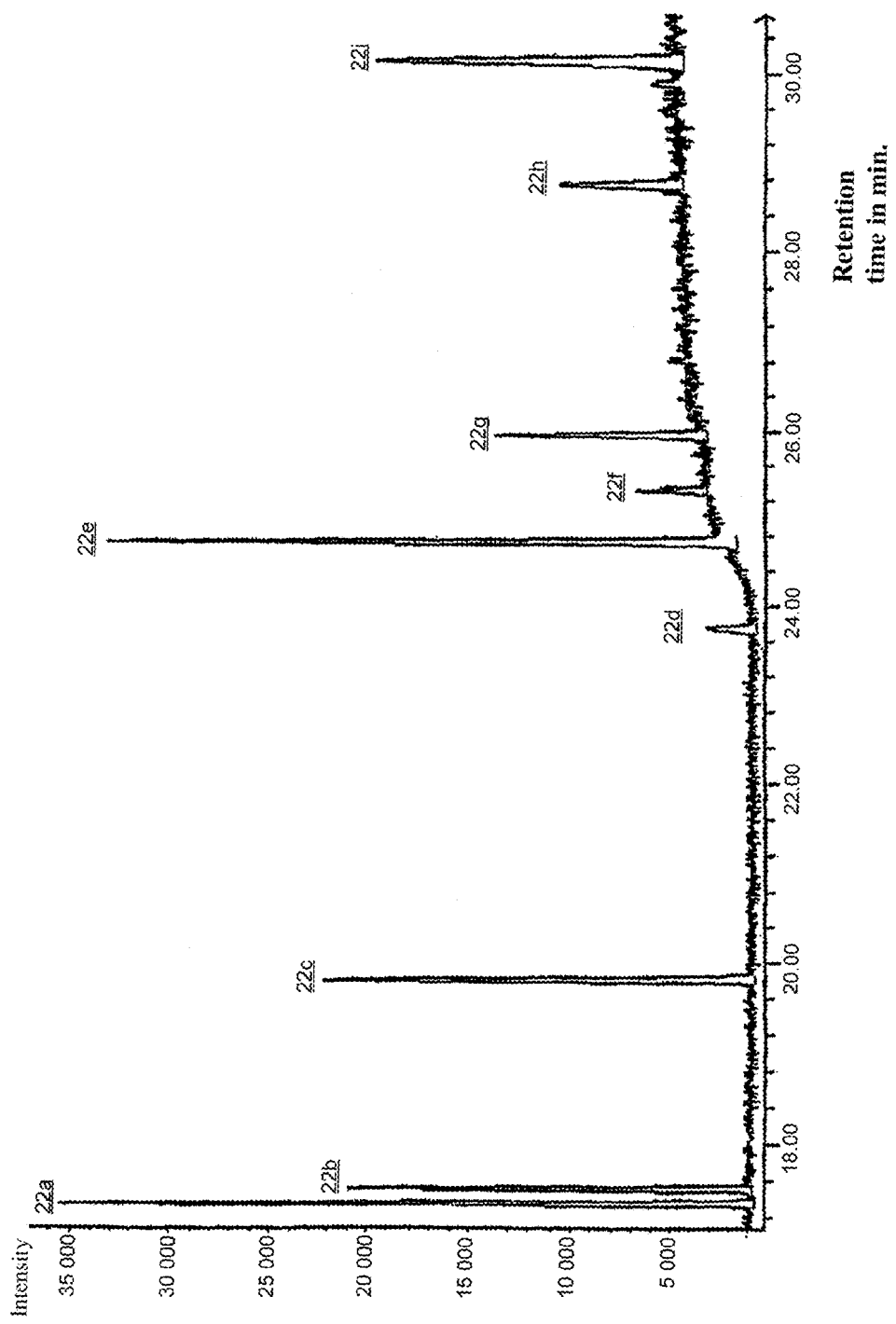

FIG. 9 represents a chromatogram corresponding to the mixture of the biaryl ethyl esters of Table XIII.

Figure 10:
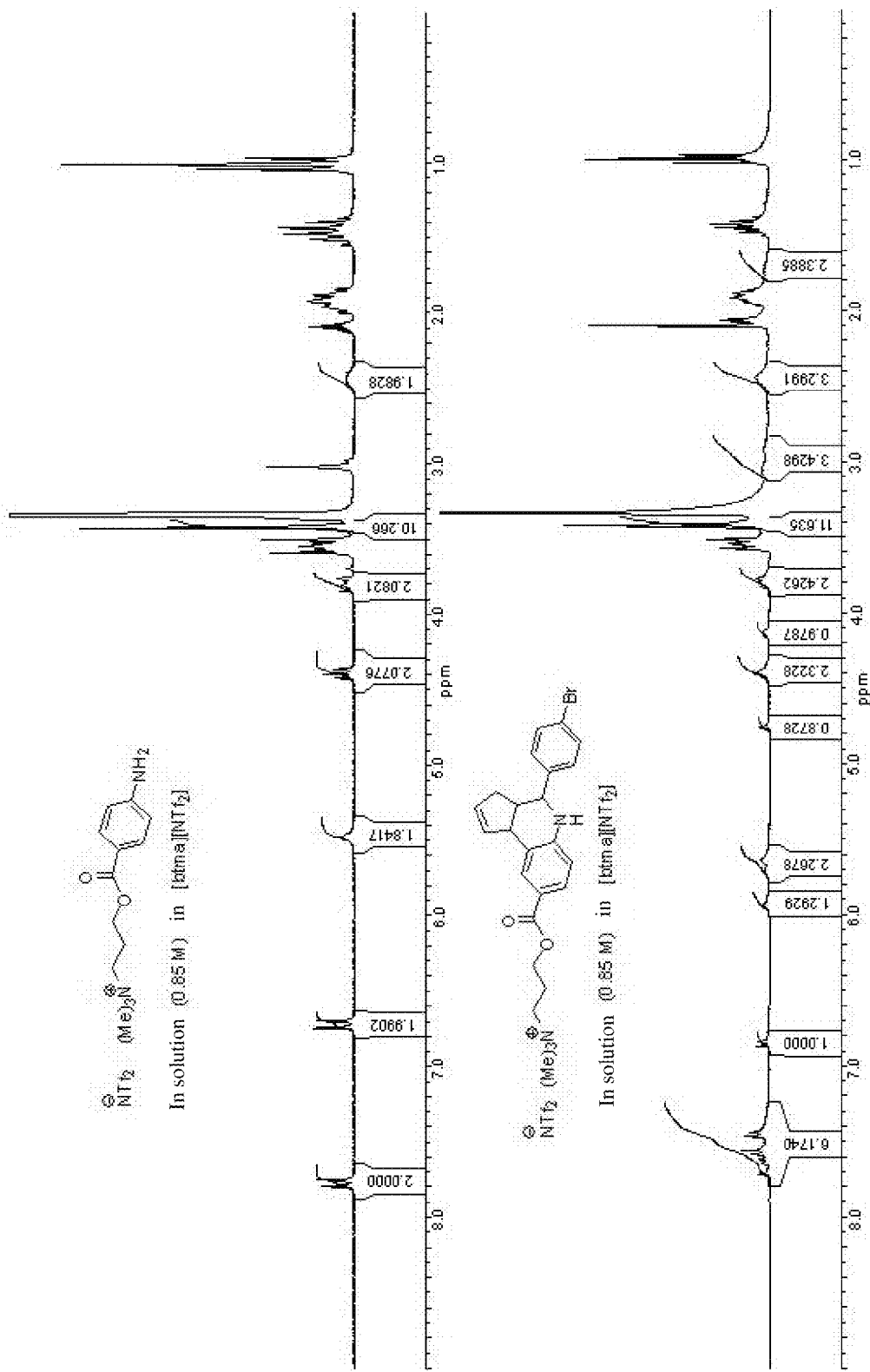

FIG. 10 represents proton NMR spectra recorded at 200 MHz in acetone D6, corresponding to monitoring of Grieco's reaction with supported aniline 1 and 4-nitrobenzaldehyde.

Figure 11:
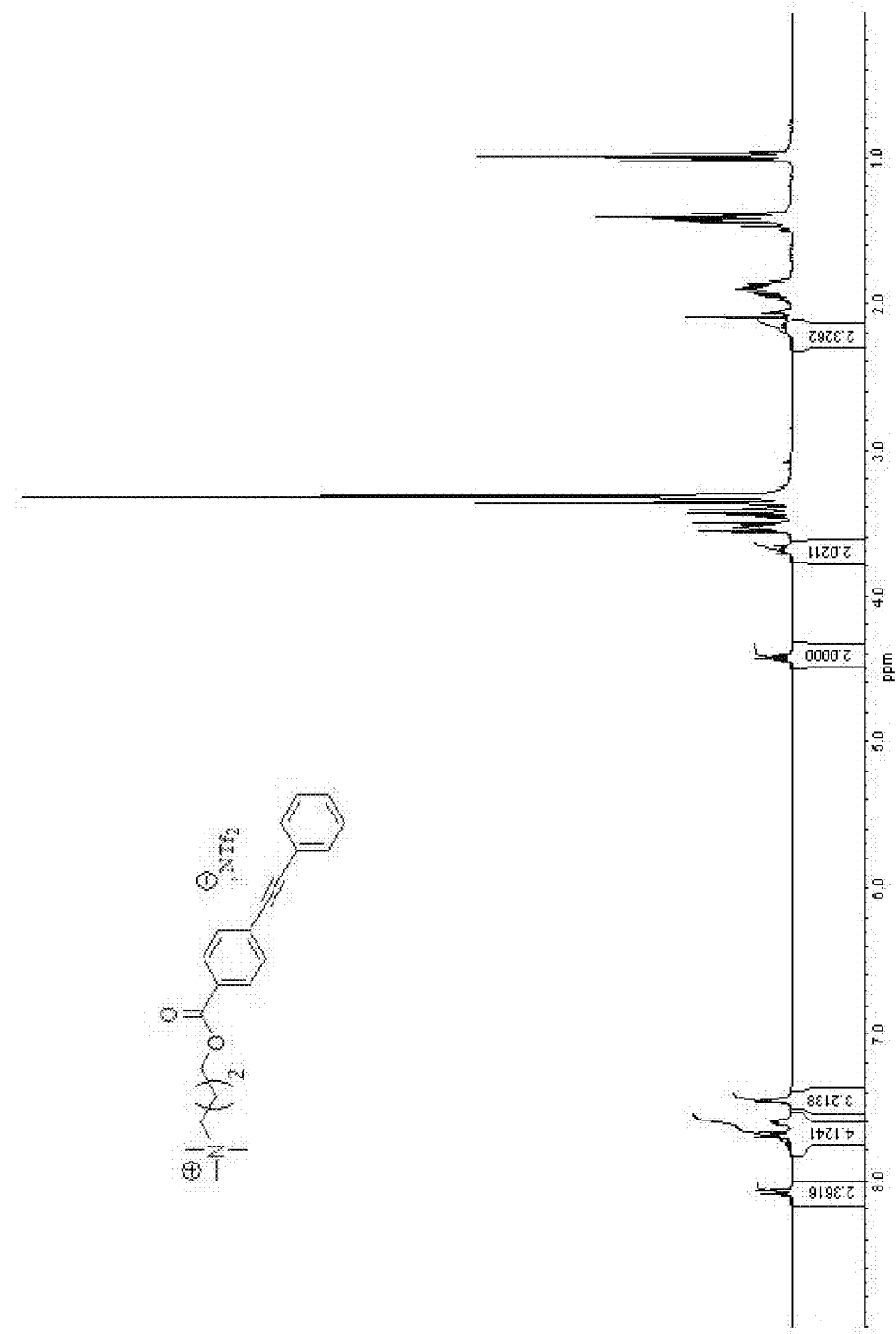

FIG. 11 represents proton NMR spectra recorded at 200 MHz in acetone D6, corresponding to monitoring of Sonogashira coupling with R=phenyl.

Figure 12:
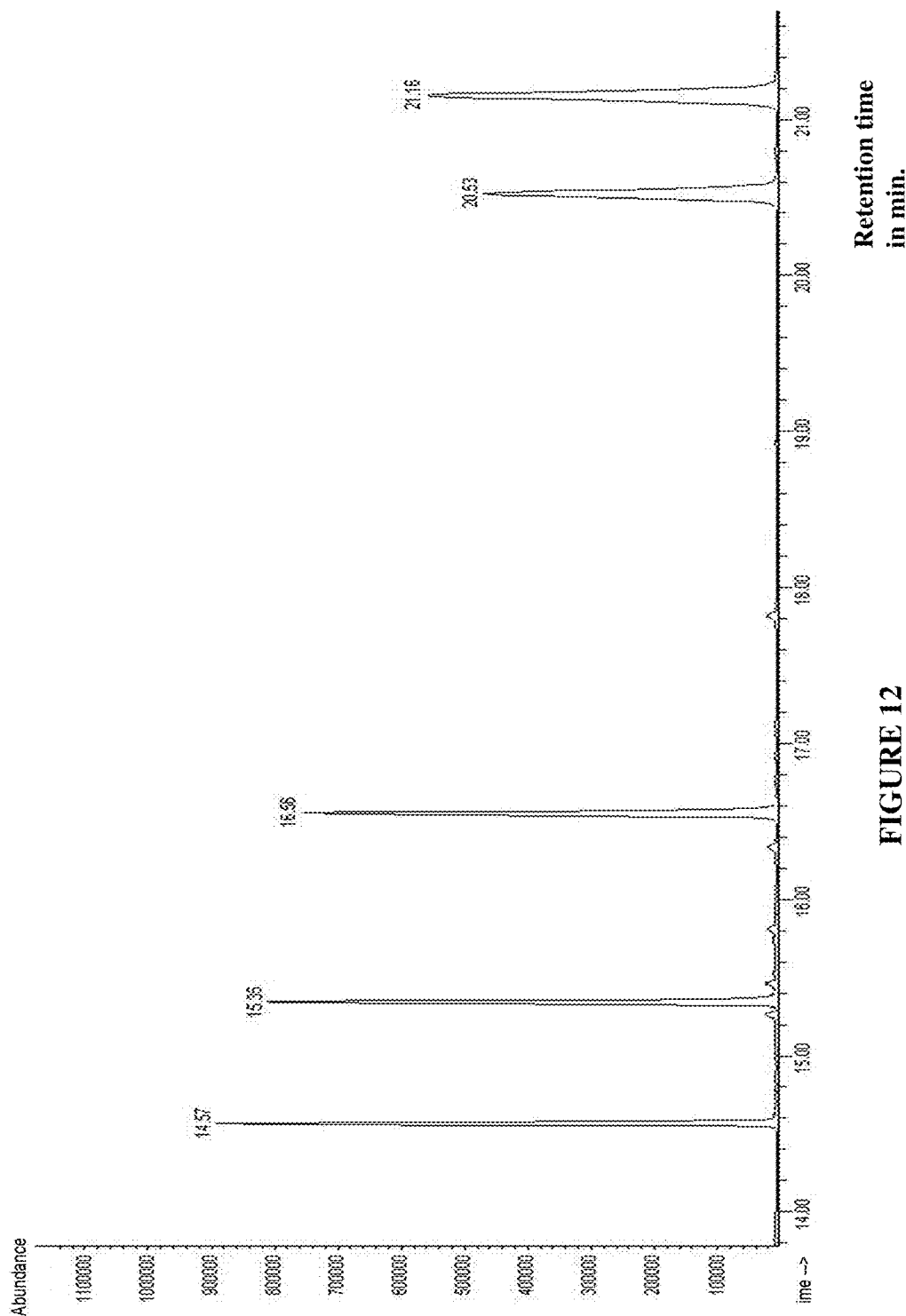

FIG. 12 represents a chromatogram corresponding to the mixture of the methyl esters the mass spectra of which are described in Table XX.

Figure 13:
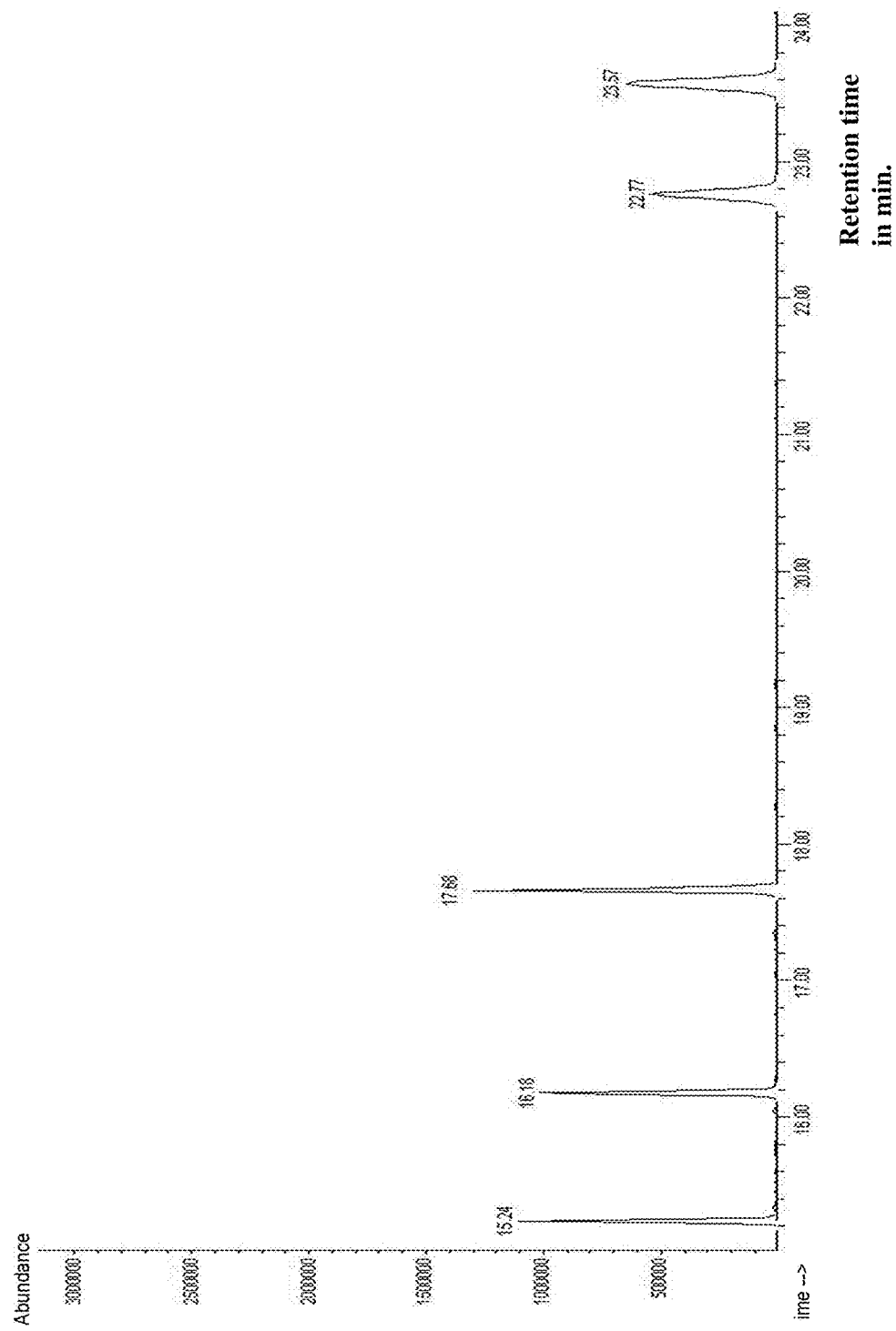

FIG. 13 represents a chromatogram corresponding to the mixture of the ethyl esters the mass spectra of which are described in Table XXI.

EXPERIMENTAL PART—PREPARATION OF THE COMPOUNDS

I) Synthesis of the Functionalized Salts

1/Alcohols 1:

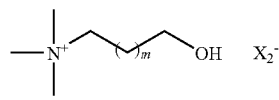

(1)

1a m=1; $X_2$=Cl
1b m=3; $X_2$=Cl
1c m=1; $X_2$=$PF_6$
1d m=1; $X_2$=$NTf_2$
1e m=3; $X_2$=$NTf_2$
1f m=1; $X_2$=$BF_4$

1a:

25 g (0.1 mol) of 3-chloropropanol, 30 ml of a 45% solution of trimethyl amine in water (0.2 mol) are introduced into a 250-ml flask, as well as 100 ml of acetonitrile in order to homogenize the medium. The mixture is then taken to reflux for 36 hours. The water/acetonitrile mixture is evaporated under vacuum and the white solid obtained is washed twice with 30 ml of ether.
White solid Yield=82% M.p.=158-160° C.
$^1$H NMR (200 MHz, $D_2O$): 1.80-2.05 (m, 2H); 3.00 (s, 9H); 3.20-3.41 (m, 2H); 3.60 (t, 2H, J=7.1 Hz)
$^{13}$C NMR (50 MHz, D2O): 25.68; 53.31 (t, $J_{C-N}$=4.1 Hz); 58.52; 64.52.

1b:

5 g (36 mmol) of 6-chlorohexanol, 10 ml of a 45% solution of trimethyl amine in water (0.1 mol) are introduced into a 250-ml flask as well as 100 ml of acetonitrile in order to homogenize the medium. The mixture is then taken to reflux for 36 hours. The water/acetonitrile mixture is evaporated under vacuum and the white solid obtained is washed twice with 30 ml of ether.
White solid Yield=62% M.p.=178-180° C.
$^1$H NMR (200 MHz, MeOH): 1.30-1.65 (m, 6H); 1.80-1.95 (m, 2H); 3.18 (s, 9H); 3.4-3.6 (m, 2H); 3.55 (t, 2H, J=6.1 Hz).
$^{13}$C NMR (50 MHz, MeOH): 22.93; 25.48; 26.15; 32.35; 52.60 (t, J=4.1 Hz); 61.67; 66.76.

1c:

A mixture of a solution of 10 g (65.3 mol) of N,N',N"-trimethyl-3-hydroxypropylammonium chloride in 15 ml of water and 13.23 ml (0.15 mol) of 60% hexafluorophosphoric acid in solution in water is stirred at ambient temperature for 2 hours. The medium immediately becomes heterogeneous and the formed precipitate is filtered and washed with ether. The white solid obtained is dried under vacuum.
White solid Yield=67% M.p.=124-126° C.
$^1$H NMR (200 MHz, $CD_3CN$): 1.70 (m, 2H); 2.82 (s, 9H); 3.15 (m, 2H); 3.40 (t, 2H, J=6.1 Hz).
$^{13}$C NMR (50 MHz, $CD_3CN$): 25.44; 52.59 (t, J=4.2 Hz); 57.67; 64.26 (t, J=3.8 Hz).

1d:

A solution of 10 g of ammonium salt (1a) (65.3 mmol) in 10 mL of water is prepared in a beaker. In another beaker, 20 g of lithium bis-trifluoromethanesulphonamide (71.9 mmol) is dissolved in the same manner. The two solutions are mixed and stirred for 2 hours at ambient temperature in order for the exchange to be complete. The two phases obtained are separated in a separating funnel, and the aqueous phase is extracted twice with 15 ml of methylene chloride. Finally, the solvent is evaporated and the product is dried under vacuum.
Colorless viscous oil Yield=86%
$^1$H NMR (200 MHz, Acetone $D_6$): 2.00-2.21 (m, 2H); 3.25 (s, 9H); 3.50-3.80 (m, 4H).
$^{13}$C NMR (50 MHz, Acetone $D_6$): 29.14; 54.27 (t; $J_{C-N}$=4.1 Hz); 60.05; 66.09; 121.05 (q, J=321.2 Hz).

1e:

A mixture of a solution of 10 g (51.2 mmol) of N,N',N"-trimethyl-4-hydroxybutylammonium chloride in 15 ml of water and 18.7 g (6.66 mmol) of lithium trifluoromethane sulphonamide is stirred at ambient temperature. The medium immediately becomes heterogeneous, and the two phases are separated in a separating funnel. The colorless oil obtained is then washed twice with 3 ml of water and dried at 50° C. under high vacuum.

Colorless oil Yield=93%.

$^1$H NMR (200 MHz, Acetone, D6): 1.41-1.60 (m, 6H); 1.88-2.01 (m, 2H); 3.30 (s, 9H); 3.50-3.65 (m, 4H); 3.55 (t, 2H, J=6.1 Hz).

$^{13}$C NMR (50 MHz, Acetone, D6): 23.02; 25.60; 26.22; 53.01 (t, J=4.1 Hz); 61.73; 66.99; 121.05 (q, J=324.2 Hz).

1f:

A mixture of a solution of 10 g (65 mmol) of N,N',N''-trimethyl-3-hydroxypropylammonium chloride in 15 ml of water and 9.1 ml (0.15 mol) of 50% tetrafluoroboric acid in water is stirred at ambient temperature. The medium remains homogeneous. After 12 hours, the water is evaporated to dryness, the white solid obtained is washed twice with 15 ml of anhydrous ether.

White solid Yield=92% M.p.=110-112° C.

$^1$H NMR (200 MHz, Acetone D$_6$): 2.10-2.241 (m, 2H); 3.05 (s, 9H); 3.24-3.45 (m, 4H); 3.61 (t, J=7.1 Hz, 2H).

$^{13}$C NMR (50 MHz, Acetone D$_6$): 27.52; 53.35 (t, J$_{C-N}$=4.1 Hz); 58.25.05 ??; 64.58.

2/Carboxylic Acid 2:

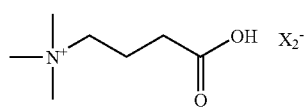

(2a)

2a X$_2$=Br
2b X$_2$=NTf$_2$

2a:

A mixture of 30 ml of a 6.65 molar aqueous solution (0.2 mol) and 14.3 ml (0.1 mol) of ethyl bromobutyrate is taken to reflux for 24 hours. The solvent is then evaporated to dryness and the white solid obtained is washed with 3 times 25 ml of ether.

The solid thus obtained is dissolved in 15 ml of a solution of hydrobromic acid (6 N), then taken to reflux for 12 hours, followed by evaporation to dryness. The solid obtained is washed in ether and then dried under vacuum.

White solid Yield=75% M.p.=188-190° C.

$^1$H NMR (200 MHz, CD$_3$OD): 1.95-2.21 (m, 2H); 2.49 (t, 2H, J=7.0 Hz); 3.25 (s, 9H); 3.45-3.55 (m, 2H).

$^{13}$C NMR (50 MHz, CD$_3$OD): 18.58; 30.04; 52.86 (t, J=4.1 Hz); 65.84 (t, J=4.1 Hz); 174.40.

2b:

4 g of N,N',N''-trimethyl-3-butanoic acid (2a) (17.7 mmol) is dissolved in 10 mL of water in a beaker. 5.6 g of LiNTf$_2$ (19.5 mmoles) is dissolved in the same manner in another beaker and the 2 solutions are mixed. The medium becomes cloudy and the appearance of 2 phases is observed. Stirring is maintained for 2 hours at ambient temperature in order for the exchange to be complete. The content of the beaker is decanted into a separating funnel and left to settle until there are 2 well-separated phases. The ionic liquid (lower phase) is extracted and the aqueous phase is washed twice with 20 ml of methylene chloride. Finally, the flask is placed under vacuum in order to dry the product after evaporation of the solvent.

Colorless viscous oil Yield=88%

$^1$H NMR (200 MHz, Acetone D$_6$): 2.15-2.30 (m, 2H); 2.5 (t, J=6.7 Hz, 2H); 3.40 (s, 9H); 3.55-3.70 (m, 2H)

$^{13}$C NMR (50 MHz, Acetone D$_6$): 19.52; 23.73; 54.09 (t, J$_{C-N}$=4.0 Hz); 67.02 (t, J$_{C-N}$=3.0 Hz); 118.4 (q$_{C-F}$, J=324.0 Hz); 172.89.

3/Halide 3:

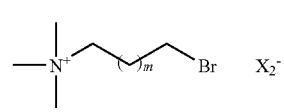

(3)

3a m=1; X$_2$=Br
3b m=3; X$_2$=Br
3c m=1; X$_2$=NTf$_2$
3d m=1; X$_2$=PF$_6$
3e m=3; X$_2$=PF$_6$
3f m=3; X$_2$=BF$_4$

1) X$_2$=Br:

41 ml (0.6 mol) of a 45% aqueous solution of trimethylamine is introduced into a 100-mL single-necked flask surmounted by a condenser. It is stirred and the oil bath is heated to a temperature of 40° C. At the condenser outlet, the trimethylamine vapors pass through a trap with KOH pellets in order to retain the traces of water present in the vapors and are bubbled through a two-necked flask containing 0.2 mole of dibromoalkane dissolved in 100 mL of anhydrous THF under stirring.

The contents of the flask are filtered and the solid is washed with ether. The white solid thus obtained is dried under vacuum.

3a:

White solid Yield=99% M.p.=212-215° C.

$^1$H NMR (20 0 MHz, CD$_3$OD): 2.31-2.59 (m, 2H); 3.32 (s, 9H); 3.52-3.69 (m, 4H)

$^{13}$C NMR (50 MHz, CD$_3$OD): 26.42; 28.96; 53.11 (t, J$_{C-N}$=4.0 Hz); 65.50 (t, J=3.6 Hz).

3b:

White solid Yield=96% M.p.=139-140° C.

$^1$H NMR (200 MHz, D$_2$O): 1.50-1.75 (m, 2H); 1.85-2.15 (m, 4H); 3.25 (s, 9H); 3.4-3.55 (m, 2H); 3.65 (t, J=6.6 Hz, 2H)

$^{13}$C NMR (50 MHz, D$_2$O): 21.91; 24.51; 31.72; 34.61; 53.22 (t, J$_{C-N}$=4.0 Hz); 66.80

2) X$_2$=NTf$_2$:

5.5 g of LiNTf$_2$ (19 mmoles) are dissolved in 10 mL of water in a beaker. In the same manner, approximately 17.3 mmoles of corresponding bromide is dissolved in water in another beaker. The two solutions are mixed and left under stirring for two hours.

The contents of the beaker are decanted into a separating funnel. The aqueous phase is extracted with twice 15 mL of methylene chloride. The organic phases are collected and dried over MgSO$_4$. The solvent is then evaporated to dryness and the product is dried under vacuum.

3c:

Colorless viscous oil Yield=84%.

$^1$H NMR (200 MHz, Acetone D$_6$): 1.40-1.70 (m, 2H); 1.90-2.20 (m, 4H); 3.35 (s, 9H); 3.50-3.70 (m, 4H)

$^{13}$C NMR (50 MHz, Acetone D$_6$): 23.13; 25.86; 33.24; 34.58; 54.06 (t, J$_{C-N}$=4.0 Hz); 67.65; 121.37 (q, J$_{C-F}$=320.9 Hz)

3) X$_2$=PF$_6$:

23 mmoles of the bromide is dissolved in 10 mL of water in a beaker, and 6 mL (68 mmol) of 60% HPF$_6$ in water is added. Stirring is maintained for 2 hours at ambient temperature in order for the exchange to be complete then the precipitate is filtered. The filtrate is then washed twice with 15 ml of methylene chloride. The solvent is evaporated to dryness and the solid obtained is added to the starting precipitate. Finally, the white solid obtained is washed with ether and dried under vacuum.

3d:
White powder Yield=88% M.p.=144-146° C.
$^1$H NMR (200 MHz, Acetone D$_6$): 2.1-2.5 (m, 2H); 3.05 (s, 9H); 3.4-3.6 (m, 4H)
$^{13}$C NMR (50 MHz, Acetone D$_6$): 27.29; 30.27; 54.27 (t, $J_{C-N}$=4.1 Hz); 66.54 (t, $J_{C-N}$=3.5 Hz)
$^{19}$F NMR (282 MHz, Acetone D$_6$): −71.65 (d, J=7.07 Hz)
$^{31}$P NMR spectrum (300 MHz, Acetone D$_6$): −142.69 (septuplet, J=708.2 Hz)
3e:
White solid Yield=97% M.p.=139-140° C.
$^1$H NMR (200 MHz, D$_2$O): 1.30-1.55 (m, 2H); 1.61-1.93 (m, 4H); 3.05 (s, 9H); 3.10-3.30 (m, 2H); 3.45 (t, J=6.7 Hz, 2H)
$^{13}$C NMR (50 MHz, D$_2$O): 21.89; 24.49; 31.69; 34.54; 53.18 (t, $J_{C-N}$=4.0 Hz); 66.78
$^{19}$F NMR (282 MHz, D$_2$O): −71.78 (d, J=703 Hz)
$^{31}$P NMR spectrum (300 MHz, D$_2$O): −144.38 (septuplet, J=703 Hz)
4) X$_2$=BF$_4$
5 g of bromide (3b)(17.3 mmol) is dissolved in 10 mL of water in a beaker. 2.1 mL (34.6 mmol) of a 50% solution of HBF$_4$ is added and stirring is maintained at ambient temperature for approximately 2 hours in order for the reaction to be complete. The contents of the beaker are decanted into a flask and the water is evaporated to dryness in a rotary evaporator, followed by finally drying under high vacuum.
3f:
Orange-colored viscous oil Yield=78%.
$^1$H NMR (200 MHz, D$_2$O): 1.31-1.53 (m, 2H); 1.60-1.94 (m, 4H); 3 (s, 9H); 3.15-3.32 (m, 2H); 3.45 (t, J=6.7 Hz, 2H)
$^{13}$C NMR (50 MHz, D$_2$O): 21.92; 24.55; 31.79; 34.85; 53.23 (t, $J_{C-N}$=3.5 Hz); 66.72 (t, $J_{C-N}$=3.02 Hz)

4/Amine 4:

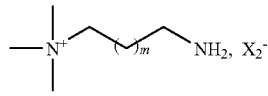

(4)

1) X$_2$=Br
10 mmol of bromide (3a or 3b) and 30 ml of a 25% aqueous solution of ammonium hydroxide are introduced into a 250-mL single-necked flask. A condenser is fitted and the reaction mixture is taken to reflux overnight (14 hours). The solution is left to cool down to ambient temperature, and 5 ml of a solution of NaOH (1 N) is added, then the water and the excess of ammonium hydroxide are evaporated to dryness.
The solid obtained is dissolved in acetone, filtered on MgSO$_4$, and evaporated to dryness. A white solid is obtained which is dried in a desiccator under vacuum in the presence of P$_2$O$_5$.
4a:
White solid Yield=82% M.p.=172-174° C.
$^1$H NMR (200 MHz, D$_2$O): 1.55-1.63 (m, 2H); 2.85 (t, J=6.5 Hz, 2H); 3.21 (s, 9H); 3.35-3.60 (m, 2H).
$^{13}$C NMR (50 MHz, D$_2$O): 27.95; 34.85; 52.65 (t, $J_{C-N}$=3.4 Hz); 63.58 (t, $J_{C-N}$=3 Hz).
4b:
White solid Yield=95% M.p.=132-134° C.
$^1$H NMR (200 MHz, D$_2$O): 1.30-1.52 (m, 2H); 1.64-1.90 (m, 4H); 3.07 (s, 9H); 3.15-3.33 (m, 2H); 3.45 (t, J=6.7 Hz, 2H)
$^{13}$C NMR (50 MHz, D$_2$O): 21.92; 24.55; 31.79; 34.85; 53.23 (t, $J_{C-N}$=3.5 Hz); 66.72 (t, $J_{C-N}$=3.0 Hz).

2) X$_2$=NTf$_2$:
5.5 g of LiNTf$_2$ (19 mmoles) is dissolved in 10 mL of water in a beaker. In the same manner, approximately 17.3 mmoles of corresponding ammonium bromide is dissolved in water in another beaker. The two solutions are mixed and left under stirring for two hours.
The contents of the beaker are decanted into a separating funnel and the aqueous phase is extracted with twice 15 mL of methylene chloride. The 2 organic phases are collected and dried over MgSO$_4$. The solvent is then evaporated to dryness and the product is dried under vacuum.
4c:
Viscous orange oil Yield=87%
$^1$H NMR (200 MHz, Acetone): 1.41-1.70 (m, 2H); 1.95-2.15 (m, 4H); 2.82 (broad s, 2H); 3.35 (s, 9H); 3.25-3.40 (m, 2H); 3.50-3.70 (m, 2H).
$^{13}$C NMR (50 MHz, Acetone): 23.02; 26.45; 30.79; 35.64; 53.56 (t, $J_{C-N}$=3.5 Hz); 67.82 (t, $J_{C-N}$=3.0 Hz); 121.65 (q, J=321 Hz)

5/Diethanolamine 5:

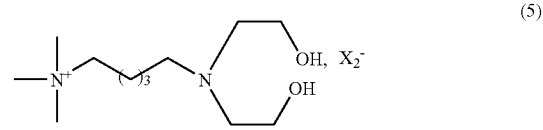

(5)

5a X$_2$=NTf$_2$
5b X$_2$=BF$_4$
5c X$_2$=PF$_6$ 10 g of the salt ((III) with X$_2$=Br and m=3), 40 mL of ethanol and 1 equivalent of diethanolamine are introduced into a 50-mL single-necked flask. A condenser is fitted and the reaction mixture is taken to 90° C. overnight (14 hours). The assembly is then cooled down to ambient temperature, and a solution of NaOH (1N) is added until a basic pH is reached. The (water/ethanol) mixture is then evaporated to dryness and the flask is placed under high vacuum until the water is completely eliminated. The white paste obtained is then washed with 3 times 30 ml of anhydrous acetone in order to extract the maximum amount of product. Finally, the solvent is evaporated to dryness.
5a:
Viscous orange oil Yield=91%.
$^1$H NMR (200 MHz, D$_2$O): 1.25-1.5 (m, 2H); 1.55-1.95 (m, 4H); 2.8-2.95 (m, 4H); 3.0 (t, J=5.8 Hz, 4H); 3.05 (s, 9H); 3.2-3.35 (m, 2H); 3.75 (t, J=5.7 Hz, 4H).
$^{13}$C NMR (50 MHz, D$_2$O): 21.26; 22.31; 23.17; 48.31; 51.86 (t, $J_{C-N}$=4.0 Hz); 52.83; 54.05; 56.60; 56.80; 65.53.
5b:
White paste Yield=91%.
$^1$H NMR (200 MHz, D$_2$O): 1.25-1.45 (m, 2H); 1.55-1.90 (m, 4H); 2.8-2.95 (m, 4H); 3.05 (s, 9H); 3.25 (t, J=8.7 Hz, 2H); 3.80 (t, J=5.8 Hz, 4H); 2.95-3.15 (m, 4H)
$^{13}$C NMR (50 MHz, D$_2$O): 22.41; 23.37; 23.93; 49.42; 53.15; 53.95; 55.22; 57.19; 57.53; 66.68.
$^{19}$F NMR (282 MHz, D$_2$O): −71.64 (d, $J_{P-F}$=707.6 Hz).
$^{31}$P NMR spectrum: (300 MHz, D$_2$O): −144.35.
5c:
Colorless viscous oil Yield=94%.
$^1$H NMR (200 MHz, D$_2$O): 1.25-1.65 (m, 4H); 1.67-1.95 (m, 4H); 3.05 (s, 9H); 3.15 (t, J=5.6 Hz, 4H); 3.2-3.3 (m, 4H); 3.4-3.5 (m, 2H); 3.8 (t, J=5.6 Hz, 4H)

$^{13}$C NMR (50 MHz, D$_2$O): 21.90; 22.32; 28.47; 31.75; 34.63; 49.29; 53.17 (t, J$_{C-N}$=4.0 Hz); 56.87; 66.58; 70.30.

$^{19}$F NMR (282 MHz, D$_2$O): −149.98 (t, J$_{B-F}$=1.13 Hz).

II) Functionalization of the Preceding Salts

A) Acrylic Ester 6:
General Procedure of Esterification by Acrylic Acid:

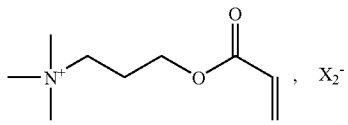

6a X$_2$=NTf$_2$
6b X$_2$=Cl
6c X$_2$=BF$_4$

A solution of N,N',N''-trimethyl-3-hydroxypropylammonium salt and 3 equivalents of acryloyl chloride in acetonitrile is stirred in the presence of 5 equivalents of solid K$_2$CO$_3$ for 2 hours at a temperature comprised between 18 and 22° C. The mixture is then filtered and placed under vacuum in order to eliminate the solvent and the excess of the reagent. The ammonium acrylate thus obtained is stable at 4° C. and can be stored for several months.

6a:
Colorless oil Yield=100%
$^1$H NMR (200 MHz, Acetone D$_6$): 2.22-2.25 (m, 2H); 3.25 (s, 9H); 3.60-3.75 (m, 2H); 4.15 (t, 2H, J=6.0 Hz); 5.80 (dd, 1H, J$_1$=1.92, J$_2$=10.68); 6.05 (dd, 1H, J$_1$=17.2, J$_2$=10.7); 6.15 (dd, 1H, J$_1$=1.9, J$_2$=17.2).
$^{13}$C NMR (50 MHz, Acetone D$_6$): 29.17; 54.16 (t, J=4.0); 65.16; 65.23; 121.05 (q, J$_{CF}$=374.2 Hz); 129.40; 132.15; 165.61
$^{19}$F NMR (282 MHz, Acetone D$_6$): −79.8
Mass spectrometry (FAB) for C$_9$H$_{18}$NO$_2$ (C$^+$)
Calculated theoretical mass 172.13375
Mass found: 172.1346

6b:
White solid Yield=100% M.p.=175-177° C.
$^1$H NMR (200 MHz, Acetone D$_6$): 2.15-2.20 (m, 2H); 3.15 (s, 9H); 3.48-3.52 (m, 2H); 4.18 (t, 2H, J=6.0 Hz); 5.75 (dd, 1H, J$_1$=1.92 Hz, J$_2$=10.5 Hz); 6.15 (dd, 1H, J$_1$=10.5 Hz, J$_2$=17.3 Hz); 6.15 (dd, 1H, J$_1$=1.9 Hz, J$_2$=17.3 Hz)
$^{13}$C NMR (50 MHz, Acetone D$_6$): 21.74; 52.23 (t, J=4.2 Hz); 60.44 (t, J=3.02); 62.6; 127.41; 130.65; 165.04

6c:
Colorless oil Yield=93%
$^1$H NMR (200 MHz, Acetone D$_6$): 2.28-3.31 (m, 2H); 3.32 (s, 9H); 3.06-3.15 (m, 2H); 4.52 (t, 2H, J=6.6 Hz); 5.80 (dd, 1H, J$_1$=1.9 Hz, J$_2$=10.0 Hz); 6.05 (dd, 1H, J$_1$=18.3 Hz, J$_2$=10.0 Hz); 6.15 (dd, 1H, J$_1$=1.9 Hz, J$_2$=18.3 Hz)
$^{13}$C NMR (50 MHz, Acetone D$_6$): 22.81; 53.28; 61.46; 63.83; 128.51; 131.72; 167.31.

B/3-Iodobenzoic Esters 7:

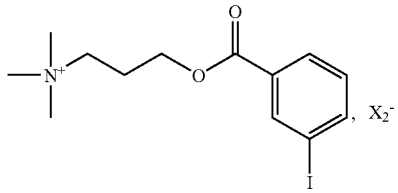

(7)

7a X$_2$=Cl
7b X$_2$=NTf$_2$

7a:
1.3 g (8.4 mmol) of N,N',N''-trimethyl-3-hydroxypropylammonium chloride, 10 ml of acetonitrile, 6.5 g of K$_2$CO$_3$ and 3 g of 3-iodobenzoic acid chloride are introduced into a 100-ml flask. After stirring overnight at ambient temperature, the reaction medium is filtered and K$_2$CO$_3$ is washed with 3 times 15 ml of methylene chloride. After evaporation of the latter, the product is isolated by filtration after crystallization from acetone. The white solid thus obtained is washed with 3×10 ml of ether in order to eliminate the remaining traces of acid.

White solid Yield=85% M.p.=180-182° C.
$^1$H NMR (200 MHz, D$_2$O): 2.15 (m, 2H); 3.01 (s, 9H); 3.25-3.45 (m, 2H); 4.10-4.20 (t, 2H, J=6.6 Hz); 7.05 (t, 1H, J=7.1 Hz); 7.75 (dd, 2H, J$_1$=7.1 Hz, J$_2$=2 Hz); 8.0 (d, 1H, J=2.0 Hz).
$^{13}$C NMR (50 MHz, D$_2$O): 22.56; 53.35 (t, J$_{C-N}$=4.1 Hz); 62.83; 64.15 (t, J$_{C-N}$=3.3 Hz); 93.87; 129.07; 130.72; 131.08; 138.31; 142.83; 166.91.

7b:
0.7 g (1.8 mmol) of the chloride (VII) with X$_2$=Cl) is solubilized in 5 ml of water in a 100-ml flask. 0.8 g (2.8 mmol) of LiNTf$_2$ in 3 ml of water is added to this solution. The reaction mixture is stirred for 2 hours at ambient temperature before extracting the product from the water with methylene chloride. After evaporation of the latter, a white solid is obtained.

White solid Yield=88% M.p.=78-80° C.
$^1$H NMR (200 MHz, Acetone D$_6$): 2.20-2.30 (m, 2H); 3.31 (s, 9H); 3.65-3.77 (m, 2H); 4.39 (t, 2H, J=6.7 Hz); 7.21 (t, 1H, J=7.1 Hz); 7.90 (dd, 2H, J$_1$=7.1 Hz, J$_2$=1.9 Hz); 8.22 (d, 1H, J=1.9 Hz)
$^{13}$C NMR (50 MHz, Acetone D$_6$): 23.97; 54.23 (t, J$_{C-N}$=4.1 Hz); 55.40; 63.27; 65.31 (t, J$_{C-N}$=3.3 Hz); 94.70; 121.17 (q, J$_{C-F}$=320.9 Hz); 130.11; 131.94; 133.29; 139.32; 143.37; 165.65
$^{19}$F NMR (282 MHz, Acetone D$_6$): −79.23
Mass spectrometry (FAB) for C$_{15}$H$_{19}$F$_6$N$_2$O$_6$S$_2$
Theoretical mass calculated for (2C$^+$,A): 976.0094
Mass found: 976.0094

C/4-Bromobenzoic Esters 8:

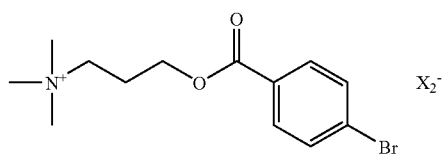

(8)

8a X$_2$=Cl
8b X$_2$=NTf$_2$
8c X$_2$=PF$_6$
8d X$_2$=BF$_4$

8a:
2 g (13.1 mmol) of N,N',N''-trimethyl-3-hydroxypropylammonium chloride, 25 ml of acetonitrile, 20 g of K$_2$CO$_3$ in powder and 4 g (17.5 mmol) of 4-bromobenzoic acid chloride are introduced into a 250-ml flask. After stirring overnight at ambient temperature, the reaction medium is filtered and K$_2$CO$_3$ is washed with 3 times 15 ml of methylene chloride and finally evaporated to dryness. After taking up in water the excess of the 4-bromobenzoic acid which crystallizes by filtration is eliminated. The product is then crystallized from acetone after evaporation of water.
White solid Yield=60% M.p.=164-166° C.

$^1$H NMR (200 MHz, D$_2$O): 2.21-2.34 (m, 2H); 3.12 (s, 9H); 3.30-3.58 (m, 2H); 4.35 (t, 2H, J=6.8 Hz); 7.57 (d, 2H, J=7.4 Hz); 7.80 (d, 2H, J=7.4 Hz)

$^{13}$C NMR (50 MHz, D$_2$O): 22.55; 30.61; 53.34 (t, J$_{C-N}$=4.2 Hz); 62.69; 64.41 (t, J$_{C-N}$=4.09 Hz); 128.34; 128.66; 131.37; 132.20; 167.84

Mass spectrometry (FAB) for C$_{11}$H$_{19}$NO$_2$Cl
Theoretical mass for (C$^+$): 302.0580
Mass found: 302.0585

8b:
In this case the synthesis of substrate was envisaged according to two approaches: by direct esterification of N,N,N-trimethyl-3-hydroxypropylammonium bis-trifluoromethanesulphonamide or by metathesis from the corresponding chloride.

Esterification:
4 g (10.5 mmol) of the alcohol, 20 ml of acetonitrile, 2 ml of a saturated solution of NaCO$_3$ in water and 4 g (17.5 mmol) of 4-bromobenzoic acid chloride are introduced into a 250-ml flask. The reaction mixture is heated at 60° C. overnight followed by evaporation to dryness, and the residue obtained is solubilized in methylene chloride. This solution is washed successively with 2×20 ml of water, 2×20 ml of a soda solution (1N) and finally with 2×20 ml of water. The solution is dried over magnesium sulphate and the solvent is evaporated to dryness. After taking up in acetone, the remaining traces of acids are eliminated by precipitation at 4° C. After evaporation of the latter, a pure white solid is obtained.
Yield=90%

Metathesis
1 g (2.98 mmol) of (8a) is solubilized in 5 ml of water in a 100-ml flask. 1.1 g (3.19 mmol) of lithium bis-trifluoromethanesulphonamide (LiNTf$_2$) in solution in 3 ml of water is added to this solution. The reaction mixture is stirred for 2 hours at ambient temperature before extracting our product with 20 ml of methylene chloride. After evaporation of the latter, a white solid is obtained which is dried under vacuum.

White solid Yield=90% M.p.=86-88° C.

$^1$H NMR (200 MHz, Acetone D$_6$): 2.64-2.83 (m, 2H); 3.59 (s, 9H); 3.96-4.06 (m, 2H); 4.71 (t, 2H, J=6.76 Hz); 7.90 (d, 2H, J=8.9 Hz); 8.19 (dd, 2H, J=8.9 Hz).

$^{13}$C NMR (50 MHz, Acetone D$_6$): 23.96; 54.24 (t, J$_{C-N}$=4.2 Hz); 63.09; 65.35 (t, J$_{C-N}$=4.0 Hz); 121.46 (q, J$_{C-F}$=322.0 Hz); 128.95; 130.42; 132.58; 133.12; 166.34.

Mass spectrometry (FAB) for C$_{15}$H$_{19}$F$_6$N$_2$O$_6$S$_2$
Theoretical mass calculated for (2C$^+$, A$^-$): 880.03713
Mass found: 880.0375

8c:
0.5 ml (5.7 mmol) of 60% HPF$_6$ in water is added to a solution of 1 g (2.98 mmol) of (8a) in 3 ml of water. The reaction mixture is left under stirring for two hours at ambient temperature in order for the exchange to be complete. The white solid obtained after filtration is washed with water then twice with 30 ml of ether and finally dried under vacuum.

White solid Yield=96% M.p.=154-156° C.

$^1$H NMR (200 MHz, Acetone D$_6$): 2.45-2.59 (m, 2H); 3.40 (s, 9H); 3.79-3.85 (m, 2H); 4.50 (t, 2H, J=5.96 Hz), 7.55 (dd, 2H, J$_1$=1.91 Hz, J$_2$=7.73 Hz); 8.00 (dd, 2H, J$_1$=1.91 Hz, J$_2$=7.74 Hz)

$^{13}$C NMR (50 MHz, Acetone D$_6$): 22.96; 53.23 (t, J=4.01 Hz); 62.31; 64.34; 128.06; 129.48; 131.79; 132.25; 165.63

$^{19}$F NMR (282 MHz, Acetone D$_6$): −71.6 (d, J=707.3 Hz; P—F)

$^{31}$P NMR (Acetone, 121.5 Mhz) δ-142 (m, J=0.7 Hz, P—F$_6$)

Mass spectrometry (FAB) for C$_{15}$H$_{19}$F$_6$NO$_2$P
Theoretical mass calculated for (2C$^+$, A$^-$): 747.0822
Mass found: 747.0824

8d:
1 ml of HBF$_4$ in 40% solution in water is added to a solution of 1 g (2.98 mmol) of (8a) in 3 ml of water. After the addition of the latter, the formation of a white solid is observed. The reaction mixture is left under stirring for two hours at ambient temperature. The white solid obtained after filtration is washed with water (in order to eliminate the excess of HBF$_4$) then twice with 30 ml of ether and finally dried under vacuum.

White solid Yield=98% M.p.=154-156° C.

$^1$H NMR (200 MHz, Acetone D$_6$): 2.39-2.57 (m, 2H); 3.35 (s, 9H); 3.70-3.87 (m, 2H); 4.50 (t, 2H, J=5.91 Hz); 7.73 (dd, 2H, J$_1$=1.97 Hz, J$_2$=6.77 Hz); 8.02 (dd, 2H, J$_1$=1.77 Hz, J$_2$=6.47 Hz)

$^{13}$C NMR (50 MHz, Acetone D$_6$): 22.96; 53.14 (4.1 Hz); 62.35; 64.29; 128.01; 129.52; 131.85; 132.24; 165.61.

$^{19}$F NMR (282 MHz, Acetone D$_6$): −150.16 (s, B—F)

Mass spectrometry (FAB) for C$_{15}$H$_{19}$F$_4$NO$_2$B
Theoretical mass calculated for (2C$^+$, A$^-$): 689.1214
Mass found: 689.1211

D/Boratrane 9:
1/Grafting on the Cation:

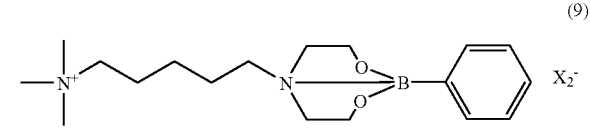

(9)

9a X$_2$=NTf$_2$
9b X$_2$=BF$_4$
9c X$_2$=PF$_6$ 2 g of (5a to 5c) and a magnetic stirrer are introduced into a 150-mL single-necked flask. The flask is placed under high vacuum for approximately 3 hours at a temperature of 50° C. The flask is then place under argon, and approximately 2.8 ml of isopropanol is added in order to solubilize the salt. 1 g of phenylboronic acid is dissolved in 60 mL of chloroform in another flask and under argon. Then this solution is added to the first. And finally, 43 mL of anhydrous ether is added and stirring is maintained for 18 hours at ambient temperature.

The medium becomes biphasic, the upper phase is eliminated and the white paste is washed 3 times with 20 ml of anhydrous ether.

9a:
Light Yellow Viscous Oil.
$^1$H NMR (200 MHz, Acetone D$_6$): 1.40-2.20 (m, 6H); 3.30 (s, 9H); 3.35-3.70 (m, 6H); 3.95-4.10 (m, 6H); 7.25-7.5 (m, 3H); 7.70-7.90 (m, 2H)

$^{13}$C NMR (50 MHz, Acetone D$_6$): 24.14; 26.58; 30.24; 56.7; 57.05; 60.7; 64.04; 66.8; 67.3; 67.8; 128.97; 135.45

$^{11}$B NMR spectrum (96.25 MHz, Acetone): 13.06

9b:
White Paste
$^1$H NMR (200 MHz, Acetone. D$_6$): 1.42-2.25 (m, 6H); 3.01 (s, 9H); 3.29-3.62 (m, 6H); 3.95-4.1 (m, 6H); 7.23-7.58 (m, 3H); 7.70-7.91 (m, 2H)

$^{11}$B NMR (96.25 MHz, Acetone): 29.96 (60%); 4.40 (40%)

9c:

White Paste $^1$H NMR (200 MHz, Acetone): 1.40-2.21 (m, 6H); 3.16 (s, 9H); 3.34-3.73 (m, 6H); 3.91-4.12 (m, 6H); 7.25-7.51 (m, 3H); 7.72-7.89 (m, 2H)

2/Grafting on the Anion:

a—Quaternization by a Hydroxyl

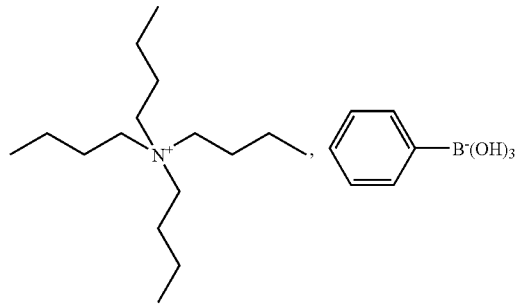

(10)

0.1 g (0.38 mmol) of tetrabutylammonium hydroxide is dissolved in 0.6 g of N,N',N"-trimethylbutylammonium bis-trifluoromethanesulphonamide as matrix in a 5-ml flask. 47 mg (0.38 mmol) of phenylboronic acid and finally 0.5 mL of THF (anhydrous) are added to this solution. The solution is left under stirring for 2 hours at ambient temperature. Then the THF is evaporated to dryness and the solution is dried under vacuum.

Tinted Viscous Oil.

$^1$H NMR (200 MHz, Acetone D$_6$): 0.9-1.05 (m, 12H); 1.21-1.52 (m, 8H); 1.5-1.8 (m, 8H); 3.0 (broad singlet, 8H); 6.90-7.30 (m, 3H); 7.60-7.70 (m, 2H).

$^{13}$C NMR (50 MHz, Acetone D$_6$): 14.21; 20.50; 24.78; 25.75; 26.56; 53.78; 59.67; 67.45; 68.56; 127.94; 134.60

$^{11}$B NMR spectrum (96.25 MHz, Acetone): 3.97 b—Quaternization by the Fluoride:

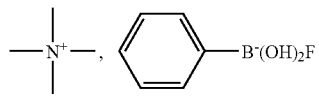

(11)

0.1 g (2.1 mmol) of anhydrous tetramethylammonium fluoride is introduced into a 10-mL single-necked flask, then 1 mL of THF (anhydrous) is added and the solution is homogenized while heating if necessary. Finally, 0.13 g of phenylboronic acid (2.1 mmol) is introduced. Stirring is maintained for approximately 2 hours at ambient temperature.

After stirring for 2 hours, anhydrous ether is added for better crystallization and the solid is filtered on sintered glass. The solid is washed 2 to 3 times with 20 ml of ether. And finally, the solid is placed under vacuum in order to dry it.

White solid Yield=82% M.p.=162-164° C.

$^1$H NMR (200 MHz, Acetone D$_6$): 3.15 (s, 12H); 6.8-7.4 (m, 3H); 7.50-7.70 (m, 2H)

$^{13}$C NMR (50 MHz, Acetone D$_6$): 56.19 (t, J$_{C-N}$=3.97 Hz); 127.47; 128.36; 130.91; 132.98; 135.96.

$^{19}$F NMR spectrum (282 MHz, Acetone D$_6$): −136.40 (multiplet).

$^{11}$B NMR spectrum (96.25 MHz, Acetone D$_6$): 4.66 (D, J$_{B-F}$=27.2 Hz)(56%); 28.5 (44%).

E/Synthesis of the Supported Triethylamine (STEA)(12):

3 g (6.1 mmol) of (3b), 12 mL of ethanol and 13 g (18 mmol) of diethylamine are introduced into a single-necked flask. A condenser is fitted and the reaction mixture is then taken to reflux for approximately 14 hours. After which, the ethanol and the excess diethylamine are evaporated off. The oil obtained is dissolved in dichloromethane and the solution is washed with twice 5 mL of diluted K$_2$CO$_3$. The organic phase is separated, dried over MgSO$_4$ and the solvent evaporated to dryness.

Orange viscous oil Yield=83%

$^1$H NMR spectrum (200 MHz, Acetone D6): 1.05 (t, J=7.1 Hz, 2H); 1.40-1.70 (m, 2H); 1.90-2.10 (m, 4H); 2.50-2.70 (m, 6H); 3.35 (s, 9H); 3.50-3.70 (m, 2H).

$^{13}$C NMR spectrum (50 MHz, Acetone): 12.34; 23.813; 25.08; 27.48; 48.140; 53.543; 54.04 (t, J$_{C-N}$=4.02 Hz); 67.93; 124.594 (q, J=319.9 Hz)

EXAMPLES

The different functionalized salts used were prepared according to the procedures described in the literature.

In order to illustrate this principle, we chose to support:

an acryl ester via an ammonium salt the preparation of which is described in the diagram below; this salt was then involved in three examples of reactions of great interest in organic chemistry;

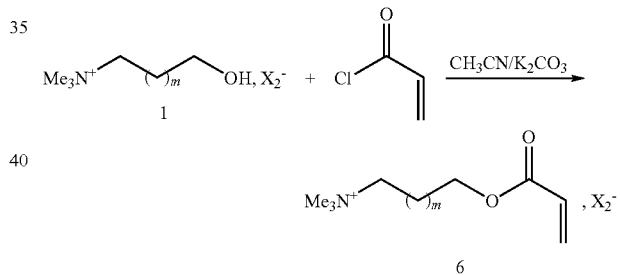

an acryl ester substituted by a halogen prepared according to the reaction diagram below, which was tested in two examples of coupling reactions;

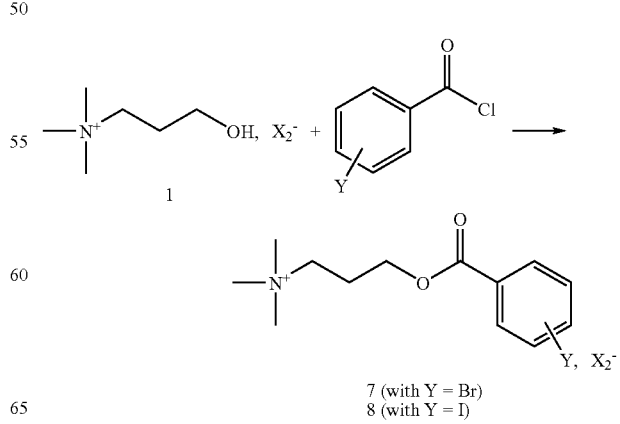

7 (with Y = Br)
8 (with Y = I)

an arylboronic acid ester in the form of boratrane (functionalization of the cationic part) or in the form of borate (functionalization of the anionic part of the functionalized salt).

The synthesis of functionalized salts and of ionic substrates is described in detail in the experimental part which follows.

Example 1

Heck Reaction

The formation of carbon-carbon bonds is a fundamental operation in organic chemistry. Among the large number of possible reactions, the methods using organometallic catalysts are extremely important. In particular, we used the principle of the invention of organic synthesis supported on ionic liquid (OSSIL) in the coupling of alkenes catalyzed by palladium with aryl iodides of known by the name of Heck coupling.

This reaction has been the subject of several works using ionic liquids as solvents (Abbott et al., 2002; Murphy et al., 2000; Fraga-Dubreuil et al., 2001; Visser et al., 2002; Visser et al., 2001). In 1999, Xiao J. et al., have shown the possibility of the recycling of the catalytic system and the effect of the anion on the kinetics and the selectivity of the reaction (Jeffery et al., 1996; Howarth et al., 2000; Bayer et al., 1991).

In this example acryl ester and an acryl ester substituted by an iodine atom are separately used as substrates.

1—Acryl Ester:

The acrylate (6) was involved in Heck in the presence of palladium acetate as catalyst, potassium bicarbonate as base and an aryl iodide in large excess as reagent (see diagram hereafter).

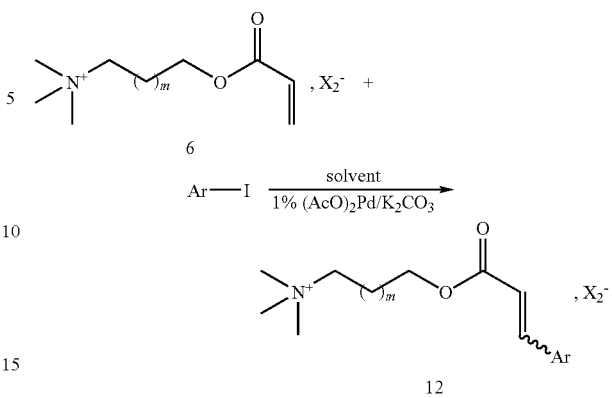

All the coupling reactions were carried out at 80° C. with $A_1^+X_1^-=Me_3N^+Bu$, $^-NTf_2$ as liquid matrix. The monitoring of the reactions was carried out by proton NMR at 200 MHz and FIG. 1 shows the example of the reaction of the salt 6 ($X_2^-=NTf_2^-$) in solution in trimethylbutylammonium triflimide with 1-iodonaphthalene (test 9 in Table I below).

Figure 1:
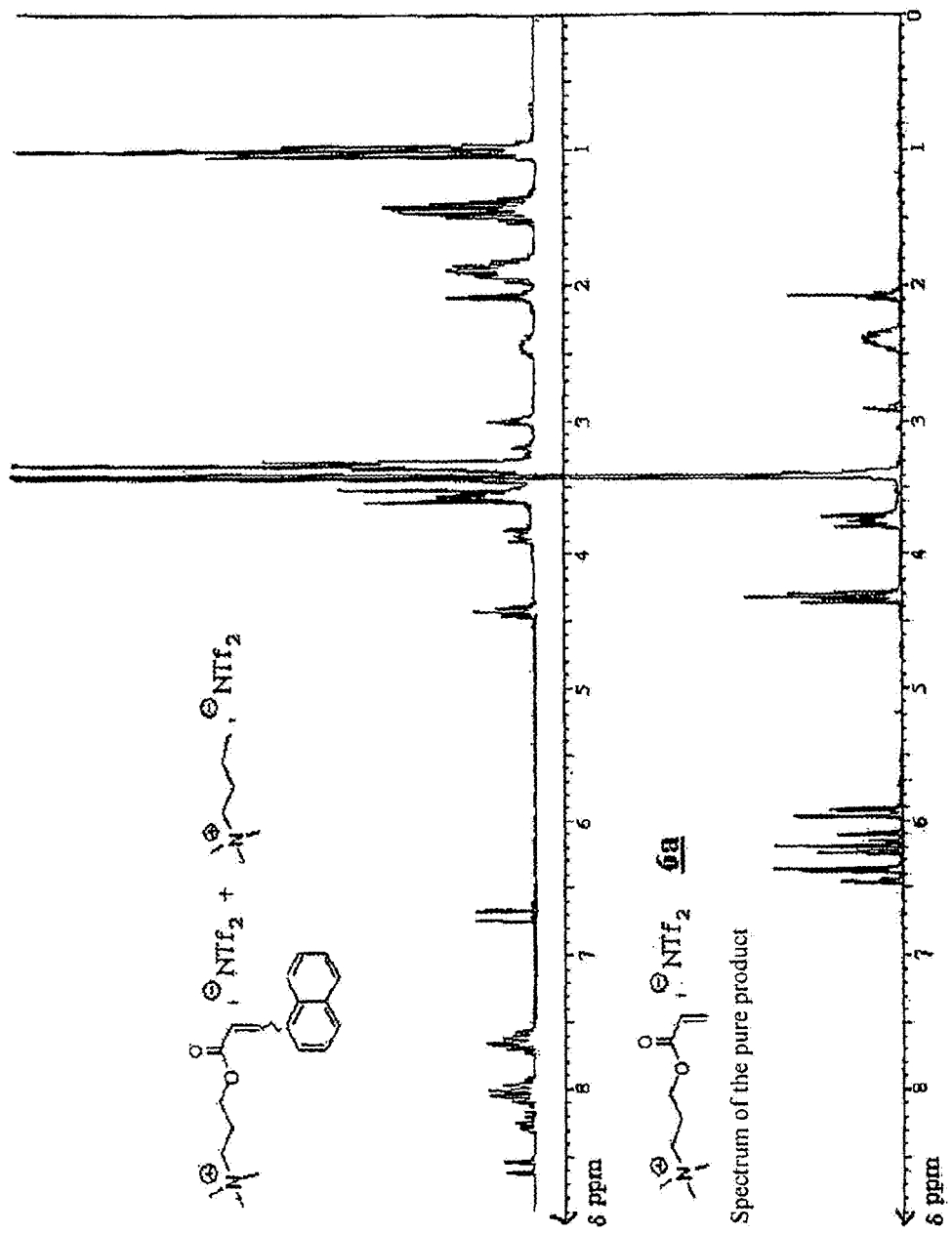
FIG. 1 represents proton NMR spectra recorded at 200 MHz in acetone D6, corresponding to monitoring of the Heck coupling reaction between the supported acrylate 6 and 1-iodonaphthalene.
Figure 2:
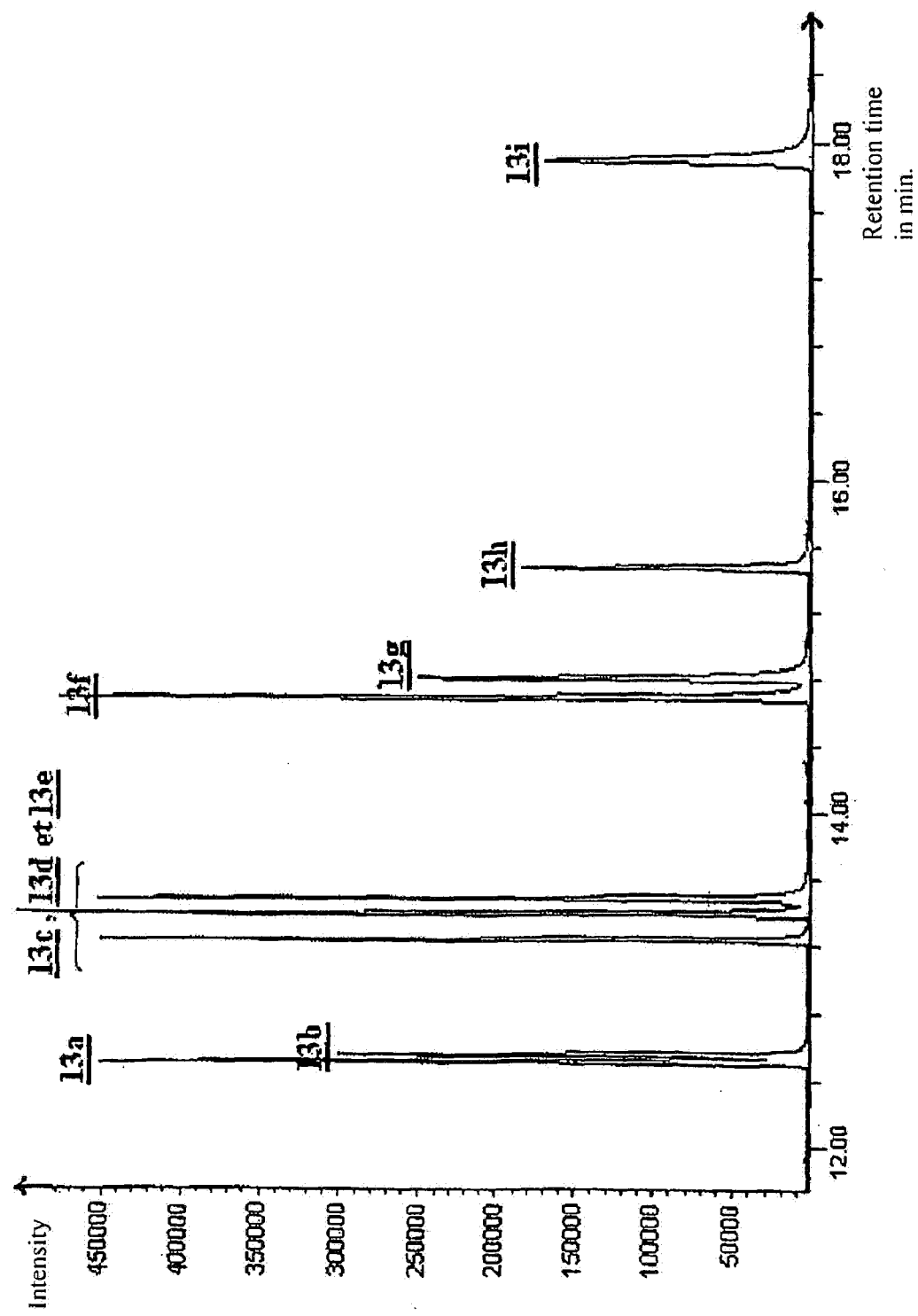
FIG. 2 represents a chromatogram corresponding to the mixture of the nine methyl esters 13a to 13i the mass spectra of which are described in Table II.
Figure 3:
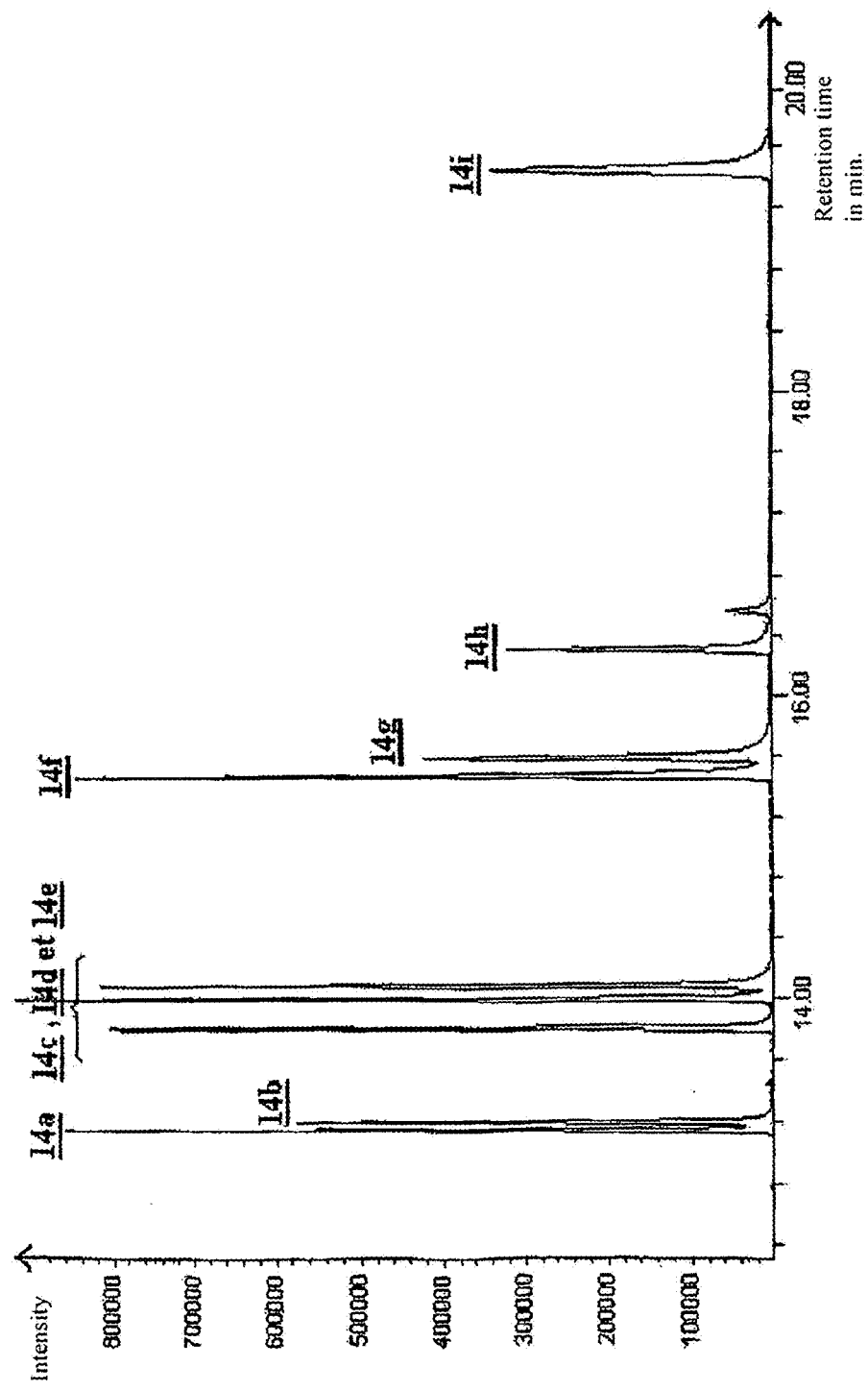
FIG. 3 represents a chromatogram corresponding to the mixture of the nine ethyl esters 14a to 14i the mass spectra of which are described in Table III.
Figure 4:
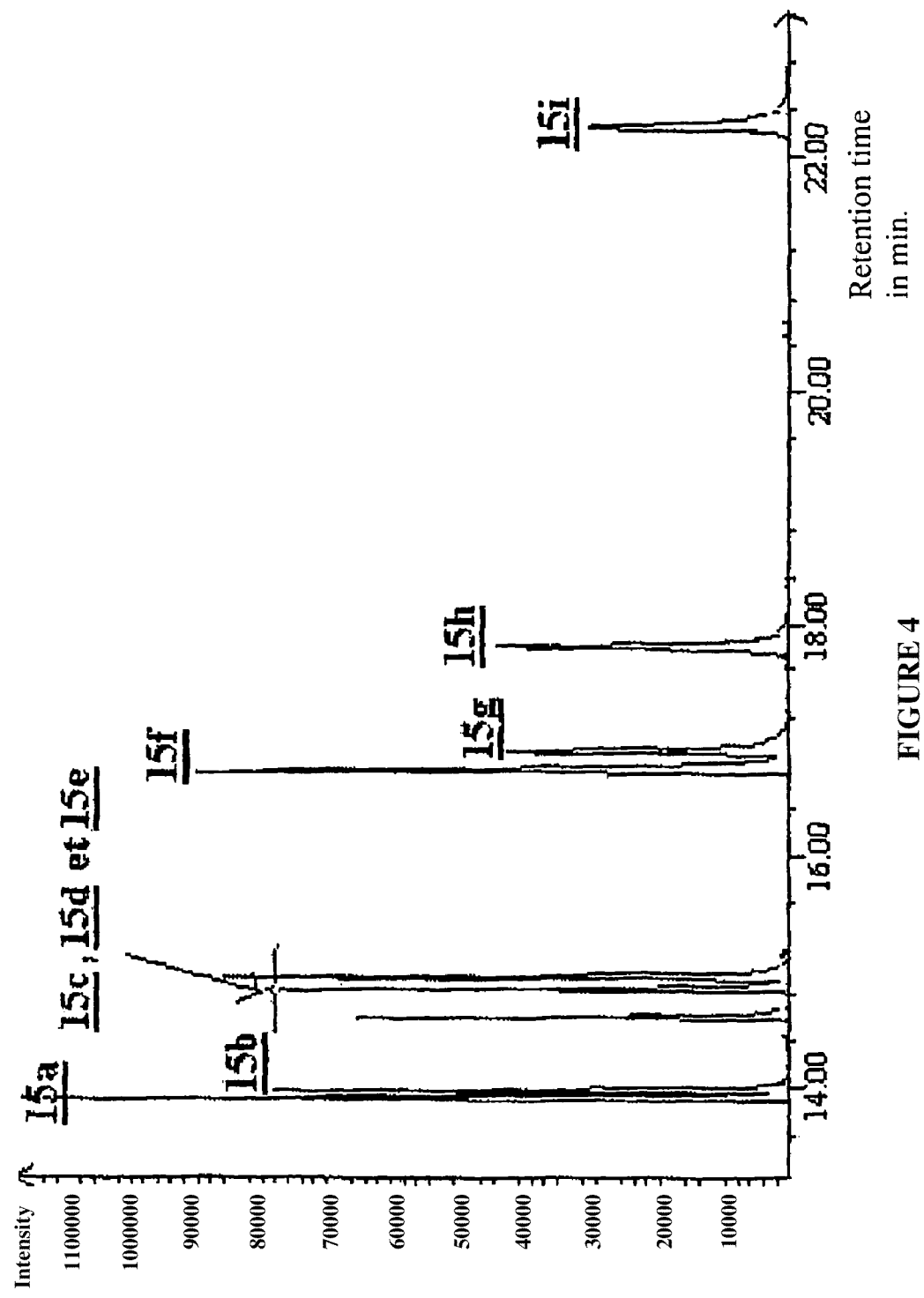
FIG. 4 represents a chromatogram corresponding to the mixture of the nine propyl esters 15a to 15i the mass spectra of which are described in Table IV.
Figure 5:
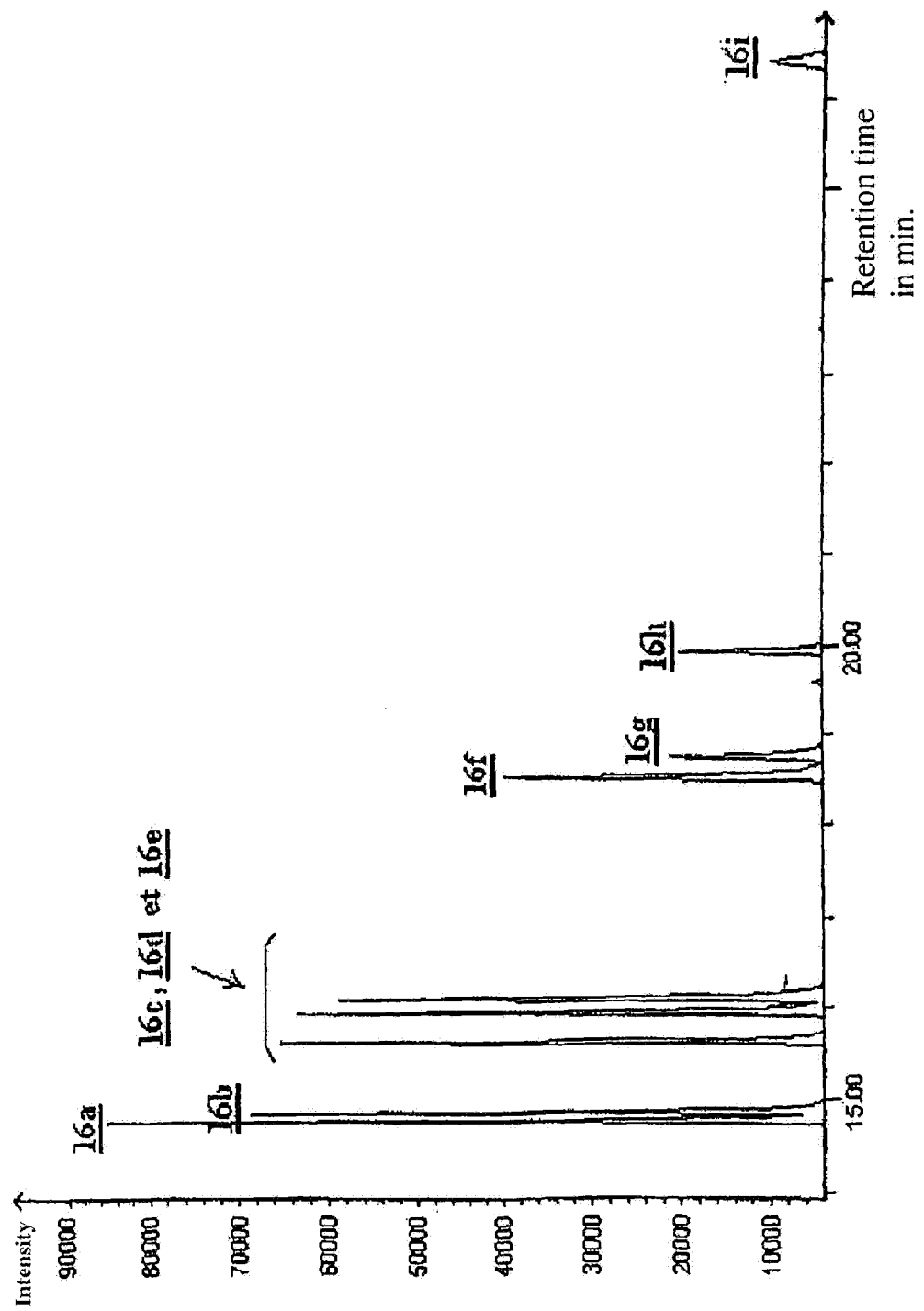
FIG. 5 represents a chromatogram corresponding to the mixture of the nine butyl esters 16a to 16i the mass spectra of which are described in Table V.

According to FIG. 1, it is noted that it is possible and simple to monitor the reaction by $^1H$ NMR. In fact, the total disappearance of signals between 5.9 and 6.5 ppm is noted corresponding to the three protons of the double bond of the substrate 6, and the appearance of signals of the double bond of the product resulting from the Heck coupling 12.

This type of monitoring is impossible in the case of the use of an insoluble solid support and less evident in the case of the soluble support (PEG) described in the literature due to broad NMR signals.

The results obtained for a reaction time of 2 hours at 80° C. are collected in Table I below:

TABLE I

| test | Ar | $X^i$ | Solvent or ionic matrix[i] | Conversion $(\%)^{ii}$ | $E/Z^{iii}$ Ratio |
|---|---|---|---|---|---|
| 1 | phenyl | — | $CH_3CN$ | 26 | >98/2 |
| 2 | phenyl | $NTf_2$ | $CH_3CN$ | 70 | 88/12 |
| 3 | phenyl | $BF_4$ | $Me_3N^{\oplus}\diagup\diagup\diagup, NTf_2^{\ominus}$ | 75 | 84/16 |

TABLE I-continued

| test | Ar | X[i] | Solvent or ionic matrix[i] | Conversion (%)[ii] | E/Z[iii] Ratio |
|---|---|---|---|---|---|
| 4 | 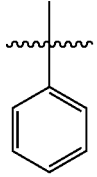 | NTf$_2$ | 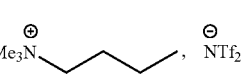 Me$_3$N$^\oplus$⁀⁀⁀, $^\ominus$NTf$_2$ | 100 | >99/1 |
| 5 | 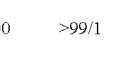 | NTf$_2$ | 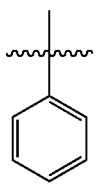, $^\ominus$NTf$_2$ | 100 | >99/1 |
| 6 | 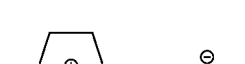 | NTf$_2$ | 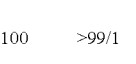 Me$_3$N$^\oplus$⁀⁀⁀, $^\ominus$NTf$_2$ | 100 | >99/1 |
| 7 | 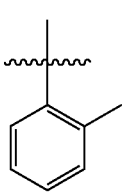 | NTf$_2$ |  Me$_3$N$^\oplus$⁀⁀⁀, $^\ominus$NTf$_2$ | 100 | >99/1 |
| 8 | 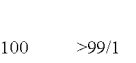 | NTf$_2$ | 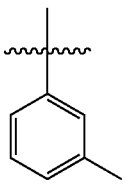 [SMILES: *c1cccc(C)c1] Me$_3$N$^\oplus$⁀⁀⁀, $^\ominus$NTf$_2$ | 100 | >99/1 |
| 9 |  | NTf$_2$ | 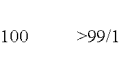 Me$_3$N$^\oplus$⁀⁀⁀, $^\ominus$NTf$_2$ | 100 | >99/1 |
| 10 | 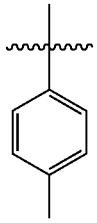 | NTf$_2$ | 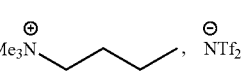 Me$_3$N$^\oplus$⁀⁀⁀, $^\ominus$NTf$_2$ | 100 | >99/1 |

TABLE I-continued

| test | Ar | $X^i$ | Solvent or ionic matrix[i] | Conversion (%)[ii] | E/Z[iii] Ratio |
|---|---|---|---|---|---|
| 11 | 4-OMe-C6H4- | NTf2 | Me3N⁺~~~~, NTf2⁻ | 100 | >99/1 |
| 12 | 4-F-C6H4- | NTf2 | Me3N⁺~~~~, NTf2⁻ | 100 | >99/1 |
| 13 | 3-Br-C6H4- | NTf2 | Me3N⁺~~~~, NTf2⁻ | 100 | >99/1 | i: $NTf_2 = N(SO_2CF_3)_2$
ii: determined by NMR
iii: determined by NMR and confirmed by GC.

The results of the table above show that the use of the supported substrate makes it possible to have a better reactivity in comparison with the use of a standard substrate (compare tests 1 and 2).

The use of the ionic liquid as solvent has distinctly increased the reaction speed and made it possible to have a better stereoselectivity compared with acetonitrile which is often used as solvent for this reaction (tests 2 and 4).

A direct relationship is noted between the reactivity/selectivity and the nature of the anion of the supported substrate (tests 4 and 5).

The nature of the reagent seems to have no influence on the reaction.

In the last stage for this example, the product is released from the support by transesterification with an alcohol (Diagram below), and the possibility of adapting this methodology to the combinatorial technique was tested.

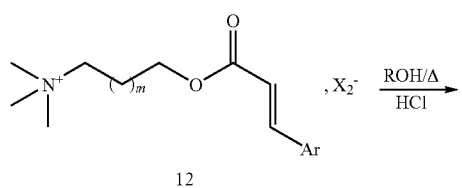

12

-continued

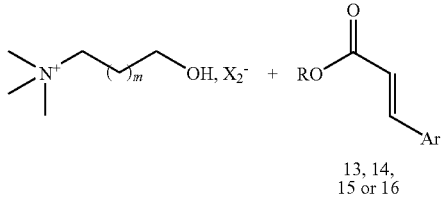

13, 14, 15 or 16

Thus, transesterification was carried out with different alcohols on a mixture of the products 12a to 12i isolated during the last stage, according to the procedure below. The alcohols used are methanol, ethanol, propanol and butanol.

Procedure:

Four synthetic mixtures constituted by 100 mg from each of the tests: 5, 6, 7, 8, 9, 10, 11, 12, 13 (Table I) are dissolved in 5 ml of methanol, ethanol, propanol and butanol respectively. 5 drops of concentrated hydrochloric acid (12N) are then added to each solution following by taking to reflux for 12 hours. The monitoring of the reaction is carried out by $^1H$ NMR where a difference is observed in the chemical shifts between the protons of the salts with a dedicated task 12 and 1, as represented hereafter:

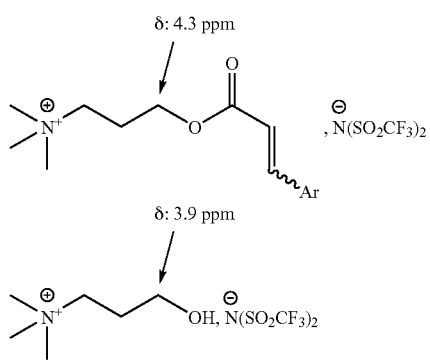

After 12 hours, each solution is evaporated to dryness and the different mixtures are separately extracted with 3 times 15 ml of diethyl ether. The products extracted are then analyzed in MS-GPC, and the chromatograms corresponding to each mixture are presented below.

In the chromatograms represented in FIGS. 2 to 5, the 36 expected products are found (13a to 13i; 14a to 14i; 15a to 15i; 16a to 16i). This validates the OSSIL principle and demonstrates its applicability to combinatorial synthesis.

Compounds 13a to 13i corresponds to the product of formula

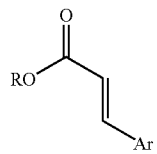

in which R is a methyl group.

Table II below shows these 9 methyl esters, indicating for each the meaning of Ar. This table corresponds to the chromatogram of FIG. 2.

TABLE II

| Retention time (min) | Mass found | 13 | Ar |
|---|---|---|---|
| 12.50 | 180 | 13a | F-phenyl |
| 12.55 | 162 | 13b | phenyl |
| 13.22<br>13.38<br>13.47 | 176 | 13c<br>13d<br>13e | CH₃-phenyl |
| 14.69 | 240 | 13f | Br-phenyl |

TABLE II-continued

| Retention time (min) | Mass found | 13 | Ar |
|---|---|---|---|
| 14.80 | 192 | 13g | OMe-phenyl |
| 15.47 | 207 | 13h | NO₂-phenyl |
| 17.91 | 212 | 13i | naphthyl |

Compounds 14a to 14i correspond to the product of formula

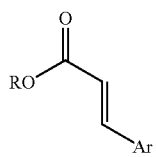

in which R is an ethyl group.

Table III below shows these 9 ethyl esters, indicating for each the meaning of Ar. This table corresponds to the chromatogram of FIG. 3.

TABLE III

| Retention time (min) | Mass found | 14 | Ar |
|---|---|---|---|
| 13.136 | 194 | 14a | F-phenyl |
| 13.196 | 176 | 14b | phenyl |
| 13.800<br>13.980<br>14.087 | 190 | 14c<br>14d<br>14e | CH₃-phenyl |
| 15.475 | 254 | 14f | Br-phenyl |
| 15.577 | 206 | 14g | OMe-phenyl |

TABLE III-continued

| Retention time (min) | Mass found | 14 | Ar |
|---|---|---|---|
| 16.318 | 221 | 14h | 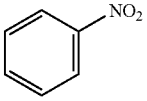 |
| 19.434 | 226 | 14i | 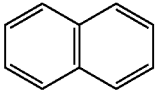 |

Compounds 15a to 15i correspond to the product of formula

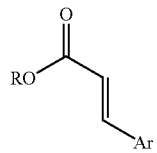

in which R is a propyl group.

Table IV below shows these 9 propyl esters, indicating for each the meaning of Ar. This table corresponds to the chromatogram of FIG. 4.

TABLE IV

| Retention time (min) | Mass found | 15 | Ar |
|---|---|---|---|
| 13.902 | 208 | 15a | 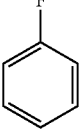 |
| 13.992 | 1190 | 15b |  |
| 14.608<br>14.859<br>14.973 | 204 | 15c<br>15d<br>15e | 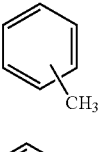 |
| 16.731 | 270 | 15f |  |
| 16.905 | 120 | 15g | 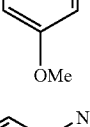 |
| 17.814 | 234 | 15h | 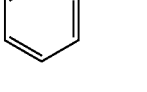 |

TABLE IV-continued

| Retention time (min) | Mass found | 15 | Ar |
|---|---|---|---|
| 22.264 | 240 | 15i | 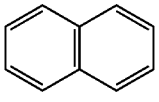 |

Compounds 16a to 16i correspond to the product of formula

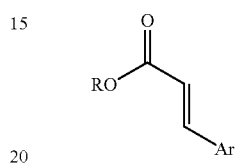

in which R is a butyl group.

Table V below shows these 9 butyl esters, indicating for each the meaning of Ar. This table corresponds to the chromatogram of FIG. 5.

TABLE V

| Retention time (min) | Mass found | 16 | Ar |
|---|---|---|---|
| 14.752 | 222 | 16a |  |
| 14.853 | 204 | 16b |  |
| 15.625<br>15.930<br>116.109 | 218 | 16c<br>16d<br>16e |  |
| 18.544 | 284 | 16f |  |
| 18.783 | 234 | 16g |  |
| 19.931 | 249 | 16h | 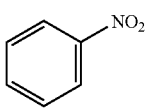 |
| 26.390 | 254 | 16i | 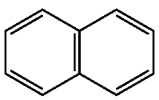 |

2—Iodo-Arylic Ester:

The second example of functionalized salt which was tested in the Heck reaction is an aryl iodide supported on (TMHPA, NTf$_2$) (1) according to the following diagram:

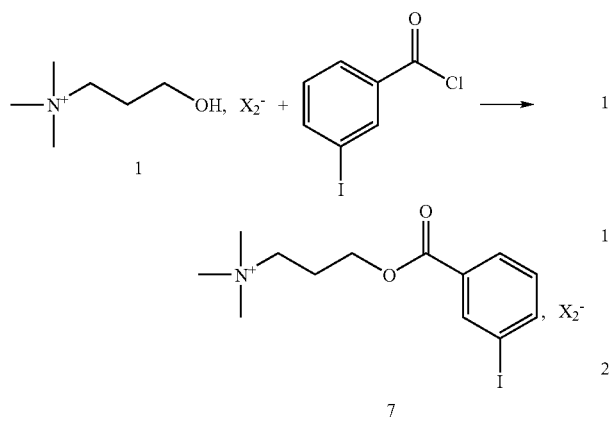

Figure 6:
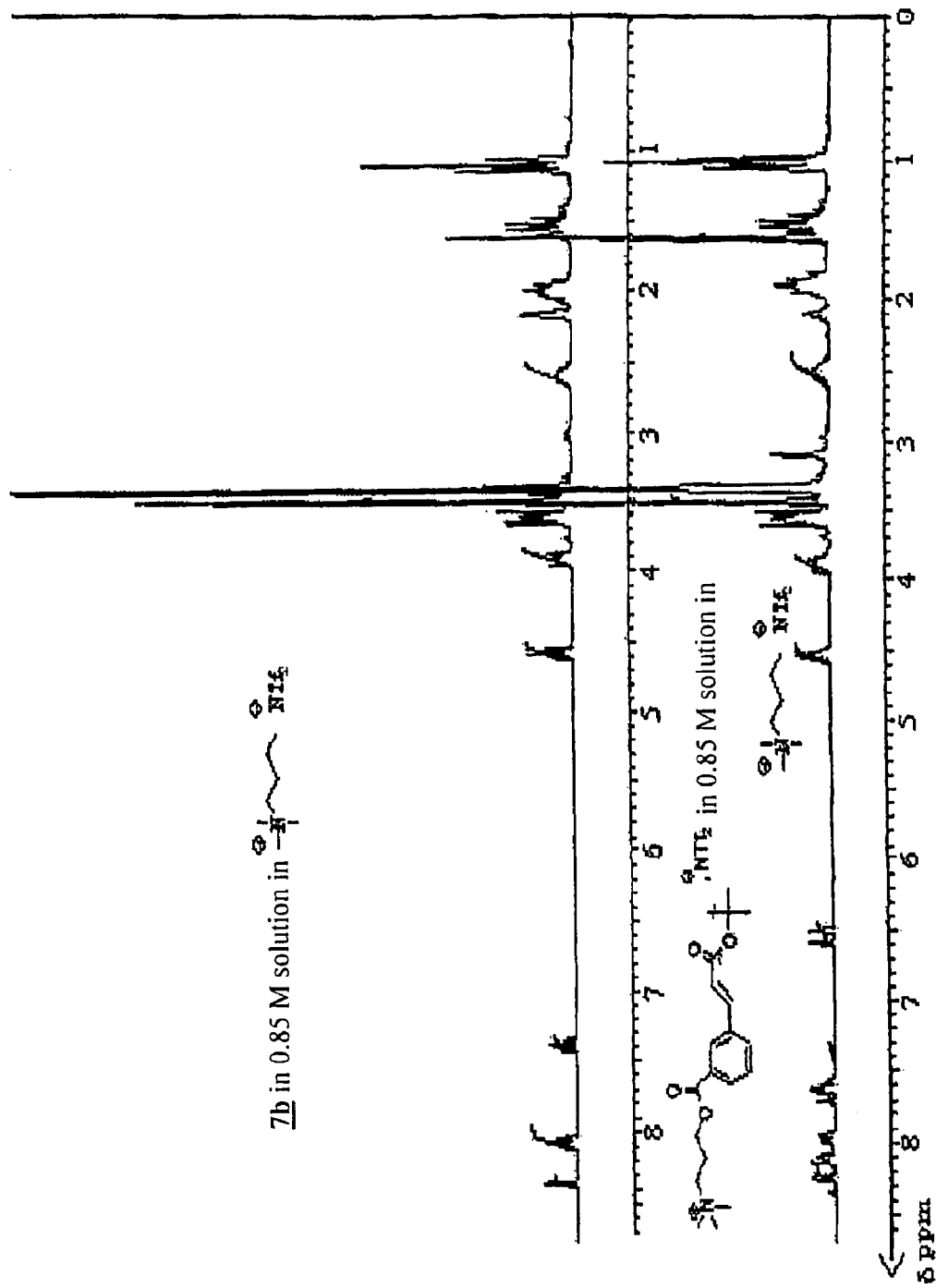
FIG. 6 represents proton NMR spectra recorded at 200 MHz in acetone D6, corresponding to monitoring of the Heck coupling reaction between the supported aryl iodide 7 and tertbutyl acrylate.

During this example, we took to 80° C. for 3 hours a mixture constituted:
- by a solution of 0.85% molar of the salt 7 dissolved in trimethylbutylammonium trifluoromethanesulphonamide (TMBA, NTf$_2$) as matrix,
- tertbutyl acrylate as alkene,
- palladium acetate as catalyst
- solid K$_2$CO$_3$ as base The reaction corresponds to the following diagram:

The monitoring of the reaction is carried out by $^1$H and $^{13}$C NMR and FIG. 6 illustrates and confirms the simplicity of monitoring by this analysis technique, a more difficult matter in the case of the solid or soluble supports described in the literature.

3—Test on 6 Grams (15 mmol) of Functionalized Salt 6a.

All the coupling tests were carried out on very small quantities. For the purpose of showing that the OSSIL principle can be extrapolated to the gram scale or even to large quantities ("large scale"), we tested the Heck coupling reaction on 6 g (15 mmol) of acryl ester (6a), under the same operating conditions as those described in the first part of this example, using iodobenzene as substrate (5 eq), butyl-methyl imidazolium hexafluorophosphate [BMIM][PF$_6$] as matrix (11 g), and palladium acetate as catalyst (25 mg). After 3 hours, the proton spectrum NMR shows that the reaction is complete.

After washing with ether in order to eliminate the excess of iodobenzene, transesterification by methanol was carried out.

The yield of pure isolated product is 86%.

The first recycling of the functionalized salt leads to a yield of 88%.

Example 2

Diels-Alder Reaction

The richness and the potential of the Diels-Alder reaction have encouraged chemists to research methods making it possible to increase on the one hand speed and yield, on the other hand regio- and stereoselectivity. Recently, works using ionic liquids as solvent have shown the influence of their polarity on the endo/exo ratio (Xiao et al., 2000). This reaction is the second example chosen in order to show the benefit of the strategy of organic synthesis supported on OSSIL ionic liquid.

The Diels-Alder reaction between a dienophile 6 and cyclopentadiene was therefore studied. The diagram hereafter represents the different stages.

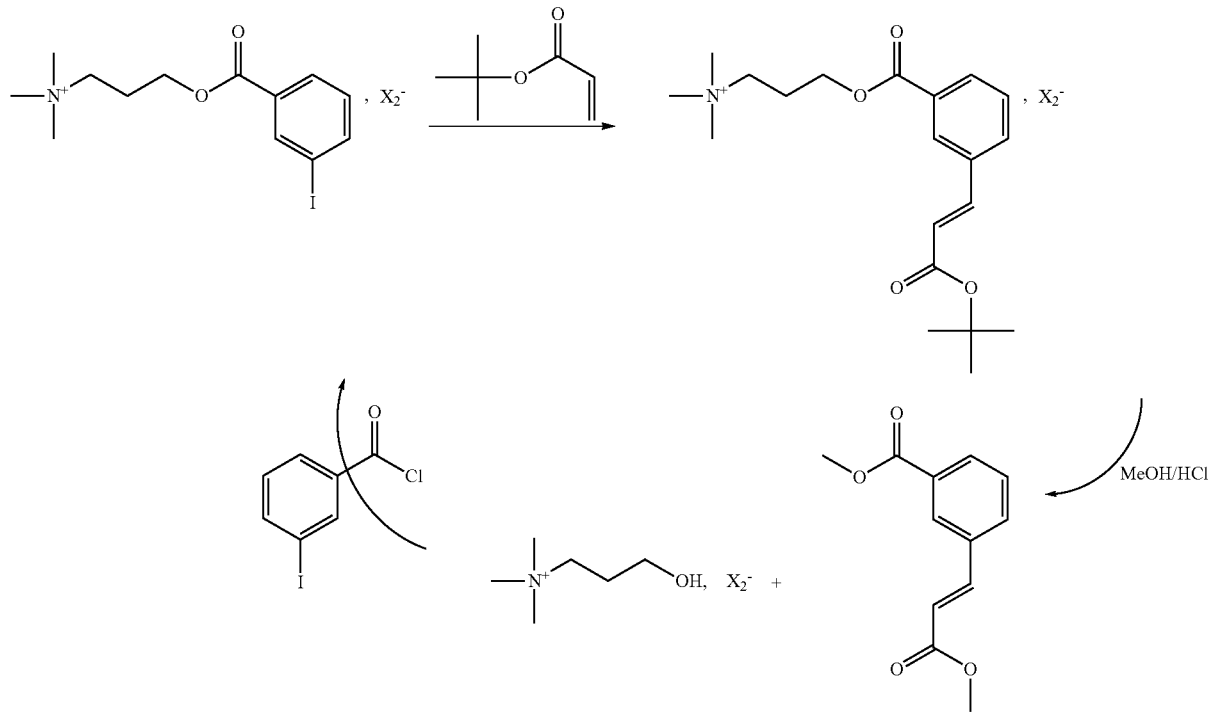

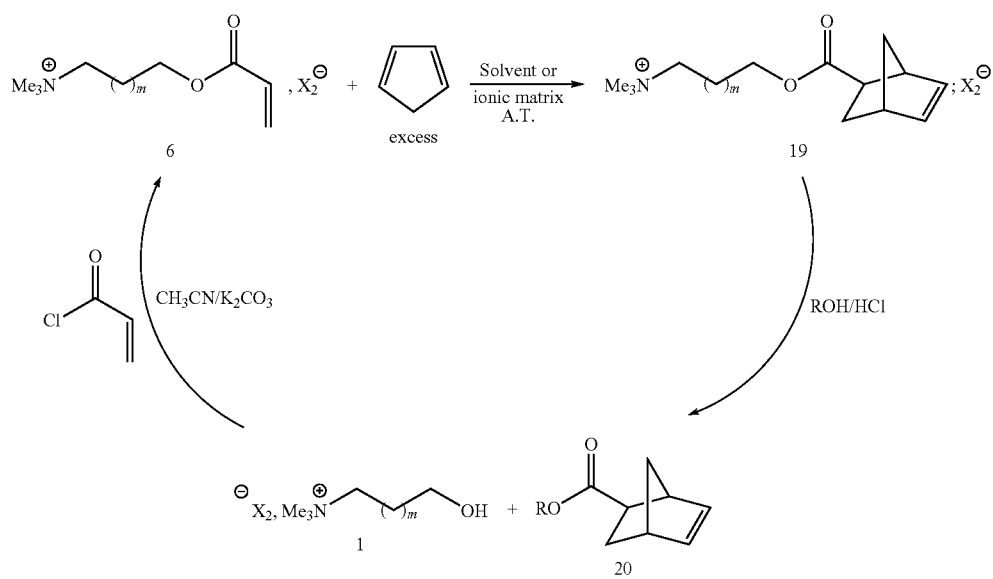

Procedure:

A solution of (6) and 10 equivalents of cyclopentadiene, in a solvent or in an ionic matrix, is stirred for two hours at ambient temperature. The excess of the reagent is then eliminated under vacuum and the reaction product thus obtained is put into solution in methanol, ethanol or butanol in the presence of five drops of 12 N hydrochloric acid.

After twelve hours under reflux, transesterification is complete and the product is then extracted with pentane. The results obtained are shown in Table VI below:

TABLE VI

| test | N | $X_2$ | Solvent or Liquid matrix | R | Conv. rate (%) | Endo/exo % |
|---|---|---|---|---|---|---|
| 1 | 4 | $NTf_2$ | $Me_3N^+\!\!\sim\!\!\sim$, $NTf_2^-$ | Me | 85 | 80/20 |
| 2 | 1 | $NTf_2$ | $Me_3N^+\!\!\sim\!\!\sim$, $NTf_2^-$ | Me | 94 | 81/19 |
| 3 | 1 | $NTf_2$ | Without solvent[i] | Me | 96 | 83/17 |
| 4 | 1 | $NTf_2$ | $CH_2Cl_2$ | Me | 86 | 80/20 |
| 5 | 1 | $NTf_2$ | imidazolium, $NT_2^-$ | Me | 93 | 80/20 |
| 6 | 1 | $NTf_2$ | $Me_3N^+\!\!\sim\!\!\sim\!\!OH$, $NTf_2^-$ | Me | 95 | 82/18 |
| 7 | 1 | $NTf_2$ | " | Et | 89 | 82/18 |
| 8 | 1 | $NTf_2$ | " | Pr | 97 | 81/19 |
| 9 | 1 | Cl | " | Me | 95 | 78/22 |
| 10 | 1 | $BF_4$ | " | Me | 92 | 80/20 | i: 2, $^-N(SO_2CF_3)_2$ is liquid at ambient temperature.

The results of this table show that the length of the alkyl chain of the L arm influences the reaction speed. In fact, by increasing the chain by 3 carbon atoms, the reaction speed is reduced without inhibiting it (compare tests 1 and 2). Conversely, no influence on reactivity and selectivity is observed for the different ionic matrices and anions of the support (tests 5 to 10).

The regiospecificity of this reaction is comparable to that observed in the case of the non-supported substrate, i.e. methyl acrylate.

Finally, we tested the possibility of recycling the ionic support solution, in two different cases. The results that we obtained are shown in Table VII which follows:

TABLE VII

| test | $X_2$ | Liquid matrix | Yield of 2 stages |
|---|---|---|---|
| 1st reaction | $NTf_2$ | $Me_3N^+\!\!\sim\!\!\sim$, $NTf_2^-$ | 78 |
| 1st recycling | $NTf_2$ | $Me_3N^+\!\!\sim\!\!\sim$, $NTf_2^-$ | 75 |
| 2nd | $NTf_2$ | $Me_3N^+\!\!\sim\!\!\sim$, $NTf_2^-$ | 77 |
| 3rd | $NTf_2$ | $Me_3N^+\!\!\sim\!\!\sim$, $NTf_2^-$ | 81 |
| 1st reaction | Cl | imidazolium, $NT_2^-$ | 83 |
| 1st recycling | Cl | imidazolium, $NT_2^-$ | 80 |
| 2nd | Cl | imidazolium, $NT_2^-$ | 85 |

Whatever the nature of the anion the yields of isolated product 18 are identical as well as the percentage of the two isomers. It should also be noted that in the second case (6b), after three recycling processes, more than 85% of the functionalized salt 1a is isolated from the matrix by simple filtration after precipitation in acetone. This recovery operation of the functionalized salt can prove useful for the recycling of the matrix and of the functionalized salt.

Example 3

Baylis-Hillman Reaction

The third example used in order to validate the OSSIL principle is the Baylis-Hillman reaction, which consists of the condensation of an aldehyde on the double bond of the acrylic substrate 6 in the presence of 3-hydroxyquinuclidine (see diagram hereafter).

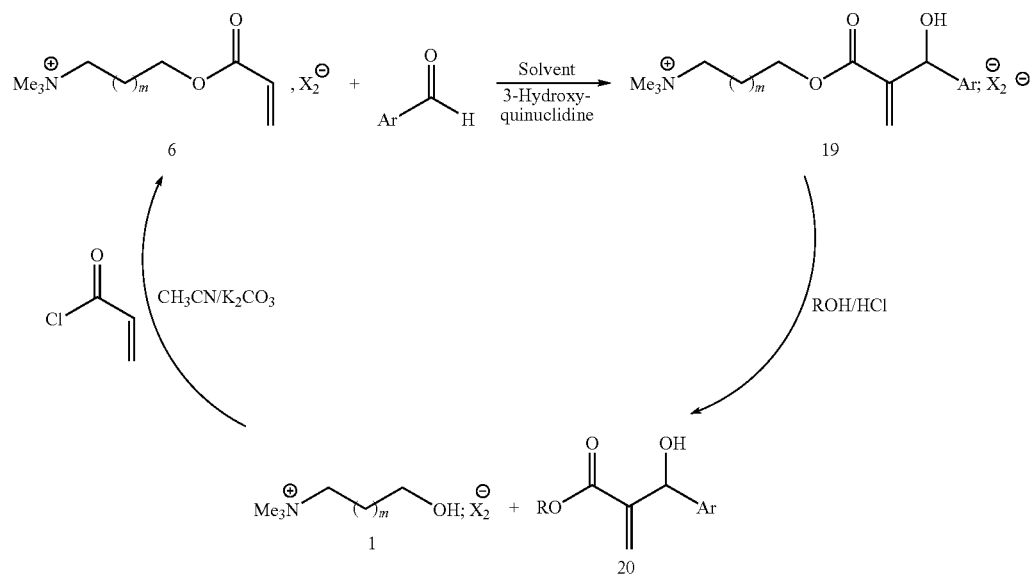

General Procedure:

A mixture of 2 mmol of 6 and 10 mmoles of aldehyde in a solvent or an ionic matrix is stirred at ambient temperature in the presence of 2 mmoles of 3-hydroxyquinuclidine as base.

After 24 hours, washing in ether is carried out in order to eliminate the excess reagent and the conversion rate is determined by NMR. The results are shown in Table VIII which follows.

TABLE VIII

| test | Ar | Solvent or liquid matrix | % Yield in 19[i] |
|---|---|---|---|
| 9 | ![benzene] | $C_2H_5OH$ | 40 |
| 1 | ![PhOMe] | ![methyl-ethyl imidazolium NTf2] | 45 |
| 2 | ![PhOMe] | ![methyl-ethyl imidazolium NTf2] | 42 |
| 3 | ![PhNO2] | ![methyl-ethyl imidazolium NTf2] | 65 |
| 4 | ![Ph(NO2)2] | ![methyl-ethyl imidazolium NTf2] | 75 |
| 5 | ![PhBr] | ![methyl-ethyl imidazolium NTf2] | 64 |

TABLE VIII-continued

| test | Ar | Solvent or liquid matrix | % Yield in 19[i] |
|---|---|---|---|
| 6 | 4-chlorophenyl | " | 60 |
| 7 | 4-fluorophenyl | " | 75 |
| 8[ii] | phenyl | 1-methyl-3-ethylimidazolium, NTf$_2^-$ | 39 |
| 10 | phenyl | 1-methyl-3-ethylimidazolium, NTf$_2^-$ | 50 |
| 11 | phenyl | Me$_3$N$^+$–(CH$_2$)$_4$–, NTf$_2^-$ | 46 |
| 12 | phenyl | Me$_3$N$^+$–(CH$_2$)$_3$–OH, NTf$_2^-$ | 60 |
| 13 | phenyl | 1-methyl-3-(hydroxypropyl)imidazolium, NTf$_2^-$ | 71 |
| 14 | phenyl | 1-methyl-3-ethylimidazolium, PF$_6^-$ | 55 |
| 15 | phenyl | P(C$_6$H$_{13}$)$_3$C$_{14}$H$_{29}^+$; NTf$_2^-$ | 25 |

[i] yield of isolated product after transesterification.
[ii] test with methyl acrylate as substrate.

Better reactivity of the ionic substrate 6 is noted compared with the results achieved with methyl acrylate as substrate in an ionic liquid as solvent (compare tests 8 and 10). The nature of the latter distinctly influences the reaction speed. In fact, the use of an ionic matrix carrying an alcohol function increases reactivity (compare tests 10, 11 and 12, 13).

The influence of the nature of the reagent on yields is very considerable, it is comparable to that described in works related to the non-supported substrates or during the use of the solid supports. It should however be noted that the yields which we obtained are distinctly better compared with the latter.

Example 4

Suzuki Coupling

Another example where we applied the OSSIL principle is the Suzuki coupling reaction which consists of the coupling of an aryl halide and an aryl boronic acid.

This study was carried out according to two distinct approaches:
1—using a supported aryl halide;
2—using a supported boronic acid.

A—Supported Aryl Halide:

In this study 3-iodobenzoic acid and 4-bromobenzoic acid were used as supported aryl halide. In a first phase and in order to develop the optimal conditions, the influence of the different parameters on the coupling reaction was studied. The effect of the ionic matrix, the temperature and the counter-ion of the ionic support was therefore studied.

These different studies were carried out using phenylboronic acid and palladium acetate as catalyst, according to the following reaction diagram:

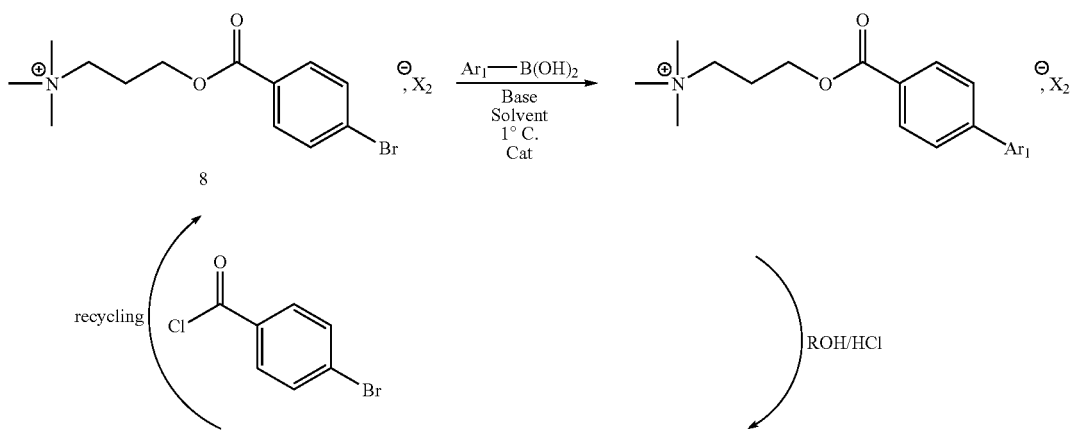

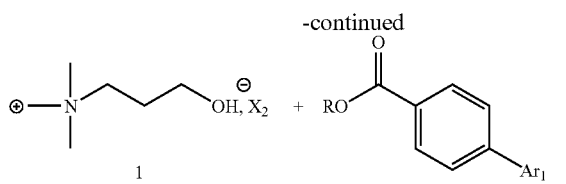

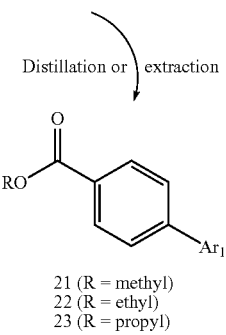

21 (R = methyl)
22 (R = ethyl)
23 (R = propyl)

1—Effect of the Matrix:

The coupling reaction was carried out with N,N,N-trimethylpropylammonium 4-bromobenzoate bis-trifluoromethane sulphonamide and solid $K_2CO_3$ or $K_2CO_3$ in aqueous solution as base. The results obtained after 18 hours of stirring at ambient temperature are shown in the following Table IX:

Examination of the preceding table shows that the use of the matrices with the bis-trifluoromethanesulphonamide ($NTf_2$) anion makes it possible to observe better reactivity compared with the use of hexafluorophosphate ($PF_6$) as anion (compare tests 3 and 4). Similarly, in the case of the matrices composed of ammonium and phosphonium cations,

TABLE IX

| test | Matrix | Conversion rate (%) | Ar-Ar' (%) | Ar-Ar (homocoupling) (%) |
|---|---|---|---|---|
| 1 | $Me_3N^+\frown\frown$, $NTf_2^-$ | 45.5 | 34.9 | 10.6 |
| 2 | $Me_3N^+\frown\frown OH$, $NTf_2^-$ | 76.5 | 64.9 | 10.6 |
| 3 | [1-methyl-3-butylimidazolium], $NTf_2^-$ | 62.3 | 51.6 | 10.7 |
| 4 | [1-methyl-3-butylimidazolium], $PF_6^-$ | 20 | < to 2% | 2.2 |
| 5 | [1-methyl-3-pentylimidazolium], $PF_6^-$ | 20.7 | < to 2% | 4.73 |
| 6 | [1-methyl-3-ethylimidazolium], $NTf_2^-$ | 30.2 | 19.7 | 10.56 |
| 7 | $^+P(C_6H_{13})_3C_{14}H_{29}$; $NTf_2^-$ | 50.7 | 47.9 | 3.3 |
| 8 | $(Bu)_3P^+—Me$  $NTf_2^-$ | 73 | 62.4 | 8.45 | reactivity is distinctly better than that observed in the case of the imidazolium cations (compare tests 2, 8 and 3, 4, 5).

It should however be noted that the presence of an alcohol function on the ionic matrix also makes it possible both to improve the conversion rate from 45 to 76% and to reduce the level of the homocoupling product from 10 to 1% (compare tests 1 and 2).

Finally, this preliminary study shows that the nature of the ionic matrix influences reactivity. Thorough study allows the choice of an appropriate matrix.

2—Effect of the Support Anion, the Temperature and the Base:

In this part, we are interested in studying the influence of a few parameters on the reactivity of substrates supported on an ionic support. All things being equal besides, the temperature, the base and/or the medium were varied.

The different tests carried out are shown in the following Table X:

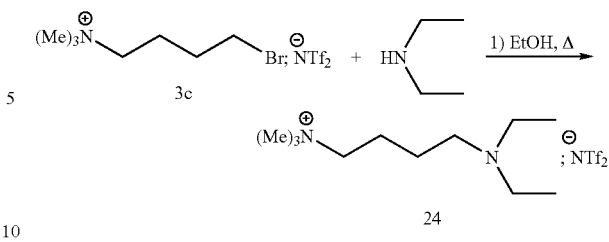

In order to have a conclusive comparative study the reaction time was reduced to 10 hours in the tests carried out at ambient temperature (tests 1 to 8), and to 5 hours for those taken to 80° C. (test 11).

Tests 1 to 4 show that the reactivity of the functionalized salts (ionic supports) the anion of which is tetrafluoroborate or hexafluorophosphate is much greater than that observed

TABLE X

| test | $X_2$ | T (° C.) | base | Solvent or liquid matrix[ii] | Conv. rate (%) | Ar-Ar' (%) | Ar-Ar (%)[i] |
|---|---|---|---|---|---|---|---|
| 1 | $NTf_2$ | 20 | $K_2CO_3(s)$ | $Me_3N^+\!\!\sim\!\!\sim\!\!OH, NTf_2^-$ | 28.0 | 20.6 | 7.4 |
| 2 | $PF_6$ | 20 | $K_2CO_3(s)$ | $Me_3N^+\!\!\sim\!\!\sim\!\!OH, NTf_2^-$ | 100 | 91.6 | 8.4 |
| 3 | $BF_4$ | 20 | $K_2CO_3(s)$ | $Me_3N^+\!\!\sim\!\!\sim\!\!OH, NTf_2^-$ | 100 | 99.0 | 0.1 |
| 4 | Cl | 20 | $K_2CO_3(s)$ | $Me_3N^+\!\!\sim\!\!\sim\!\!OH, NTf_2^-$ | 23.4 | 16.2 | 7.1 |
| 5 | $NTf_2$ | 20 | $K_2CO_3(l)$ | $Me_3N^+\!\!\sim\!\!\sim\!\!OH, NTf_2^-$ | 65.0 | 55.1 | 9.8 |
| 6 | $NTf_2$ | 20 | NaOAc(s) | $Me_3N^+\!\!\sim\!\!\sim\!\!OH, NTf_2^-$ | 30.1 | 25.4 | 4.6 |
| 7 | $NTf_2$ | 20 | TEA[iii] | $Me_3N^+\!\!\sim\!\!\sim\!\!OH, NTf_2^-$ | 63.0 | 56.1 | 6.9 |
| 8 | $NTf_2$ | 20 | TEAS[iv] | $Me_3N^+\!\!\sim\!\!\sim\!\!OH, NTf_2^-$ | 59.3 | 50.5 | 8.9 |
| 11 | $NTf_2$ | 80 | $K_2CO_3(s)$ | $Me_3N^+\!\!\sim\!\!\sim\!\!OH, NTf_2^-$ | 40.6 | 26.5 | 14.1 |

[i]Homocoupling product.
[ii]the functionalized salt is used pure and serves as ionic matrix.
[iii]TEA: triethylamine.
[iv]TEAS: tertiary amine of formula: $Me_3N^+(CH_2)_2CH_2NEt_2$, $NTf_2^-$ During this study N,N',N"-trimethyl-3-hydroxypropylammonium bis-trifluoromethanesulphonamide was used as matrix. In contrast, in the case of the use of DMF as solvent, the ionic support is used pure, i.e. the salt functionalized by the 4-bromobenzoate group is dissolved in pure DMF. During this study in addition to the standard bases, triethylamine supported on a salt (TEAS) was used, which was synthesized by simple condensation of diethylamine on the salt (3c) according to the following reaction diagram:

with a chloride or bis-trifluoromethanesulphonamide anion. The fact that all the ionic supports are dissolved in the same matrix proves that, from the point of view of the mechanism, it is the ionic part of the support which is probably involved at the level of the palladium. This observed reactivity is moreover accompanied by a very great selectivity in the case of the tetrafluoroborate anion.

In addition to the results already observed during the study of the effect of the matrix, tests 1 to 4 show that the mixture of salts carrying different cations or anions do not at all reduce either the reactivity or the selectivity, which offers a wide choice and makes it possible to reduce the cost of the cations and of anions which is sometimes considerable: a chloride costs perhaps 50 times less, for example, than a triflimide.

It is also noted that the presence of water in the medium distinctly increases the reaction speed. In fact, the conversion rate passes from 28 to 64% in the presence of solid $K_2CO_3$ and of a solution of $K_2CO_3$ in water (tests 1 and 5) respectively, which can be explained by better homogeneity of the medium in the presence of water. Similarly, the use of triethylamine as base makes it possible to observe a reactivity comparable to that in the presence of water (compare tests 5 and 7). The grafting of the latter on an ionic support does not influence its reactivity too much. In fact, the result obtained during test 8 is comparable to that of test 7, whether in terms of reactivity or in terms of selectivity. This represents a major result, knowing that recycling of this form of base is easy. In fact, a simple washing with a basic solution makes it possible to regenerate the TEAS, which will therefore simultaneously reduce the cost and harmful waste.

3—Application in Combinatorial Chemistry:

This library of biaryl esters was prepared by operating as in the case of Example 1.

In a first phase we carried out a series of coupling reactions in parallel with 9 arylboronic acids and supported 4-bromobenzoic acid. Then, the 9 reactions were mixed in order to form a homogeneous solution, which was then divided into three equal portions, after which each of the solutions was solubilized in an alcohol. Then a few drops of concentrated hydrochloric acid (12 N) were added and the alcohol was taken to reflux for 18 hours. After evaporation of the alcohol, the mixture of the biarylesters was extracted with ether. 3 series of 9 esters were therefore obtained which were then analyzed by GC/MS. The different expected biarylesters were all identified without ambiguity.

All the results are represented in the form of tables below. A chromatogram corresponding to the mixture of the biaryl propyl esters is represented below.

1/Biaryl Propyl Esters:

Table XI hereafter corresponds to the chromatogram of FIG. 7.

TABLE XI

Library of the propyl esters 23

| R | Retention time in minutes and seconds | Molecular mass |
|---|---|---|
| 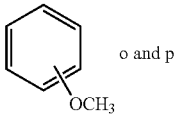 o and p OCH$_3$ | 26.42; 27.36 | 270 |
| 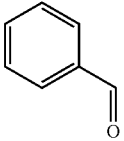 O | 28.13 | 268 |
| 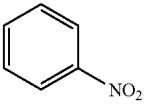 NO$_2$ | 32.29 | 285 |

TABLE XI-continued

Library of the propyl esters 23

| R | Retention time in minutes and seconds | Molecular mass |
|---|---|---|
| 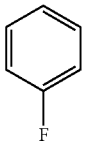 F | 19.28 | 258 |
| 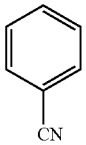 CN | 28.96 | 265 |
| 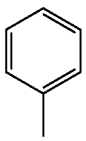 | 22.82 | 254 |
|  | 19.53 | 240 |
| 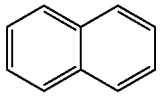 | 34.52 | 290 |

2/Biaryl Methyl Esters:

TABLE XII

Library of the methyl esters

| R | Retention time | Molecular mass |
|---|---|---|
| 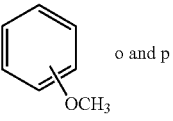 o and p OCH$_3$ | 21.31; 22.35 | 242 |
| 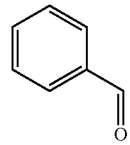 O | 23.24 | 240 |
| 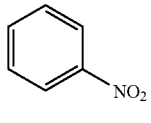 NO$_2$ | 28.58 | 257 |
| 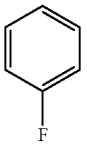 F | 16.28 | 230 |

TABLE XII-continued

Library of the methyl esters

| R | Retention time | Molecular mass |
|---|---|---|
| (phenyl-CN) | 24.23 | 237 |
| (phenyl-CH3) | 18.25 | 226 |
| (phenyl) | 16.41 | 212 |
| (naphthyl) | 27.74 | 262 |

3/Biaryl Ethyl Esters:

TABLE XIII

Library of the ethyl esters

| Ar | Retention time | Molecular mass |
|---|---|---|
| (phenyl-OCH3, o and p) | 23.76; 24.73 | 256 |
| (phenyl-CHO) | 25.19 | 254 |
| (phenyl-NO2) | 28.72 | 271 |
| (phenyl-F) | 17.33 | 244 |

TABLE XIII-continued

Library of the ethyl esters

| Ar | Retention time | Molecular mass |
|---|---|---|
| (phenyl-CN) | 25.95 | 251 |
| (phenyl-CH3) | 19.82 | 240 |
| (phenyl) | 17.50 | 226 |
| (naphthyl) | 30.12 | 276 |

B—Supported Aryl Halide:

In a second phase, an attempt was made to graft an arylboronic acid on a salt in order to involve it in a Suzuki coupling reaction. This study can be carried out according to two different approaches:

- the first one is to support an arylboronic acid on the cation of the salt functionalized by diethanolamine in order to form boratranes (see below):

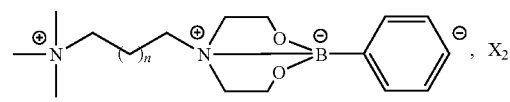

- the second one is to support it by means of the anion of the functionalized salt. In fact, if the $X_2^-$ anion of the functionalized salt serving as support is nucleophilic enough, it will react with phenylboronic acid, quaternizing the boron atom in order to produce a borate:

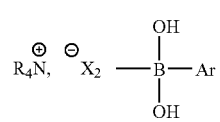

I—Functionalized Cation Salt:
1) Synthesis of the Functionalized Salts:
The functionalized salts were synthesized according to the following reaction diagram:

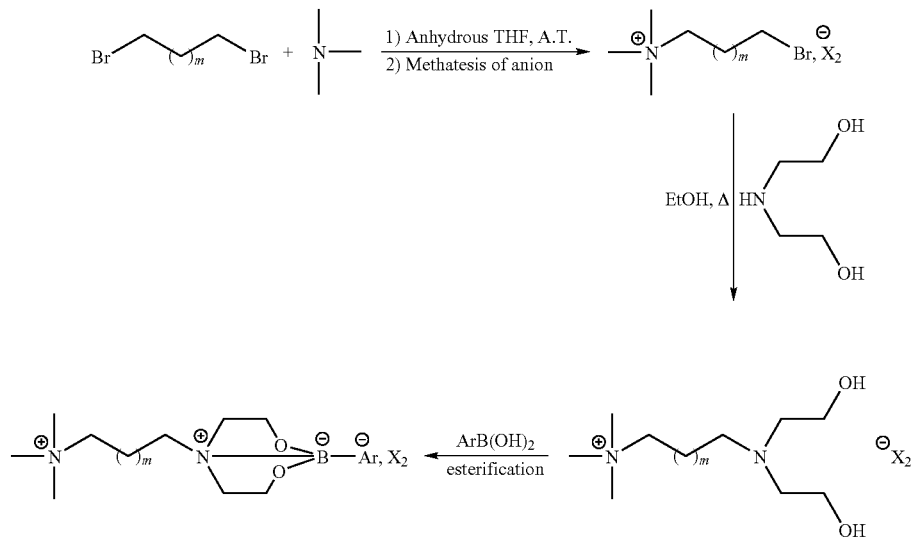

The condensation reaction of trimethylamine on an alkyl dibromide is carried out under anhydrous conditions with very good yields (>95%). The ammonium bromide thus obtained undergoes an anion-exchange reaction (metathesis) under standard conditions. The second stage was carried out in the presence of an equivalent of diethanolamine with a quantitative yield. Similarly, the stage of grafting of the arylboronic acid was carried out with good yields and makes it possible to obtain a product in two different forms. In fact, as a function of the solvent and of the anion of the support, equilibrium is or is not obtained between the tri- and tetravalent borons. Thus, if the operation is carried out in THF and in the presence of a bis-trifluoromethanesulphonamide anion the equilibrium obtained is 80/20 in favor of the tetravalent boron. Conversely, the use of an ether, chloroform and isopropanol mixture exclusively leads to the tetravalent boron (boratrane). Under the same conditions and in the presence of the tetrafluoroborate anion, a 60/40 equilibrium is obtained in favor of the trivalent boron, according to the following diagram:

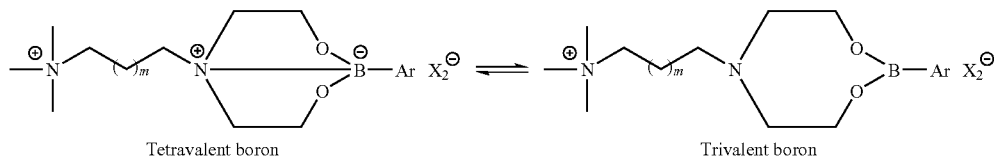

It should be noted that the chemical shifts of the boron obtained depend on the nature of the anion. In fact, in the case of bis-trifluoromethanesulphonamide the signal of the tetravalent boron appears at 13.06 ppm. On the other hand, with the tetrafluoroborate anion it appears at 4 ppm. This shows that the nature of the counter-ion also influences the nature of the bond between the nitrogen and boron atoms, and therefore the transfer of electrons from the nitrogen to the boron.

Then, the synthesized boratranes were involved in the Suzuki coupling reaction according to the following reaction diagram:

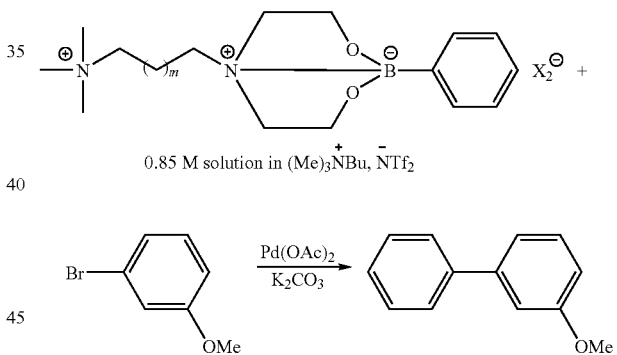

A solution of boratrane (0.85 mol/l) in N,N',N''-trimethylbutylammonium bis-trifluoromethanesulphonamide serving as matrix is brought into contact with 1-bromo-3-methoxybenzene, in the presence of solid $K_2CO_3$ as base and palladium acetate as catalyst. The mixture is heated at 80° C. for 18 hours. The results obtained are shown in the following Table XIV:

TABLE XIV

| test | boratrane | Conversion rate | Yield (biphenyl-OMe) | Homo-Coupling (biphenyl) |
|------|-----------|-----------------|-----------------------|--------------------------|
| 1 | [structure], NTf2 | 72% | 66.8% | 5.1% |
| 2 | [structure], PF6 | 82% | 64.4% | 18.0% |
| 3 | [structure], BF4 | 54% | 32.3% | 22.1% |

The preliminary tests which were carried out show that the supported boronic acids can be subjected to Suzuki coupling. In contrast, this reaction requires an energy supply, as at ambient temperature no reaction was observed for the different substrates.

On the other hand, at 80° C. as indicated in the preceding table the reaction takes place and depends on the nature of the counter-ion of the support. The influence of the latter on selectivity (test 1 and 2) is also noted. It should however be pointed out that this reactivity can be influenced by the nature of the equilibrium existing between the tri- and tetravalent borons, which can explain the weak reactivity of the boratrane possessing the tetrafluoroborate as counter-ion compared with that observed in the case of the presence of an equilibrium displaced towards the tetravalent boron (case of bis-trifluoromethane sulphonamide).

II—Functionalized Anion Salt:

In the preceding case, the cationic part of the salt with a dedicated task was functionalized in order to support an arylboronic acid in the form of a boratrane with a tetravalent boron atom. The latter represents the intermediate species in the Suzuki coupling reaction. It is also possible to envisage the use of salts with nucleophilic anions ($OH^-$ and $F^-$) capable of quaternizing the boron atom of arylboronic acid in order to produce borates, derivatives of tetravalent boron, an intermediate in the Suzuki coupling reaction. The following commercial ammonium salts were therefore used:

tetrabutylammonium hydroxide:

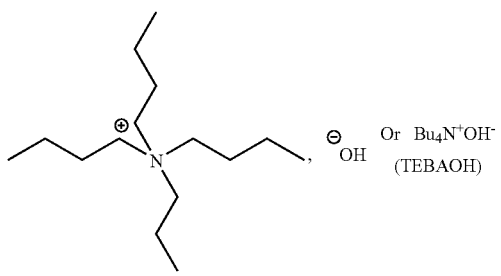

tetramethylammonium fluoride:

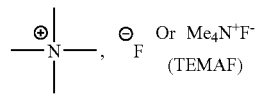

1) Case of $Bu_4N^+OH^-$:

The synthesis of the supported substrate is carried out according to the following reaction diagram:

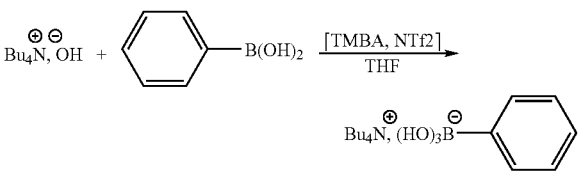

The $Bu_4N^+OH^-$, dried under vacuum after evaporation of the water, is solubilized in the TMBA bis-trifluoromethane-sulphonamide serving as matrix in order to produce a 0.85 mol/l solution. A stoichiometric quantity of phenylboronic acid in solution in anhydrous THF is added to this solution at ambient temperature. The monitoring of the reaction by $^{11}B$ NMR after evaporation of the THF shows that it is complete after two hours. A single signal is then observed at 3.97 ppm corresponding to a borate.

2) Case of $Me_4N^+F^-$:

In the same manner as in the case of the hydroxide, the phenylboronic acid is quaternized by $Me_4N^+F^-$ according to the following diagram:

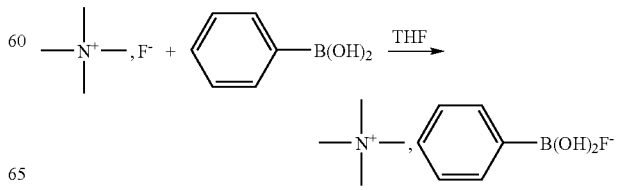

For this reaction, the salt was solubilized in THF (anhydrous) at ambient temperature, then phenylboronic acid was added. After 18 hours of stirring of the mixture at ambient temperature, the precipitate which forms is filtered then washed with ether. The yield of isolated product depends on the quantity of phenylboronic acid used. In fact, in the presence of an excess of the latter, an 82% yield is obtained. On the other hand a deficiency causes it to drop to less than 50%. The monitoring of this reaction is carried out using NMR of the boron and of the fluorine. Table XV below shows the results obtained:

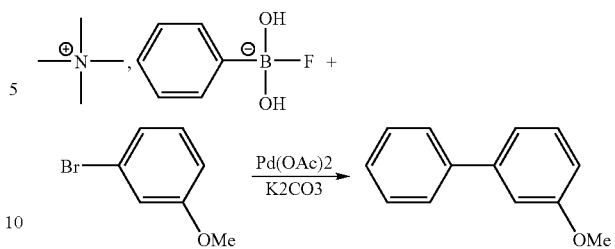

The reaction was carried out at two distinct temperatures in order to study the effect of the temperature both on reactivity, and on selectivity. See Table XVI hereafter:

TABLE XVI

| test | T° C. | Conversion rate in (%) | <img> Yield | <img> Yield |
|---|---|---|---|---|
| 1 | AT | 92.4% | 86.3% | 5.7% |
| 2 | 80° C. | 96% | 77.7% | 18.3% |

TABLE XV

| test | number of boronic acid equivalents | Yield (%) | NMR Analyses |
|---|---|---|---|
| 1 | 1 eq | 65% | $^{11}$B NMR Spectrum: (Acetone), δ ppm: $B_4$ = 4.66 ppm (60%) $B_3$ = 28.5 ppm (40%) $^{19}$F NMR Spectrum: (Acetone), δ ppm: −136.4 ppm |
| 2 | 0.75 eq | 48% | $^{11}$B NMR Spectrum: (Acetone), δ ppm: $B_4$ = 4.76 ppm (60%) $B_3$ = 28.5 ppm (40%) $^{19}$F NMR Spectrum: (Acetone), δ ppm: −136.05 ppm |
| 3 | 2 eq | 82% | $^{11}$B NMR Spectrum: (Acetone), δ ppm: $B_4$ = 4.4 ppm (60%) $B_3$ = 28.5 ppm (40%) |

In the different cases, the NMR of the boron shows the presence of an equilibrium between the tri- and tetravalent forms and in favor of the latter (Diagram)

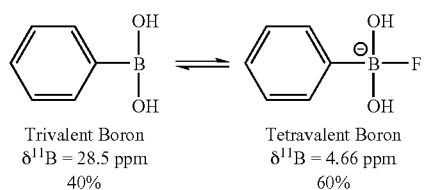 [SMILES: OB(O)c1ccccc1 ; O[B-](O)(F)c1ccccc1]

Trivalent Boron  Tetravalent Boron
$δ^{11}B$ = 28.5 ppm  $δ^{11}B$ = 4.66 ppm
40%  60% a/—Suzuki Coupling Reactions with [TEMA][PhB(OH)$_2$F]:

The protocol is the same as that used in the preceding part and is carried out according to the following reaction diagram:

It is noted that the yield obtained at 80° C. is close to that obtained at ambient temperature. By contrast, the percentage of homocoupling product is less at ambient temperature than at 80° C. (tests 1 and 2).

b—/Coupling Reaction with [TEBA][PhB((OH)$_3$]:

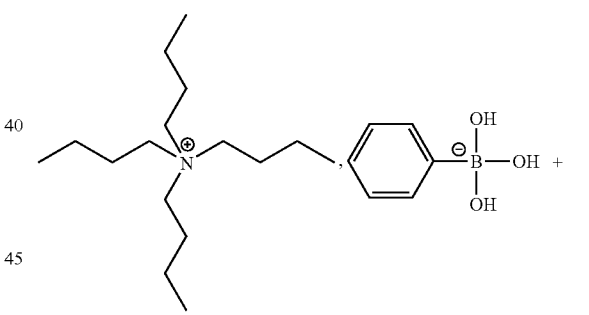

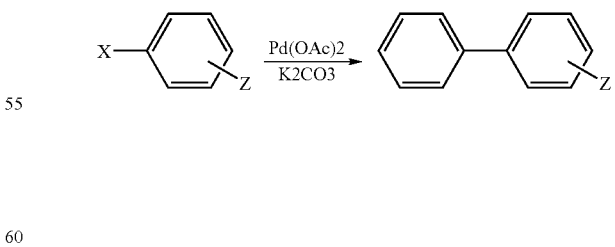

As in the preceding cases, the same protocol was used and the best operating conditions were developed in order to be able to initiate a combinatorial chemistry test.

For this purpose, the influence of several parameters was tested, namely temperature and the addition of a solvent such as DMF.

The results are shown in the following Table XVII:

TABLE XVII

| test | Aryl | Conversion rate | T (° C.) | solvent | Yield (biphenyl-OMe) | Yield (biphenyl) |
|---|---|---|---|---|---|---|
| 1 | Br—C6H4—OMe (3-bromoanisole) | 51% | 40 ° C. | [TMBA][X⁻] | 44.2% | 6.4% |
| 5 | I—C6H4—OMe (4-iodoanisole) | 66% | AT | [TMBA][X⁻] | 55.4% | 10.2% |

Example 5

Use of the Solid [Matrix+Functionalized Salt] Combination at Ambient Temperature In the different examples that we have studied to date, only ionic matrices which are liquid at ambient temperature have been used. However, the possibility of using a matrix which is solid at ambient temperature has been tested and demonstrated.

In fact, the use of an ionic liquid the melting temperature of which is higher than ambient, diversifies the choice of matrix and broadens the scope of the OSSIL principle. Matrices which are solid at ambient temperature can have a very considerable additional benefit: the crystallization of the medium simplifies the recovery of both the excess of reagents and the reaction products. The choice of the solid matrix can be carried out according to the following criteria:

- in the absence of standard organic solvent, the melting point of the functionalized ionic salt/ionic matrix mixture must be below the reaction temperature,
- in the presence of a standard organic solvent, a matrix with a dedicated task (ionic matrix+functionalized salt) must preferably be soluble in the solvent.

In order to illustrate this example the Heck coupling test was carried out using a matrix which is solid at ambient temperature, according to the following diagram:

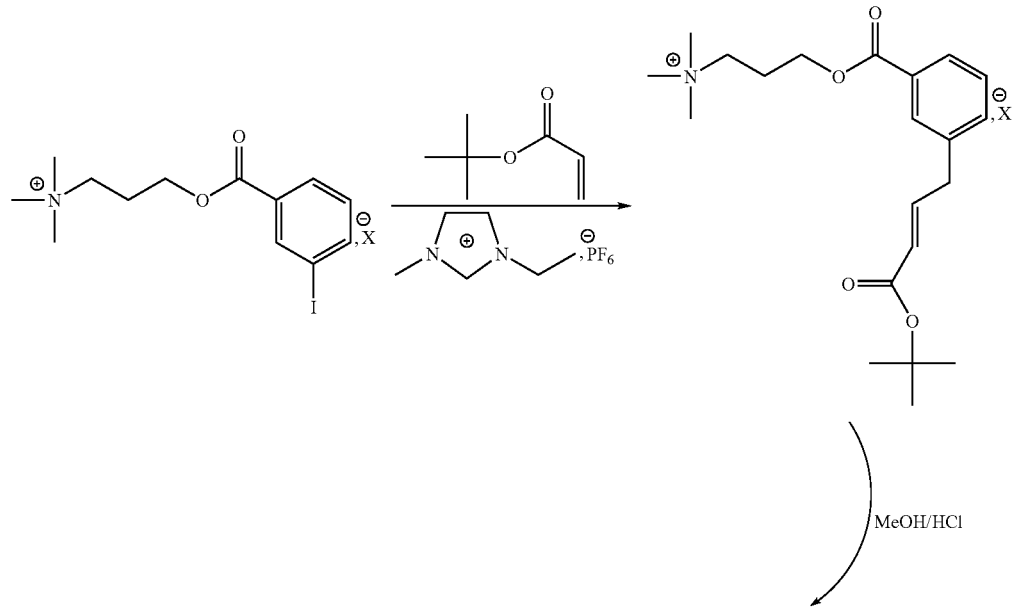

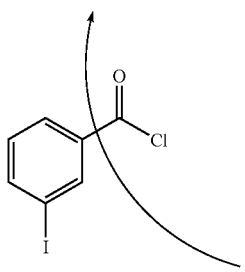
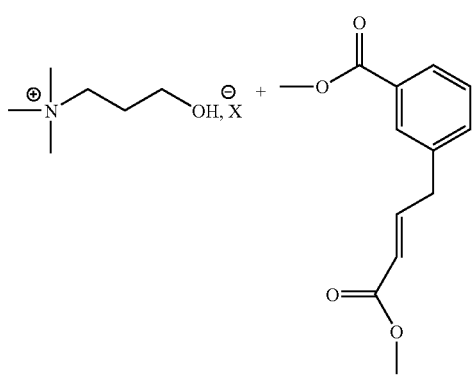

In this test the Heck coupling was carried out using supported aryl iodide as substrate and tert-butyl acrylate as alkene under the same conditions as those described in the examples where ionic matrices which are liquid at ambient temperature were used.

In this case N-methyl, N'-ethylimidazolium hexafluorophosphate (EMIM, $PF_6$) was used as ionic matrix, the melting point of which is of the order of 56° C.

Procedure:

1 mmol of functionalized ionic salt (7a) is mixed with 1 g of the ionic matrix and heated to 70° C. in order to obtain a solution. On cooling down, this homogeneous mixture is solid at ambient temperature. On reheating and from 65° C., the medium again becomes liquid and completely homogeneous. The base and the catalyst are added to this solution like for the different tests mentioned above, followed by heating to 80° C. After 5 hours the $^1$H NMR of the mixture shows complete disappearance of the starting iodide.

The reaction mixture is cooled down to ambient temperature and a heterogeneous (solid/liquid) mixture is obtained. Then, ether is added and the solid is filtered out, then washed again in order to extract all of the acrylate. The product is then released from the functionalized salt by transesterification according to the procedure described in the different examples mentioned above. After elimination under vacuum of the excess methanol, the cinnamic ester is isolated by the addition of ether and filtration of the solid mixture constituted by the functionalized salt and the starting solid matrix which can be reused.

In conclusion this test shows that the application of the OSSIL principle to ionic matrices with a dedicated task, which are solid at ambient temperature is perfectly possible, and as a result makes it possible to broaden the choice of the nature of the anion. Moreover, this system with a mixture which is solid at ambient temperature opens up new horizons and in addition will make it possible to easily adapt the OSSIL principle to all the technologies already developed in the case of solid supports.

The very wide variety of easily accessible onium salts and more particularly phosphonium, ammonium, pyridinium and imidazolium salts will be noted.

Example 6

Sonogashira Coupling

Another example of coupling where the OSSIL principle was tested is that of Sonogashira which consists of a coupling of an aryl halide and a true alkyne.

This study was carried out supporting 4-iodobenzoic acid on a salt with a dedicated task. Several tests are carried out for the purpose of determining the influence of the nature of the anion of the support and that of the matrix on this coupling reaction (see diagram below).

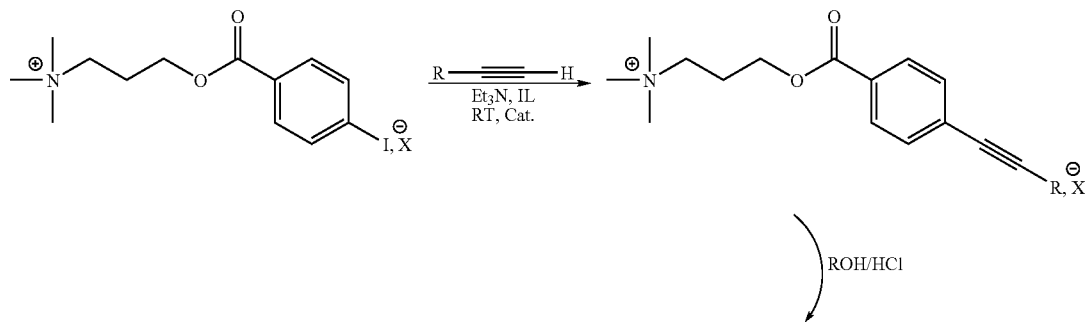

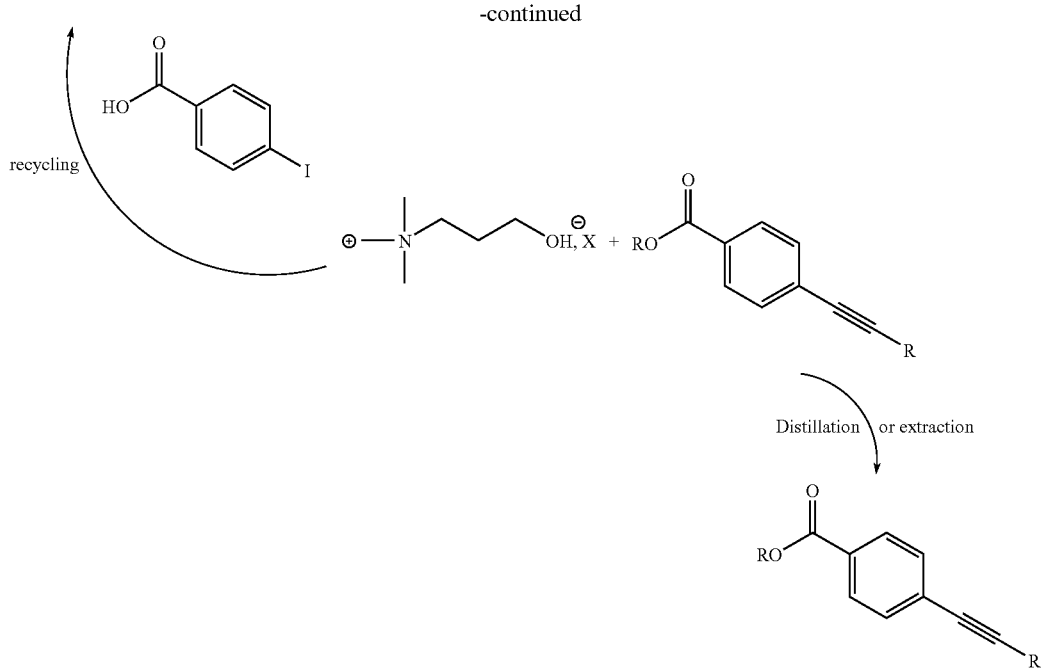

The results shown in Table XIX below were determined by means of monitoring of the reactions by $^1$H NMR.

TABLE XIX

| Input | X | R | matrix | Time (h) | Conv. (%) | Yield (%) |
|---|---|---|---|---|---|---|
| 1 | OTf | Ph | [tmba][NTf$_2$] | 1 | 75 | 72 |
| 2 | NTf$_2$ | Ph | [tmba][NTf$_2$] | 1 | 78 | 77 |
| 3 | NTf$_2$ | Ph | [bmim][BF$_4$] | 1 | 70 | 66 |
| 4 | NTf$_2$ | Ph | [tmba][NTf$_2$] | 2 | 100 | 95 |
| 5 | NTf$_2$ | CH$_3$OCH$_2$ | [tmba][NTf$_2$] | 2 | 92 | 92 |
| 6 | NTf$_2$ | CH$_3$(CH$_2$)$_3$ | [tmba][NTf$_2$] | 2 | 100 | 98 |
| 7 | NTf$_2$ | CH$_3$(CH$_2$)$_4$ | [tmba][NTf$_2$] | 2 | 94 | 90 |
| 8 | NTf$_2$ | CH$_3$(CH$_2$)$_6$ | [tmba][NTf$_2$] | 2 | 93 | 88 |

[tmba] = [Me$_3$N$^+$-Bu]
[bmim] = butylmethylimidazolium

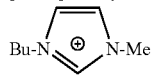

The results shown in the table show that the nature of the anion of the support and of the matrix does not influence the reaction speed and the yields of isolated product too much. FIG. 11 illustrates the simplicity of the monitoring of the reaction by proton NMR (Case of R=Ph).

The cleavage of the products after coupling was carried out by two transesterification processes, one by methanol, the other by ethanol. For this purpose the products of tests 4, 5, 6, 7 and 8 are mixed and reacted according to the "split-and-mix" principle in the presence of alcohol and a catalytic quantity of hydrochloric acid. This stage also allows the recycling of the salt with a dedicated task as well as that of the matrix used for the reaction.

After 12 hours the two reactions are complete, the products are isolated by extraction with ether then injected into GC/MS. In both cases the four products were detected.

1/Methyl Esters:

Table XX hereafter corresponds to the chromatogram of FIG. 12.

TABLE XX

Library of the methyl esters

| R | Retention time in minutes | Molecular mass |
|---|---|---|
| CH$_3$-O-CH$_2$- | 14.57 | 204 |
| CH$_3$(CH$_2$)$_3$- | 15.35 | 216 |
| CH$_3$(CH$_2$)$_4$- | 16.56 | 230 |
| CH$_3$(CH$_2$)$_6$- | 20.53 | 236 |
| Ph- | 21.16 | 258 |

2/Ethyl Esters:

The table XXI hereafter corresponds to the chromatogram of FIG. 13.

TABLE XXI

Library of the ethyl esters

| R | Retention time in minutes | Molecular mass |
|---|---|---|
| CH₃CH₂—O—CH₃ | 15.24 | 218 |
| (CH₂)₃—CH₃ | 16.18 | 230 |
| (CH₂)₄—CH₃ | 17.68 | 244 |
| (CH₂)₆—CH₃ | 22.77 | 250 |
| phenyl | 23.57 | 272 |

Procedure:

Alkyne (0.64 mmol) and copper iodide (0.8 mg; 0.04 mmol) are added to a mixture constituted by a 0.85 M solution of [3-(4-iodobenzoyloxy)-propyl]-trimethylammonium (100 mg; 0.156 mmol) in an ionic liquid (matrix) and triethylamine (0.92 ml), followed by stirring at ambient temperature for 5 minutes then the palladium complex PdCl₂(Ph₃P)₂ (1.4 mg; 0.02 mmol) is added. The reaction medium is left under stirring at ambient temperature for 2 hours. The medium is then washed several times with ether and dried under vacuum.

Example 7

Multi-Component Reactions (MCRs)

Multi-component reactions simultaneously bring at least three reaction partners into contact under experimental conditions which do not vary over time and allow the creation of several covalent bonds in a single stage, unlike standard reactions where two reagents lead to a product by the creation of new bonds. Thus it is possible to access a highly functionalized molecule from relatively simple entities in a single stage. Moreover, the MCRs combine convergence and economy of atoms, two fundamental principles in organic synthesis which are important for combinatorial chemistry. Finally it should be pointed out that these reactions generally take place with a high yield, since they avoid the succession of stages which, at each step, causes the yield to drop.

The best known and most highly developed MCRs are those of Passerini and Ugi (Ugi, 1976). One of the key elements of these reactions is an isonitrile, the electronic structure of which, comprising a doublet and an electron hole, allows the passage of a formally divalent carbon atom to a tetravalent carbon atom by adding an electrophile and a nucleophile. The diagram below presents an example of a Passerini reaction.

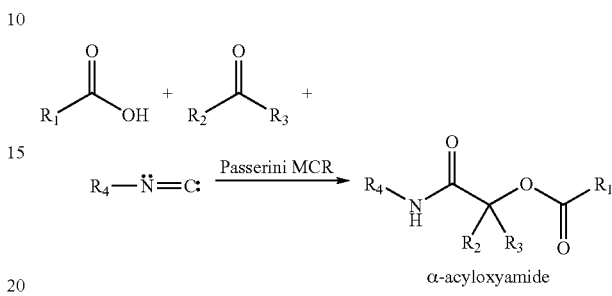

Of course the MCRs were transposed onto solid support, for example a resin with an amine termination was used in an Ugi-type reaction in order to produce, after cleavage, a series of high-purity adducts with yields ranging from average to excellent (see diagram below) (Lhoel and Nielsen, 1999).

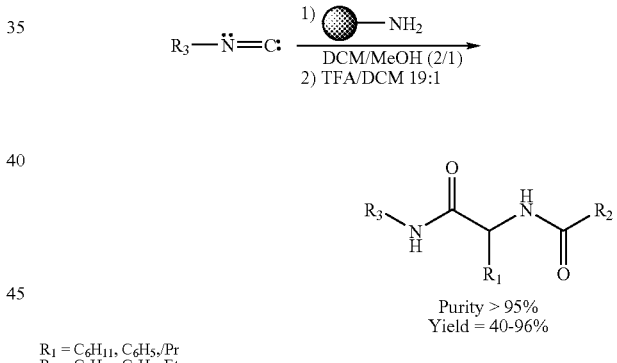

Although the Ugi and Passerini reactions are the best known and most highly developed, other MCRs exist, which correspond to the essential criteria, namely: all the reagents are present from the start of the reaction and the conditions do not vary during the latter. Unlike the Ugi and Passerini reactions, these other reactions are not based on the use of an isonitrile as one of the central players in the creation of new covalent bonds. These different types of reactions make it possible to access highly functionalized varying structures in a single stage.

The substituted quinolines are useful pharmacophores. Their synthesis on solid support was carried out by a so-called Doebner MCR, involving an aniline, an aldehyde and an α-dicarbonylated compound (see diagram hereafter) (Gopalsamy and Pallai, 1997). The quinolines are obtained with a high purity and very good yields.

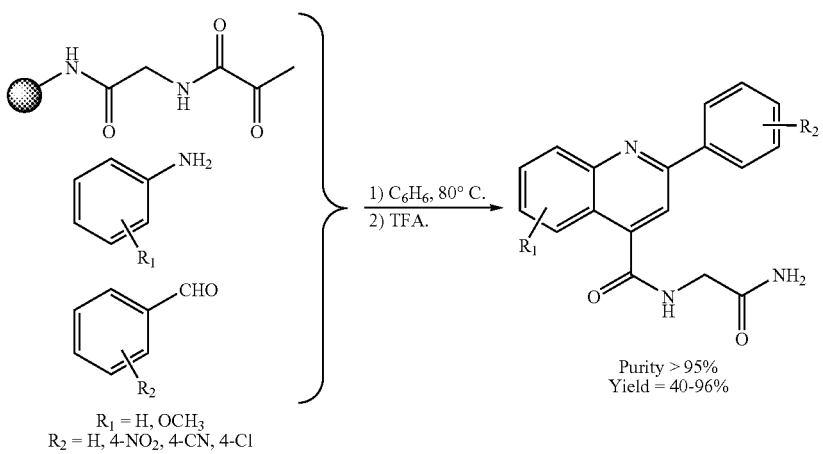

The principle of the present invention was applied within the framework of Grieco-type MCRs (Grieco and Bahas, 1988). This example has been the subject of several works described by W. Armstrong et al. (Kiselyov et al., 1998) on solid support and it has allowed the preparation of a library of 80 products with yields ranging from 50 to 93%.

In order to do this, the aniline 1 was supported and used with an aldehyde and cyclopentadiene in the presence of butyltrimethylammoniumtriflimide as matrix in order to produce tetrahydroquinolines (see diagram hereafter). This example with three components, consists of a first condensation of the aldehyde and the aniline in order to produce the imine. The latter then reacts in what is formally a Diels-Alder reaction with cyclopentadiene in the presence of a catalytic quantity of trifluoroacetic acid.

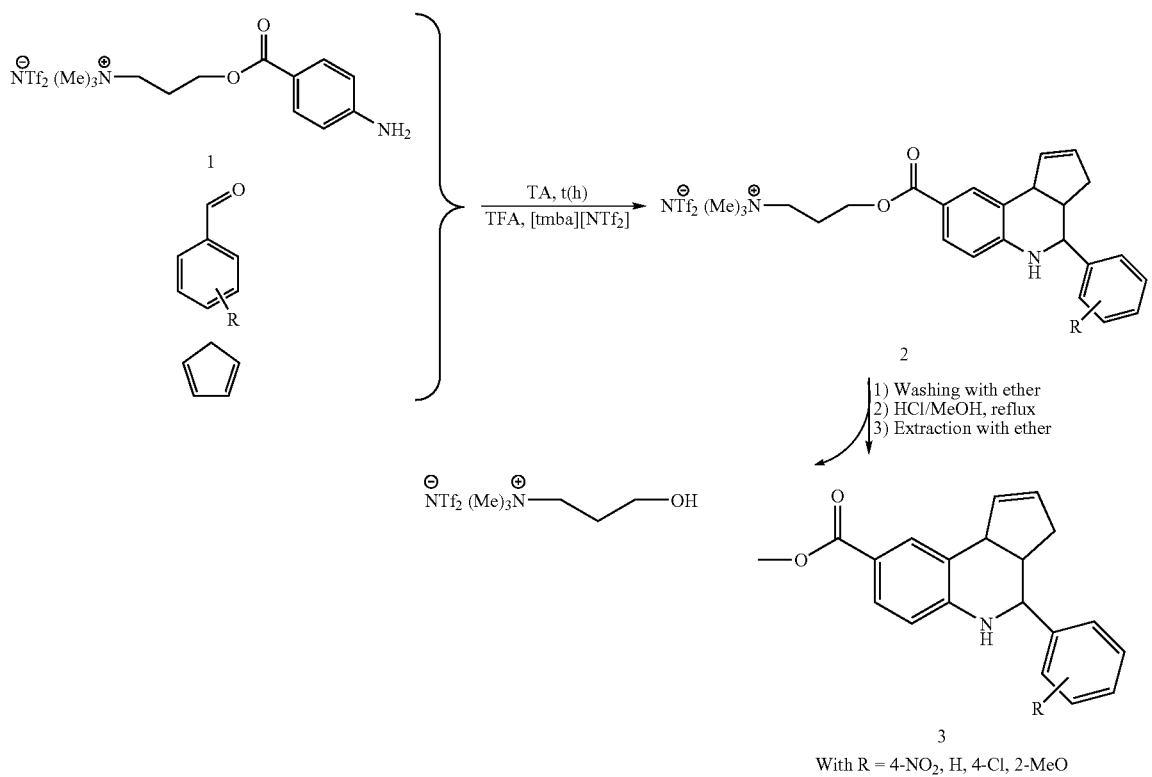

The monitoring of the different reactions was carried out by $^1$H NMR and we observed conversion ranging from 80% to 100% according to the nature of the aldehyde. Thus, in the presence of 4-nitrobenzaldehyde, the reaction is complete at the end of 30 minutes whereas it is only 75% in the case of 4-methoxy-benzaldehyde (electron-rich aldehyde). FIG. 10 illustrates the case of 4-nitrobenzaldehyde, after washing with ether in order to eliminate the excess of the two reagents and the trifluoroacetic acid. This figure also shows that the monitoring of a reaction which leads to complex compounds is possible and with remarkable clarity. It should also be noted that transesterification by methanol leads to very clean products which are extracted with ether and purified by filtration on silica.

The different examples carried out and the results obtained are shown in Table XVIII below.

TABLE XVIII

| R | matrix | reaction time (min) | conversion rate (%) |
|---|---|---|---|
| H | [tmba][NTf$_2$] | 30 | 100 |
| H | [C$_3$OHtma][NTf$_2$] | 30 | 100 |
| NO$_2$ | [tmba][NTf$_2$] | 30 | 100 |
| Cl | [tmba][NTf$_2$] | 30 | 100 |
| Br | [tmba][NTf$_2$] | 30 | 100 |
| OMe | [tmba][NTf$_2$] | 75 | 82 |

[tmba] = [Me$_3$N$^+$—Bu]
[C$_3$OHtma] = [Me$_3$N$^+$—(CH$_2$)$_2$CH$_2$OH]

During this work no effect of the nature of matrix was observed. On the other hand, the presence of the latter distinctly influences the reaction speed and allows complete conversion in less than an hour, whereas, in the case of the works described in the literature on solid support, this conversion rate is obtained only after 12 hours.

Procedure of the Grieco Reaction:

A 0.85 M solution of [3-(4-aminobenzoyloxy)-propyl]-trimethylammonium (100 mg; 0.2 mmol) in an ionic liquid (matrix) is placed under vacuum then under argon. Aldehyde (0.5 mmol), cyclopentadiene (132 mg, 2 mmol) and trifluoroacetic acid TFA (20 µl; 0.27 mmol) are added. The mixture is stirred at ambient temperature. At the end of the reaction, the medium is washed several times with ether and dried under vacuum.

The viscous oil obtained is then dissolved in methanol and taken to reflux in the presence of 3 drops of concentrated hydrochloric acid. After 12 hours the product is extracted with ether (2×30 ml) after evaporation of the methanol.

REFERENCES

Abbott P.; Capper, G.; Davies, L.; Rasheed, R. K.; Tambyrajah, V. WO0226701, 2002,
Bayer, E. (1991) *Angew. Chem., Int. Ed. Engl.*, 30, 113-129,
Charken I. M. and Janda K. D. (1996) "Molecular Diversity and Combinatorial Chemistry" American Chemical Society, Washington, D.C.,
Dörwald (2000) Organic synthesis on solid phase, Wiley-VCH, Weinheim,
Fraga-Dubreuil, J.; Bazureau, J. P. (2001) *Tetrahedron Letters*, 42(35), 6097-6100,
Gopalsamy, A.; Pallai, P. V. (1997) *Tetrahedron Lett.*, 38, 907,
Gravet, D. J.; Janda, K. D. (1997) *Chem. Rev.*, 97, 489-510,
Grieco, A.; Bahas (1988) *Tetrahedron Lett.*, 29, 5855,
Howarth, J.; Dallas, A. (2000) *molecules*, 5, 851-855,
Jeffery, Tuyet. (1996) *Tetrahedron*, 52(30),
Kiselyov, A. S.; Smith II, L.; Virgilio, A.; Amstrong, R. W. (1998) *Tetrahedron*, 54, 7987,
Kiselyov, A. S.; Smith II, L.; Amstrong, R. W. (1998) *Tetrahedron*, 54, 5089,
Lhoel, A. M.; Nielsen, J. (1999) *Tetrahedron Lett.*, 40, 3941,
Murphy, Vince; Hagemeyer, Alfred; Poojary, Damodara M. WO0032572, 2000,
O'Brecht, D.; Villalgordo, J. M. (1998) "Supported combinatorial and parallel synthesis of small-molecular weight compound libraries", *Tetrahedron Organic Chemistry Pergamon*, volume 17,
P. Wentworth, Jr. K. D. Janda, (1999) *Chem Comm.*, 1917-24,
Sammelson, R. E.; Kurth, M. (2001) *J. Chem. Rev.*, 101, 137-202,
Thompson, L. A.; Elhman, J. A. (1996) *Chem. Rev.*, 96, 555-600,
Ugi, I. (1976) "Isonitrile", Academic Press, Inc., pp 133-199,
Visser, A. E.; Swatloski, R. P.; Reichert, W. M.; Davis, James H., Jr.; Rogers, R. D.; Mayton, R.; Sheff, S.; Wierzbicki, A. (2001) *Chemical Communications* (2001), (1), 135-136.
Visser, A. E.; Swatloski, R. P.; Reichert, W. M.; Mayton, Rebecca; Sheff, Sean; Wierzbicki, Andrzej; Davis, James H. Jr.; Rogers, Robin D. (2002) *Environmental Science and Technology*, 36(11), 2523-2529,
Wasserscheid, P.; Keim, W. (2000) *Ang. Chem. Int. Ed.*, 39, 3772-3789,
Welton, T. (1999) *Chem. Rev.*, 99, 2071-2083,
Wilson, S. R.; Czarnik, A. W. (1997) "Combinatorial Chemistry: Synthesis and Application"; John Wiley & Sons New York,
Xiao. J.; Chen W.; Xu L. (2000) *Organometallics*, 19, 1123-1127.

The invention claimed is:

1. A method of performing a Heck coupling reaction in a homogeneous phase on a soluble reaction support, without volatile organic solvents, comprising:
   (i) dissolving a soluble reaction support in the form of a functionalized onium salt in a liquid matrix in the form of a ionic liquid of formula $A_1^+X_1^-$ to form a composition, wherein said ionic liquid of formula $A_1^+X_1^-$ is not functionalized;
   (ii) adding at least one reagent to the composition obtained in step (i); and
   (iii) converting the chemical function(s) of said functionalized onium salt to provide a Heck coupling on the soluble reaction support, without volatile organic solvents, wherein,
   said non-functionalized ionic liquid of formula $A_1^+X_1^-$ is in liquid or solid form at ambient temperature,
   $A_1^+$ is a non organic-functional cation or a mixture of non organic-functional cations, and
   $X_1^-$ a non organic-functional anion or a mixture of non organic-functional anions.

2. A method of performing a Heck coupling reaction in a homogeneous phase on a soluble reaction support, without volatile organic solvents, comprising:
   (i) dissolving a soluble reaction support in the form of a functionalized onium salt in a liquid matrix in the form of a ionic liquid of formula $A_1^+X_1^-$ to form a composition, wherein said ionic liquid of formula $A_1^+X_1^-$ is not functionalized,
   (ii) adding at least one reagent to the composition obtained in step (i); and
   (iii) converting the chemical function(s) of said functionalized onium salt to provide a Heck coupling on the soluble reaction support, without volatile organic solvents, wherein,
   said non-functionalized ionic liquid of formula $A_1^+X_1^-$ is in liquid or solid form at ambient temperature,
   $A_1^+$ is a non organic-functional cation or a mixture of cations in which none of the cations is organic functional,
   $X_1^-$ is a non organic-functional anion or a mixture of anions in which none of the anions is organic functional, said soluble reaction support is at least one organic functionalized salt of formula $A_2^+X_2^-$, $A_2^+$ is selected from the group consisting of an organic functional cation, a non organic-functional cation, a mixture of cations in which none of the cations is organic functional, and a mixture of cations in which at least one of the cations is organic functional, $X_2^-$ is selected from the group consisting of an organic functional anion, non organic-functional anion, a mixture of anions in which none of the anions is organic functional, and a mixture of anions in which at least one of the anions is organic functional, and at least one of $A_2^+$ and $X_2^-$ is a organic functional ion, said organic functional cation is of a formula $Y^+$-L-$F_i$, and said organic functional anion is of a formula $Y^-$-$(L)_k$-$F_i$, $Y^+$— and $Y^-$— are ionic entities, the charge of which corresponding to the charge of the cation of formula $Y^-$-L-$F_i$ and the charge of the anion of formula $Y^-$-$(L)_k$-$F_i$, respectively, linked via a linker L to at least one organic function $F_i$, L is an alkyl group of 1 to 20 carbon atoms, $F_i$ varies from $F_0$ to $F_n$, n being an integer varying from 1 to 10, with $F_0$ being an organic function initially linked to said cationic entities and anionic entities and $F_1$ to $F_{10}$ being organic functions converted from said Fo after sequential and subsequent reactions with said cationic or anionic entities, said organic function $F_i$ is selected from the group consisting of hydroxyl, carboxylic, amide, sulphone, primary amine, secondary amine, aldehyde, ketone, ethenyl, ethynyl, dienyl, ether, epoxide, primary phosphine, secondary phosphine, tertiary phosphine, azide, imine, ketene, cumulene, heterocumulene, thiol, thioether, sulphoxide, phosphorus-containing moieties, heterocycles, sulphonic acid, silane, stannane and functional aryl functions, k is equal to 0 or 1 so that when k is equal to 0, $Y^-$—$F_i$ is selected from the group consisting of $OH^-$, $F^-$, $CN^-$, $RO^-$ or $RS^-$, and R is an alkyl group of 1 to 20 carbon atoms or an aryl group of 6 to 30 carbon atoms.

3. The method of claim 2, wherein, at least one of the $A_2^+$ cation and the $X_2^-$ anion of the at least one organic functionalized salt corresponding to a Y— ionic entity linked to at least one organic function $F_i$, is immobilized in the liquid matrix and cannot be extracted from the liquid matrix by solvent extraction, and the organic function or functions $F_i$ of the at least one organic functionalized salt can be converted after at least one reaction resulting from the addition of at least one reagent to said composition.

4. The method of claim 3, wherein more than one organic functionalized salt is immobilized.

5. The method of claim 2, wherein $A_2^+$ cation is organic functional.

6. The method of claim 2, wherein the $X_2^-$ anion is organic functional.

7. The method of claim 2, wherein $A_2^+$ and $X_2^-$ are organic functional.

8. The method of claim 2, wherein, said $A_1^+X_1^-$ is an ionic liquid that is solid at ambient temperature and liquefiable with a temperature range from approximately 25° C. to approximately 250° C., and said organic functionalized salt $A_2^+X_2^-$ is selected from the group consisting of: an ionic liquid that is solid at ambient temperature and that is soluble in a liquefied solid form of $A_1^+X_1^-$, and an ionic liquid that is a liquid at ambient temperature and that is miscible with the liquefied solid form of $A_1^+X_1^-$.

9. The method of claim 2, wherein, said $A_1^+X_1^-$ is an ionic liquid that is liquid at ambient temperature, and said organic functionalized salt $A_2^+X_2^-$ is selected from the group consisting of: an ionic liquid that is solid at ambient temperature and that is soluble or partially soluble in the liquid form of $A_1^+X_1^-$ within a temperature range from approximately 25° C. to approximately 250° C., and an ionic liquid that is liquid at ambient temperature and that is miscible with the liquid form of $A_1^+X_1^-$.

10. The method of claim 1, wherein said non-functionalized ionic liquid of formula $A_1^+X_1^-$ has a viscosity less than or equal to approximately 1500 cp (15 N·s/m²).

11. A method of performing a Heck coupling reaction, in a stable composition comprising, in solution:

an non-functionalized ionic liquid of formula $A_1^+X_1^-$ providing a liquid matrix; and one organic functionalized salt of formula $A_2^+X_2^-$ providing a soluble reaction support and being dissolved in the liquid matrix so that the composition forms a homogeneous phase, wherein, $A_1^+$ is a non organic-functional cation or a mixture of cations in which none of the cations is organic functional, $X_1^-$ is a non organic-functional anion or a mixture of anions in which none of the anions is organic functional, $A_2^+$ is selected from the group consisting of an organic functional cation, non organic-functional cation, a mixture of cations in which none of the cations is organic functional, and a mixture of cations in which at least one cation is organic functional, $X_2^-$ is selected from the group consisting of an organic functional anion, a non organic-functional anion, a mixture of anions in which none of the anions is organic functional, and a mixture of anions in which at least one anion is organic functional, at least one of $A_2^+$ and $X_2^-$ is an organic functional ion, said organic functional cation is of a formula $Y^+$-L-$F_i$, and said organic functional anion is of a formula $Y^-$-$(L)_k$-$F_i$, $Y^+$— and $Y^-$ are ionic entities, the charge of which corresponding to the charge of the cation of formula $Y^+$-L-$F_i$ and the charge of the anion of formula $Y^-$-$(L)_k$-$F_i$, respectively, linked via an linker L to at least one organic function $F_i$, L is an alkyl group of 1 to 20 carbon atoms, $F_i$ varies from $F_0$ to $F_n$, n being an integer varying from 1 to 10, with $F_0$ being an organic function initially linked to said cationic entities and anionic entities and $F_1$ to $F_{10}$ being organic functions converted from said $F_0$ after sequential and subsequent reactions with said cationic or anionic entities, said organic function $F_i$ is selected from the group consisting of hydroxyl, carboxylic, amide, sulphone, primary amine, secondary amine, aldehyde, ketone, ethenyl, ethynyl, dienyl, ether, epoxide, primary phosphine, secondary phosphine, tertiary phosphine, azide, imine, ketene, cumulene, heterocumulene, thiol, thioether, sulphoxide, phosphorus-containing moieties, heterocycles, sulphonic acid, silane, stannane and functional aryl functions, k is equal to 0 or 1 so that when k is equal to 0, $Y^-$—$F_i$ is selected from the group consisting of $OH^-$, $F^-$, $CN^-$, $RO^-$ or $RS^-$, and R is an alkyl group of 1 to 20 carbon atoms or an aryl group of 6 to 30 carbon atoms, said method comprising preparing said stable composition by combining a liquid matrix including at least a non-functionalized ionic liquid of formula $A_1^+X_1^-$ with at least one organic functionalized salt of formula $A_2^+X_2^-$ wherein said Heck coupling reaction is continuous, discontinuous, combinatorial, parallel, and/or for preparing libraries of products.

12. The method of claim 2, wherein said non-functionalized ionic liquid of formula $A_1^+X_1^-$ has a viscosity less than or equal to approximately 1500 cp (15 N·s/m²).

13. A method for the preparation of a molecule G, in a stable composition, said stable composition comprising, in solution:

a non-functionalized ionic liquid of formula $A_1^+X_1^-$ providing a liquid matrix; and one organic functionalized salt of formula $A_2^+X_2^-$ providing a soluble reaction support and being dissolved in the liquid matrix so that the composition forms a homogeneous phase, wherein, $A_1^+$ is a non organic-functional cation or a mixture of cations in which none of the cations is organic functional, $X_1^-$ is a non organic-functional anion or a mixture of anions in which none of the anions is organic functional, $A_2^+$ is selected from the group consisting of an organic functional cation, non organic-functional cation, a mixture of cations in which none of the cations is organic functional, and a mixture of cations in which at least one cation is organic functional, $X_2^-$ is selected from the group consisting of an organic functional anion, a non organic-functional anion, a mixture of anions in which none of the anions is organic functional, and a mixture of anions in which at least one anion is organic functional, at least one of $A_2^+$ and $X_2^-$ is a functional ion, said organic functional cation is of a formula $Y^+$-$L$-$F_i$, and said organic functional anion is of a formula $Y^-$-$(L)_k$-$F_i$, $Y^+$— and $Y^-$ are ionic entities, the charge of which corresponding to the charge of the cation of formula $Y^+$-$L$-$F_i$ and the charge of the anion of formula $Y^-$-$(L)_k$-$F_i$, respectively, linked via an linker L to at least one organic function $F_i$, L is an alkyl group of 1 to 20 carbon atoms, $F_i$ varies from $F_0$ to $F_n$, n being an integer varying from 1 to 10, with $F_0$ being an organic function initially linked to said cationic entities and anionic entities and $F_1$ to $F_{10}$ being organic functions converted from said $F_0$ after sequential and subsequent reactions with said cationic or anionic entities, said organic function $F_1$ is selected from the group consisting of hydroxyl, carboxylic, amide, sulphone, primary amine, secondary amine, aldehyde, ketone, ethenyl, ethynyl, dienyl, ether, epoxide, primary phosphine, secondary phosphine, tertiary phosphine, azide, imine, ketene, cumulene, heterocumulene, thiol, thioether, sulphoxide, phosphorus-containing moieties, heterocycles, sulphonic acid, silane, stannane and functional aryl functions, k is equal to 0 or 1 so that when k is equal to 0, $Y^-$—$F_i$ is selected from the group consisting of $OH^-$, $F^-$, $CN^-$, $RO^-$ or $RS^-$, and R is an alkyl group of 1 to 20 carbon atoms or an aryl group of 6 to 30 carbon atoms, said molecule G having an initial organic function $F_0$ linked via a L linker of an alkyl group of 1 to 20 carbon atoms to a $Y^+$-ionic entity forming part of the $A_2^+$ cation of the said $A_2^+X_2^-$ and/or $Y^-$— organic functionalized salt, forming part of the $X_2^-$ anion of the said $A_2^+X_2^-$ organic functionalized salt, the cation being in the form $Y^+$-$L$-$F_0$ and/or the anion being in the form $Y^-$-$(L)_k$-$F_0$, k being equal to 0 or 1, said method comprising:

adding a reagent $B_1$ to the said stable composition to react with organic function $F_0$ and produce an organic function $F_1$, $F_1$ being linked to the $Y^+$— ionic entity, forming part of the $A_2^+$ cation of the $A_2^+X_2^-$ organic functionalized salt, and/or to the $Y^-$— ionic entity, forming part of the $X_2^-$ anion of the $A_2^+X_2^-$ organic functionalized salt, according to one of the immediately below reaction schemes:

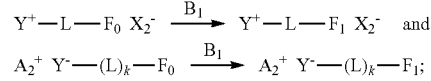

adding $B_i$ reagents in n–1 successive steps, $1<i≤n$, n varying from 2 to 10, to the said stable composition reacted with $B_1$ so that each reagent $B_i$ reacts with an organic function $F_{i-1}$, leading to the obtaining of an organic function $F_i$, the $(n-1)^{th}$ addition of the reagent $B_n$ to the organic function $F_{n-1}$ leading to the obtaining of the organic function $F_n$, the n–1 successive reactions steps according to one of the immediately below reaction schemes:

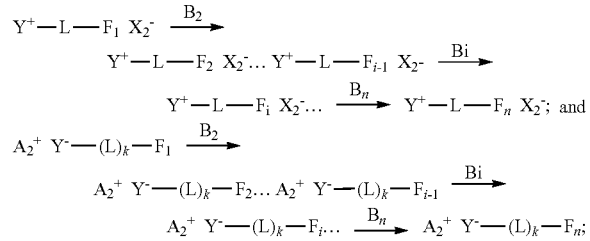

cleaving the organic function $F_n$, to recover the molecule G and the $A_2^+X_2^-$ organic functionalized salt, wherein $F_n$ is linked to the $Y^+$— or $Y^-$— ionic entity, of the $A_2^+$ cation and/or of the $X_2^-$ anion respectively, the $A_2^+X_2^-$ organic functionalized salt is recovered in the form $Y^-$-$(L)_k$-$F_0$ $X_2^-$ or $A_2^+$ $Y^-$-$(L)_k$-$F_0$, in solution in the $A_1^+X_1^-$ ionic liquid matrix or in the $Y^+$-$L$-$F'_0$ $X_2^-$ or $A_2^+$ $Y^-$-$(L)_k$-$F'_0$, in which $F'_0$ represents an organic function different from $F_0$, and said cleaving is selected from the group consisting of:

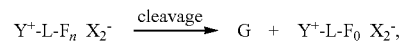

-continued

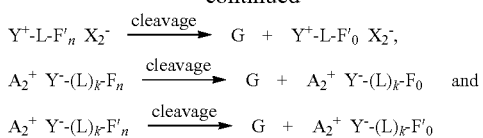

wherein,
adding a reagent $B_1$ is an esterification or amidation step and adding a reagent $B_2$ is a Heck's coupling reaction step such that the adding reagents and cleaving steps are defined as:

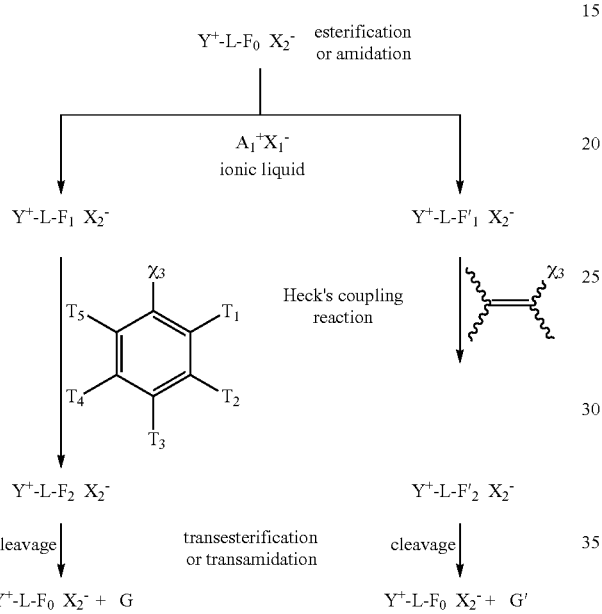

wherein
- $Y^+$— is a trimethylalkylammonium, triethylalkylammonium or tributylalkylphosphonium cation,
- L is selected from the group consisting of: a linear alkyl group of 1 to 20 carbon atoms, a branched alkyl group of 1 to 20 carbon atoms, and a functional aralkyl group of 6 to 30 carbon atoms,
- $X_2^-$ is selected from the group consisting of $BF_4^-$, $PF_6^-$, $NTf_2^-$, $CF_3SO_3^-$, $Cl^-$, $Br^-$, and $I^-$,
- $A_1^+$ is selected from the group consisting of:

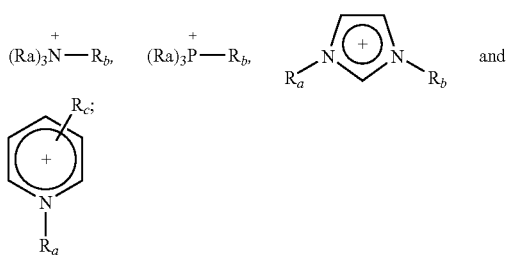

$R_a$ and $R_b$ are each selected from the group consisting of linear or branched alkyl groups, of 1 to 20 carbon atoms, functional alkyl groups of 1 to 20 carbon atoms, and functional or non-functional aryl groups of 6 to 30 carbon atoms, $X_1^-$ is selected from the group consisting of: $BF_4^-$, $PF_6^-$, $NTf_2^-$, $Cl^-$, $Br^-$, $CH_3COO^-$, $CF_3CO_2^-$, $CF_3SO_3^-$ and $BR_4^-$, R is selected from the group consisting of: an alkyl group of 1 to 20 carbon atoms, an aryl group of 6 to 30 carbon atoms, a perfluorinated group, partially fluorinated group, and the $R'SO_4^-$ anions, R' is selected from the group consisting of a hydrogen atom, a methyl group and an ethyl group, $F_0$ is a $-\chi_1H$ group, $F_1$ is

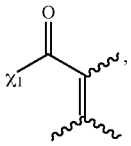

$F_2$ is

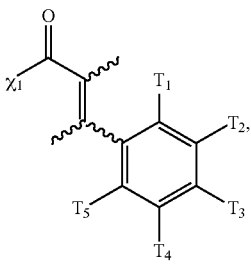

G is

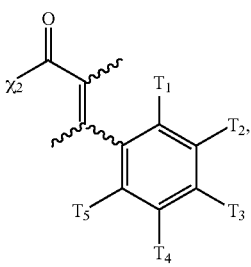

$F'_1$ is

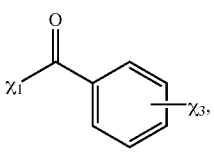

$F'_2$ is

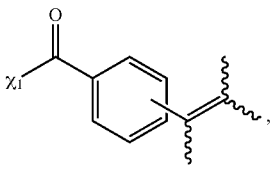

G' is

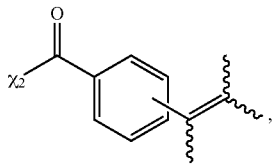

$\chi_1$ is an oxygen atom or an —$NR_f$ group, $R_f$ is linear or branched alkyl group of 1 to 20 carbon atoms or an aryl group of 6 to 30 carbon atoms, $\chi_2$ is either an $OR_g$ group or an —$NR_hR_u$ group, $R_g$ is a hydrogen atom or an alkyl group of 1 to 20 carbon atoms, and $R_h$ and $R_u$ are independently of each other selected from the group consisting of a hydrogen atom, an alkyl group of 1 to 20 carbon atoms or an aryl group of 6 to 30 carbon atoms, $\chi_3$ is a leaving moiety selected from the group consisting of I, Cl, Br, mesylate, tosylate, triflate, sulphonate, sulphate and phosphate groups, $T_1$, $T_2$, $T_3$, $T_4$ and $T_5$ are each independently of one another selected from the group consisting of a hydrogen atom, a linear or branched alkyl group of 1 to 20 carbon atoms or an aryl group of 6 to 30 carbon atoms, or an organic functional group in particular chosen from $NO_2$, CN, COOR, OR, COR, NHCOR, NRR", $SO_2R$, I, and Br, R and R" are independently of each other an alkyl group of 1 to 20 carbon atoms or an aryl group of 6 to 30 carbon atoms, and the entity

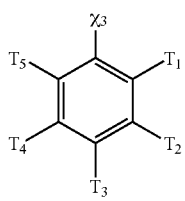

is selected from the group consisting of:

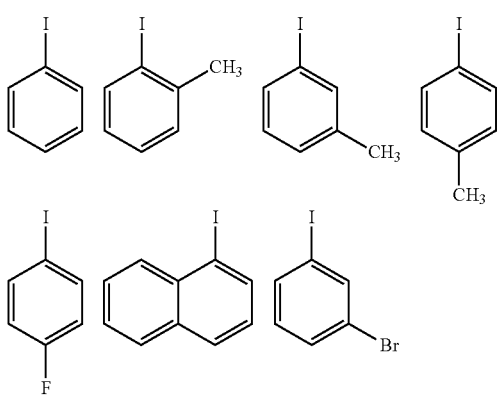

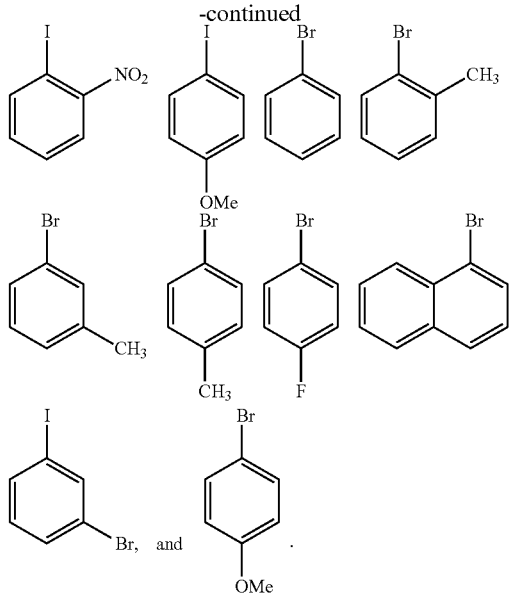

14. The method of claim 2, further comprising
separating the $Y^+$-L-$F_1$ $X_2^-$ organic functionalized salt in the $A_1^+X_1^-$ ionic liquid into n approximately equal parts, n is 2 to 1024;
converting each $Y^+$-L-$F_1$ $X_2^-$ organic functionalized salt by an organic synthesis with a different reagent $B_i$, i varying from 1 to n, in order to produce n solutions each containing a defined $Y^+$-L-$F_2^i$ $X_2^-$ compound, $F_2^i$ representing one of the organic functions, i varying from 1 to n;
cleaving each $Y^+$-L-$F_2^i$ $X_2^-$ compound to release $G_i$ molecule, i varying from 1 to n; and
isolating and purifying each $G_i$ molecule to obtain a molecular library, wherein said separating, converting and cleaving according to the following reaction diagram:

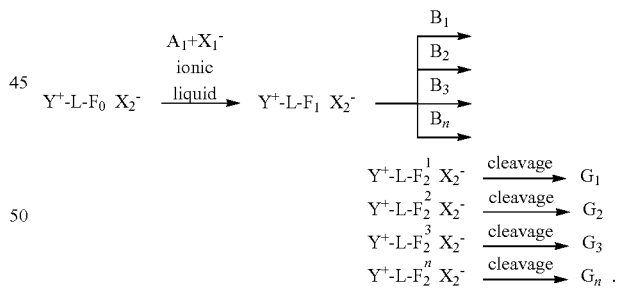

15. The method of claim 2, further comprising:
obtaining n fractions of the $Y^+$-L-$F_1$ $X_2^-$ solution from the $Y^+$-L-$F_0$ $X_2^-$ organic functionalized salt, in the $A_1^+X_1^-$ ionic liquid;
converting said n fractions in parallel according to an organic chemistry reaction, each using a different reagent $B_i$ in order to produce n solutions, each solution containing defined $Y^+$-L-$F_2^i$ $X_2^-$ compound, i varying from 1 to n, n varying from 2 to 1024, $F_2^i$ representing one of the organic functions,
mixing the n-fractions in order to produce a solution in the $A_1^+X_1^-$ ionic liquid containing the n $Y^+$-L-$F_2^i$ $X_2^-$ products, annotated by

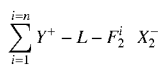

cleaving the solution annotated by

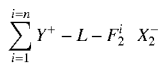

by transesterification or transamidation, in order to obtain in solution in the $A_1^+X_1^-$ ionic liquid, a mixture of n $G_i$ molecules, i varying from 1 to n, and the starting $Y^+$-L-$F_0$ $X_2^-$ organic functionalized salt;

separating the n $G_i$ molecules from the $A_1^+X_1^-$ ionic liquid and from the starting $Y^+$-L-$F_0$ $X_2^-$ organic functionalized salt in order to obtain a library containing n $G_i$ molecules, said separating being a method selected from the group consisting of vacuum distillation, solvent extraction with heptane or toluene followed by evaporation of the solvent, chromatography on a column, chromatography on a plates and chromatography under pressure; and repeating each mixing, cleaving and separating step j times, j being comprised between 2 and 10, in order to obtain j different libraries of n products, wherein said mixing, cleaving and separating reactions are represented by

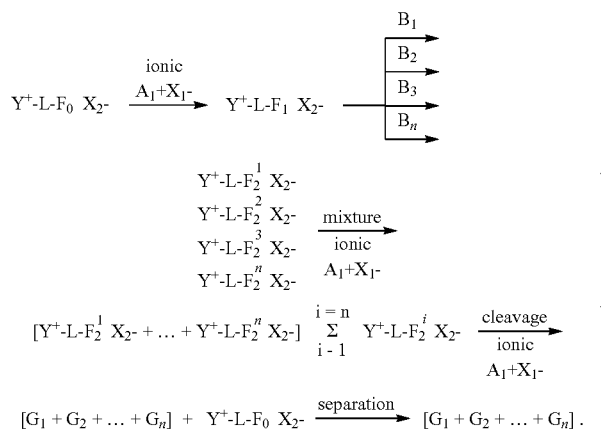

16. A method for preparing a molecule from a stable composition comprising:

(i) providing said stable composition comprising:
an ionic liquid matrix of formula $A_1^+X_1^-$ with non organic-functional ions; and
a organic functionalized salt of formula $A_2^+X_2^-$ with at least one organic-functional ion that is dissolved in the ionic liquid matrix so that the composition forms a homogeneous phase,
wherein,
$A_1^+$ and $A_2^+$ are substituted or non-substituted onium cations selected from the group consisting of pyridinium, imidazolium, ammonium, phosphonium or sulphonium cations, and
$X_1^-$ and $X_2^-$ anions are selected from the group consisting of $BF_4^-$, $PF_6^-$, $CF_3SO_3^-$, $CH_3COO^-$, $CF_3CO_2^-$, $^-N(SO_2CF_3)_2$, halides, $BR_4^-$, $RCO_2^-$ and $RSO3^-$ with R selected from the group consisting of an alkyl group of 1 to 20 carbon atoms, an aryl group of 6 to 30 carbon atoms, a perfluorinated or partially fluorinated group, $R'SO_4$ with R' being selected from the group consisting of a hydrogen atom, a methyl group or an ethyl group, and complex anions resulting from the combination of a Lewis acid and a halide X of general formula $MX_j$ with j being an integer between 1 and 7, X being a halide and M representing a metal selected from the group consisting of aluminium, tin, zinc, bismuth, manganese, iron, copper, molybdenum, antimony, gallium or indium, both $A_1^+$ and $X_1^-$ being non organic-functional ions, and at least one of $A_2^+$ and $X_2^-$ is an organic functional ion, said at least one organic functional ion is one of an organic functional cation of a formula is $Y^+$-L-$F_i$, and an organic functional anion of a formula $Y^-$-$(L)_k$-$F_i$, $Y^+$— and $Y^-$ are ionic entities, the charge of which corresponding to the charge of the cation of formula $Y^+$-L-$F_i$ and the charge of the anion of formula $Y^-$-$(L)_k$-$F_i$, respectively, L is an alkyl group of 1 to 20 carbon atoms, $F_i$ is an organic function varying from $F_0$ to $F_n$, and selected from the group consisting of hydroxyl, carboxylic, amide, sulphone, primary amine, secondary amine, aldehyde, ketone, ethenyl, ethynyl, dienyl, ether, epoxide, primary phosphine, secondary phosphine, tertiary phosphine, azide, imine, ketene, cumulene, heterocumulene, thiol, thioether, sulphoxide, phosphorus-containing moieties, heterocycles, sulphonic acid, silane, stannane and functional aryl functions, $F_0$ being an organic function initially linked to said ionic entities, n being an integer varying from 1 to 10 representing a number of reactions, $F_1$ to $F_{10}$ being organic functions converted from said $F_0$ after sequential reactions with said ionic entities, k is equal to 0 or 1 so that when k is equal to 0, $Y^-$—$F_i$ is selected from the group consisting of $OH^-$, $F^-$, $CN^-$, $RO^-$ or $RS^-$, and R is an alkyl group of 1 to 20 carbon atoms or an aryl group of 6 to 30 carbon atoms;

(ii) adding $B_i$ reagents to the stable composition, in n−1 successive steps, 1<i≤n, n varying from 2 to 10, to obtain successive organic functions $F_1$ until $F_n$ on the ionic entity, wherein, reagent $B_1$ reacts with organic function $F_0$ to produce an organic function $F_1$ containing composition according to a Heck coupling reaction, $F_1$ being linked at least one of the $Y^+$— ionic entity with the reaction being

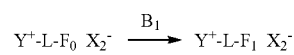

and the $Y^-$— ionic entity with the reaction being

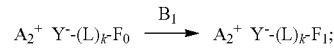

(iii) reacting each reagent $B_i$ with an organic function $F_{i-1}$, leading to the obtaining of an organic function $F_i$, the (n−1)$^{th}$ addition of the reagent $B_n$ to the organic function $F_{n-1}$ leading to the obtaining of the organic function $F_n$, the n−1 successive reactions steps according to one of the immediately below reaction schemes:

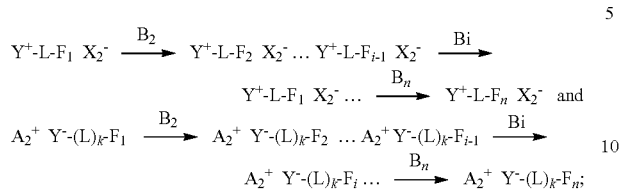

and (iv) cleaving the organic function $F_n$ and producing a molecule G so that the $A_2^+X_2^-$ organic functionalized salt is recovered in the form of at least one of $Y^+$-L-$F_0$ $X_2^-$ and $A_2^+Y^-$-(L)$_k$-$F_0$ in solution in the $A_1^+X_1^-$ ionic liquid matrix, said cleaving being at least one of the immediately below reaction schemes:

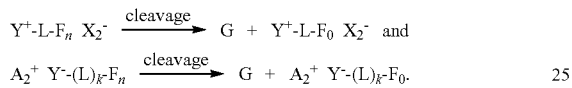

* * * * *